(12) United States Patent
Santamaria

(10) Patent No.: US 10,124,045 B2
(45) Date of Patent: Nov. 13, 2018

(54) METHODS AND COMPOSITIONS FOR SUSTAINED IMMUNOTHERAPY

(71) Applicant: UTI Limited Partnership, Calgary (CA)

(72) Inventor: Pedro Santamaria, Calgary (CA)

(73) Assignee: UTI LIMITED PARTNERSHIP, Calgary, Alberta (CA)

( * ) Notice: Subject to any disclaimer, the term of this patent is extended or adjusted under 35 U.S.C. 154(b) by 712 days.

(21) Appl. No.: 14/531,707

(22) Filed: Nov. 3, 2014

(65) Prior Publication Data

US 2015/0125536 A1    May 7, 2015

Related U.S. Application Data

(60) Provisional application No. 61/899,826, filed on Nov. 4, 2013.

(51) Int. Cl.
| | | |
|---|---|---|
| *C01G 49/08* | (2006.01) | |
| *A61K 9/51* | (2006.01) | |
| *A61K 47/69* | (2017.01) | |
| *A61K 39/00* | (2006.01) | |
| *A61K 9/00* | (2006.01) | |

(52) U.S. Cl.
CPC ........ *A61K 39/0008* (2013.01); *A61K 9/0019* (2013.01); *A61K 9/5115* (2013.01); *A61K 9/5146* (2013.01); *A61K 9/5192* (2013.01); *A61K 47/6929* (2017.08); *C01G 49/08* (2013.01); *A61K 2039/605* (2013.01); *C01P 2004/61* (2013.01); *C01P 2004/62* (2013.01); *C01P 2004/64* (2013.01); *C01P 2006/42* (2013.01); *C12N 2710/24141* (2013.01); *C12N 2740/15041* (2013.01); *Y10T 428/2982* (2015.01); *Y10T 428/2991* (2015.01)

(58) Field of Classification Search
None
See application file for complete search history.

(56) References Cited

U.S. PATENT DOCUMENTS

| | | | |
|---|---|---|---|
| 4,367,110 A | 1/1983 | Yoshikawa | |
| 4,414,148 A | 11/1983 | Jansen et al. | |
| 4,452,901 A | 6/1984 | Gordon et al. | |
| 4,478,946 A | 10/1984 | Van der Merwe et al. | |
| 4,554,101 A | 11/1985 | Hopp | |
| 4,569,789 A | 2/1986 | Blattler et al. | |
| 4,589,071 A | 5/1986 | Yamamuro et al. | |
| 4,589,330 A | 5/1986 | Teron | |
| 4,659,839 A | 4/1987 | Nicolotti et al. | |
| 4,671,958 A | 6/1987 | Rodwell et al. | |
| 4,680,338 A | 7/1987 | Sundoro | |
| 4,699,784 A | 10/1987 | Shih et al. | |
| 4,818,542 A | 4/1989 | Deluca et al. | |
| 4,859,839 A | 8/1989 | Tetelman et al. | |
| 5,258,499 A | 11/1993 | Konigsberg et al. | |
| 5,543,391 A | 8/1996 | Yatvin et al. | |
| 5,676,926 A | 10/1997 | Platzek et al. | |
| 5,676,928 A | 10/1997 | Klaveness et al. | |
| 5,731,168 A | 3/1998 | Carter et al. | |
| 5,807,706 A | 9/1998 | Carter et al. | |
| 5,821,333 A | 10/1998 | Carter et al. | |
| 5,840,839 A | 11/1998 | Wang et al. | |
| 6,103,379 A | 8/2000 | Margel et al. | |
| 6,387,498 B1 | 5/2002 | Coulter et al. | |
| 6,651,655 B1 | 11/2003 | Licalsi et al. | |
| 6,688,494 B2 | 2/2004 | Pozarnsky et al. | |
| 6,712,997 B2 | 3/2004 | Won et al. | |
| 6,797,514 B2 | 9/2004 | Berenson et al. | |
| 6,846,474 B2 | 1/2005 | Nayfeh et al. | |
| 6,929,675 B1 | 8/2005 | Bunge et al. | |
| 7,060,121 B2 | 6/2006 | Lin et al. | |
| 7,285,289 B2 | 10/2007 | Nagy et al. | |
| 7,326,399 B2 | 2/2008 | Zhou et al. | |
| 7,332,586 B2 | 2/2008 | Franzen et al. | |
| 7,361,733 B2 | 4/2008 | Hersberg et al. | |
| 7,572,631 B2 | 8/2009 | Berenson et al. | |
| 7,642,228 B2 | 1/2010 | Carter et al. | |
| 7,695,936 B2 | 4/2010 | Carter et al. | |
| 8,216,805 B2 | 7/2012 | Carter et al. | |
| 8,354,110 B2 | 1/2013 | Santamaria et al. | |
| 8,679,785 B2 | 3/2014 | Carter et al. | |
| 8,835,144 B2 | 9/2014 | Jiang et al. | |
| 9,149,440 B2 | 10/2015 | Turos et al. | |
| 9,511,151 B2 | 12/2016 | Santamaria et al. | |
| 2003/0068363 A1 | 4/2003 | Clark et al. | |
| 2003/0124149 A1 | 7/2003 | Shalaby et al. | |
| 2004/0115216 A1 | 6/2004 | Schneck et al. | |
| 2004/0137642 A1 | 7/2004 | Erfle et al. | |
| 2004/0265392 A1 | 12/2004 | Tovar et al. | |

(Continued)

FOREIGN PATENT DOCUMENTS

| | | |
|---|---|---|
| CA | 2517097 A1 | 9/2004 |
| CA | 2717719 A1 | 8/2009 |

(Continued)

OTHER PUBLICATIONS

Xie et al (Pure Appl. Chem., 2006, 78(5): 1003-1014).*
Xie et al (Adv. Mater. 2007, 19: 3163-3166).*
Miguel-Sancho et al (Chem. Mater. 2011, 23: 2795-2802).*
Xu et al (Chem. Mater. 2009, 21:1778-1780).*
Wang et al ( J. Nanopart. Res. Nov. 6, 2012, 14: 755).*
Aichele et al., "Peptide-induced T-cell tolerance to prevent autoimmune diabetes in a transgenic mouse model," Proc. Nat. Acad, Sci. USA, 91: 444-448, 1994.
Amrani et al., "Progression of autoimmune diabetes driven by avidity maturation of a T-cell population," Nature, 406: 739-742, 2000.

(Continued)

*Primary Examiner* — Michael Szperka
*Assistant Examiner* — Marianne DiBrino
(74) *Attorney, Agent, or Firm* — Wilson, Sonsini, Goodrich & Rosati

(57) ABSTRACT

This disclosure provides methods of making functionalized PEG iron oxide nanoparticles.

11 Claims, 19 Drawing Sheets
Specification includes a Sequence Listing.

(56) References Cited

U.S. PATENT DOCUMENTS

| | | |
|---|---|---|
| 2005/0003431 A1 | 1/2005 | Wucherpfennig et al. |
| 2005/0118102 A1 | 6/2005 | Xiang et al. |
| 2005/0129617 A1 | 6/2005 | Tan et al. |
| 2005/0202032 A1 | 9/2005 | Kaufman et al. |
| 2005/0208120 A1 | 9/2005 | Albani |
| 2006/0219239 A1 | 10/2006 | Plaschkes |
| 2007/0054337 A1 | 3/2007 | Ferning et al. |
| 2007/0059775 A1 | 3/2007 | Hultman et al. |
| 2007/0129307 A1 | 6/2007 | Tan et al. |
| 2007/0154953 A1 | 7/2007 | Brunner et al. |
| 2009/0155292 A1 | 6/2009 | Santamaria et al. |
| 2009/0258355 A1 | 10/2009 | Maye et al. |
| 2010/0061984 A1 | 3/2010 | Greene et al. |
| 2010/0095544 A1 | 4/2010 | Haseloh |
| 2010/0104503 A1 | 4/2010 | Mellman et al. |
| 2010/0303866 A1 | 12/2010 | Saint-Remy |
| 2011/0029121 A1 | 2/2011 | Amit |
| 2011/0059121 A1 | 3/2011 | Santamaria et al. |
| 2011/0250146 A1 | 10/2011 | Zhang et al. |
| 2011/0318380 A1 | 12/2011 | Brix et al. |
| 2012/0077686 A1 | 3/2012 | Weiner et al. |
| 2012/0093934 A1 | 4/2012 | Santamaria |
| 2012/0121649 A1 | 5/2012 | Santamaria et al. |
| 2013/0128138 A1 | 5/2013 | Kuo et al. |
| 2013/0171179 A1 | 7/2013 | Burrows |
| 2013/0302421 A1 | 11/2013 | Santamaria et al. |
| 2013/0330414 A1 | 12/2013 | Santamaria |
| 2014/0105980 A1 | 4/2014 | Santamaria |
| 2014/0294982 A1 | 10/2014 | Freund et al. |
| 2014/0341938 A1 | 11/2014 | Rademacher et al. |
| 2014/0370099 A1 | 12/2014 | Green et al. |
| 2015/0125536 A1 | 5/2015 | Santamaria |
| 2015/0150996 A1 | 6/2015 | Miller et al. |
| 2015/0209446 A1 | 7/2015 | Santamaria et al. |
| 2015/0250871 A1 | 9/2015 | Santamaria |
| 2015/0374815 A1 | 12/2015 | Kishimoto et al. |
| 2016/0271237 A1 | 9/2016 | Santamaria |
| 2017/0095544 A1 | 4/2017 | Santamaria |
| 2017/0274096 A1 | 9/2017 | Santamaria |
| 2017/0312348 A1 | 11/2017 | Santamaria |
| 2017/0333540 A1 | 11/2017 | Santamaria et al. |

FOREIGN PATENT DOCUMENTS

| | | |
|---|---|---|
| CA | 2868551 A1 | 10/2013 |
| CN | 101678090 A | 3/2010 |
| EP | 0188256 A2 | 7/1986 |
| EP | 1088256 A2 | 4/2001 |
| EP | 2614834 A1 | 7/2013 |
| EP | 2621523 A1 | 8/2013 |
| JP | H07508503 A | 9/1995 |
| JP | 2001516571 A | 10/2001 |
| JP | 2002504342 A | 2/2002 |
| JP | 2002544170 A | 12/2002 |
| JP | 2003231698 A | 8/2003 |
| JP | 2005538083 A | 12/2005 |
| JP | 2006522319 A | 9/2006 |
| JP | 2008514686 A | 5/2008 |
| JP | 2010522695 A | 7/2010 |
| JP | 2013538208 A | 10/2013 |
| WO | WO-9007339 A1 | 7/1990 |
| WO | WO-9218150 A1 | 10/1992 |
| WO | WO-9316725 A1 | 9/1993 |
| WO | WO-9409823 A1 | 5/1994 |
| WO | WO-9914236 A1 | 3/1999 |
| WO | WO-0043662 A1 | 7/2000 |
| WO | WO-0067788 A2 | 11/2000 |
| WO | WO-0124764 A2 | 4/2001 |
| WO | WO-2004006951 A1 | 1/2004 |
| WO | WO-2004076909 A1 | 9/2004 |
| WO | WO-2004078909 A2 | 9/2004 |
| WO | WO-2005033267 A2 | 4/2005 |
| WO | WO-2006037979 A2 | 4/2006 |
| WO | WO-2006054806 A1 | 5/2006 |
| WO | WO-2006080951 A2 | 8/2006 |
| WO | WO-2007024026 A1 | 3/2007 |
| WO | WO-2008109852 A2 | 9/2008 |
| WO | WO-2008118861 A2 | 10/2008 |
| WO | WO-2009003492 A1 | 1/2009 |
| WO | WO-2009031258 A1 | 3/2009 |
| WO | WO-2009040811 A2 | 4/2009 |
| WO | WO-2009078799 A1 | 6/2009 |
| WO | WO-2009094273 A2 | 7/2009 |
| WO | WO-2009111588 A1 | 9/2009 |
| WO | WO-2009126835 A2 | 10/2009 |
| WO | WO-2010025324 A2 | 3/2010 |
| WO | WO-2010027827 A2 | 3/2010 |
| WO | WO-2010037395 A2 | 4/2010 |
| WO | WO-2010037397 A1 | 4/2010 |
| WO | WO-2010042876 A1 | 4/2010 |
| WO | WO-2010080032 A2 | 7/2010 |
| WO | WO-2010085509 A1 | 7/2010 |
| WO | WO-2011073685 A1 | 6/2011 |
| WO | WO-2011104497 A1 | 9/2011 |
| WO | WO-2012012874 A1 | 2/2012 |
| WO | WO-2012031258 A1 | 3/2012 |
| WO | WO-2012041968 A1 | 4/2012 |
| WO | WO-2012062904 A2 | 5/2012 |
| WO | WO-2013043662 A1 | 3/2013 |
| WO | WO-2013072051 A1 | 5/2013 |
| WO | WO-2013144811 A2 | 10/2013 |
| WO | WO-2014080286 A2 | 5/2014 |
| WO | WO-2015063616 A2 | 5/2015 |

OTHER PUBLICATIONS

Amrani et al., "Expansion of the antigenic repertoire of a single T cell receptor upon T cell activation," J Immunol., 167: 655-666, 2001.

Anderson et al., "Prevalent CD8(+) T cell response against one peptide/MHC complex in autoimmune diabetes," Proc. Nat/. Acad. Sci. USA, 96: 9311-9316, 1999.

Anderton and Wraith, "Hierarchy in the ability of T cell epitopes to induce peripheral tolerance to antigens from myelin," Eur. J. Immunol., 2S: 1251-1261, 1998.

Appay et al., "HIV-specific CDS+ T cells produce antiviral cytokines but are impaired in cytoltic function," J. Exp. Med., 192: 63-72, 2000.

Australian Patent Application No. 2016225913 Examination Report No. 1 dated Sep. 22, 2017.

Azuma et al., "T Cell Costimulation and Diseases," Stomatological Journal 67(3):233-239, 2000.

Bachmann et al., "Developmental regulation of Lck targeting to the CDS coreceptor controls signaling in naive and memory T cells," J Exp. Med., 1S9: 1521-1530, 1999.

Bahcetepe et al, "The role of HLA antigens in the aetiology of psoriasis," Med Glas (Zenica) 10(2):339-342, 2013.

Baker et al., Critical appraisal of animal models of multiple sclerosis. Multiple Sclerosis Journal, 17(6):647-657, 2011.

Barber et al., "Restoring function in exhausted CDS T cells during chronic viral infection," Nature, 439: 6S2-6S7, 2006.

Becker et al., "Interleukin 15 is required for proliferative renewal of virus-specific memory CDS T cells," J. Exp. Med., 195: 1541-1548, 2002.

Behan et al., "The sad plight of multiple sclerosis research (low on fact, high on fiction): critical data to support it being a neurocristopathy," Inflammopharmacol 18:265-290, 2010.

Betts et al., "CD8(+) T cells in asthma: Friend or foe?" Pharmacology & Therapeutics 121:123-131, 2009.

Bielekova et al., "Encephalitogenic potential of the myelin basic protein peptide (amino acids S3-99) in multiple sclerosis: results of a phase II clinical trial with an altered peptide ligand," Nat. Med., 6: 1167-1175, 2000.

Blancou et al., "Immunization of HLA class I transgenic mice identifies autoantigenic epitopes eliciting dominant responses in type 1 diabetes patients," J. Immunol., 178: 7458-66, 2007.

Bossuyt et al., Serologic markers in inflammatory bowel disease. Clinical Chemistry, 52(2):171-181, 2006.

(56) References Cited

OTHER PUBLICATIONS

Bottazzo et al., "In situ characterization of autoimmune phenomena and expression of HLA molecules in the pancreas in diabetic insulitis," N. Engl. J. Med., 313: 353-360, 1985.
Bottini et al. "Luminescent Silica Nanobeads: Characterization and Evaluation as Efficient Cytoplasmatic Transporters for T-Lymphocytes," Journal of the American Chemical Society, 129(25):7814-7823, 2007.
Bour-Jordan and Bluestone, "B cell depletion: a novel therapy for autoimmune diabetes?" J.Clin. Invest., 117: 3642-3645, 2007.
Braud et al., "Functions of nonclassical MHC and non-MHC-encoded class I molecules," Current Opinion in Immunology 11:100-108, 1999.
Can Diabetes Be Prevented? Website article from: KidsHealth, downloaded Nov. 9, 2010, 2 pages.
Canadian Patent Application No. 2,817,710 Office Action dated Oct. 19, 2017.
Cao et al., "Analysis of the frequencies of HLA-A, B, and C alleles and haplotypes in the five major ethnic groups of the United States reveals high levels of diversity in these loci and contrasting distribution patterns in these populations," Hum. Immunol., 62: 1009-1030, 2001.
Chang et al., "Design, engineering, and production of human recombinant T-cell receptor ligands derived from human leukocyte antigen DR2," Journal of Biological Chemistry 276(26) :24170-6, 2001.
Chatenoud et al., "Do NKT cells control autoimmunity?" J. Clin. Invest. 110(6):747-748, 2002.
China Patent Application No. 201380022126.2 fourth Office Action dated Jul. 24, 2017.
Cirillo et al., S100B protein in the gut: The evidence for enteroglialsustained intestinal inflammation. World J Gastroenterol ,17(10): 1261-1266, 2011.
Clemente-Casares, et al., "Expanding antigen-specific regulatory networks to treat autoimmunity," Nature 530:434-440, 2016.
Clemente-Casares, J. "pMHC-class II Nanovaccine to Treat Autoimmune Diseases," Doctor of Philosophy Thesis, Calgary University, Alberta, Canada, 391 pages, 2014. retrieved from: http://theses.ucalgary.ca/handle/11 023/1589.
Clemente-Caseres et al , Peptide-MHC-based nanovaccines for the treatment of autoimmunity: a "one size fits all" approach? J. Mol. Med., 89: 733-742, 2011.
Cnop et al., "Mechanisms of Pancreatic beta-Cell Death in Type 1 and Type 2 Diabetes," Diabetes 54(2):S97-S107.
Constantinescu et al., "Experimental autoimmune encephalomyelitis (EAE) as a model for multiple sclerosis (MS)," British Journal of Pharmacology 164:1079-1106, 2011.
Corrigall et al., "Autoantigens and immune pathways in rheumatoid arthritis," Crit Rev Immunol. 22(4):281-293, 2002.
Croxford et al., "Mouse models for multiple sclerosis: Historical facts and future implications," Biochimica et Biophysica Acta 1812:177-183, 2011.
Cuiv et al., "Draft Genome Sequence of Bacteroides vulgatus PC510, a Strain Isolated from Human Feces," Journal of Bacteriology 193(15):4025-4026, 2011.
Database Accession No. ADK001 000110. "Bacteroides vulgatus PC 510 contig00041, whole genome shotgun sequence." 2011.
UniProtKB-Database Accession No. D4VD94. "Submitted name: Conserved domain protein, CUU_1332." from: www.uniprot.org/uniprot/D4VD94. 2010.
Denic et al., "The relevance of animal models in multiple sclerosis research," Pathophysiology 18:21-29, 2011.
Diabetes Prevention Trial—Type 1 Diabetes Study Group, "Effects of insulin in relatives of patients with type 1 diabetes mellitus," N. Engl. J. Med., 346:1685-1691, 2002.
Dieterich et al., Identification of tissue transglutaminase as the autoantigen of celiac disease. Nature Medicine, 3(7):797-801, 1997.
DiLorenzo et al., "Major histocompatibility complex class !-restricted T cells are required for all but the end stages of diabetes development in nonobese diabetic mice and use a prevalent T cell receptor alpha chain gene rearrangement," Proc. Nat!. Acad. Sci. USA, 95: 12538-12543, 1998.
Diwan et al., "Biodegradable nanoparticle mediated antigen delivery to human cord blood derived dendritic cells for induction of primary T cell responses," J. Drug Target 11 (8-1 0):495-507, 2003.
Dominguez, et al. Targeting the tumor microenvironment with anti-neu/anti-CD40 conjugated nanoparticles for the induction of antitumor immune responses, Vaccine, 28(15):1383-1390, 2010.
Dressel et al., "Autoantigen recognition by human CD& T cell clones: enhanced agonist response induced by altered peptide ligands," J. Immunol., 159: 4943-51, 1997.
Eggena et al. Identification of Histone H1 as a Cognate Antigen of the Ulcerative Colitis-associated Marker Antibody pANCA. Journal of Autoimmunity 14:83-97, 2000.
European Patent Application No. 13856460.4 Extended European Search Report dated Feb. 26, 2016.
Fennessy et al., "A gene in the HLA class I region contributes to susceptibility to IDDM in the Finnish population. Childhood Diabetes in Finland (DiMe) Study Group," Diabetologia, 37:937-945, 1994.
Fifis et al., "Short Peptide Sequences Containing MHC Class I and/or Class II Epitopes Linked to Nano-Beads Induce Strong Immunity and Inhibition of Growth of Antigen-Specific Tumour Challenge in Mice," Vaccine 23(2):258-266, 2004.
Flad et al., "Development of an MHC-class I peptide selection assay combining nanoparticle technology and matrix-assisted laser desorption/ionisation mass spectrometry," J. Immunol. Meth. 283:205-213, 2003.
Frankel et al., "Characterization of diphtheria fusion proteins targeted to the human interleukin-3 receptor," Protein Engineering 13(8):575-581, 2000.
Gill et al., "Characterization of Primary T Cell Subsets Mediating Rejection of Pancreatic Islet Grafts," Journal of Immunology, 143:2176-2178, 1989.
Gimmi et al., "Human T-cell clonal anergy is induced by antigen presentation in the absence of B7 costimulation," Proc. Natl. Acad. Sci. USA 90:65S6-6590, 1993.
Gold et al., "Understanding pathogenesis and therapy of multiple sclerosis via animal models: 70 years of merits and culprits in experimental autoimmune encephalomyelitis research," Brain 129:1953-1971, 2006.
Gong, et aL Immobilized MHC class I chain-related protein .A synergizes with IL-15 and soluble 4-1BB ligand to expand NK cells with high cytotoxicity ex vivo. Cellular & Molecular Immunology, 7(6):477-484, 2010.
Gregori et al., "Re-establishing immune tolerance in type 1 diabetes via regulatory T cells," Novartis Found Symp. 292:abstract, 2008.
Guarda et al., "L-selectin-negative CCR7-effector and memory CD8+ T cells enter reactive lymph nodes and kill dendritic cells," Nat. Immunol., 8: 743-752, 2007.
Gunn et al., A multimodal targeting nanoparticle for selectively labeling T cells. Small. 4(6):712-715, 2008.
Guo et al., "Protein tolerance to random amino acid change," PNAS 101 (25):9205-9210, 2004.
Gupta et al., Synthesis and surface engineering of iron oxide nanoparticles for biomedical applications. Biomat. 26:3995-4021, 2005.
Hamilton-Williams et al., "Transgenic rescue implicates beta2-microglobulin as a diabetes susceptibility gene in nonobese diabetic (NOD) mice," Proc. Natl. Acad. Sci. USA, 98: 11533, 2001.
Han et a!., "Prevention of diabetes by manipulation of anti-IGRP autoimmunity: high efficiency of a low-affinity peptide," Nat. Med., 11: 645-652, 2005.
Han et al., Interleukin-17-producing yt>+ T cells protect NOD mice from type 1 diabetes through a mechanism involving transforming growth factor-p, Immunology, 129:197-206, 2009.
Han et al., "Developmental control of CD& T cell-avidity maturation in autoimmune diabetes," J. Clin. Invest., 115: 1879-87, 2005.
Harris et al., "Prediction of murine MHC class I epitopes in a major house dust mite allergen and induction ofT1-type CDS T cell responses," Int Immunol. 9(2):273-280, 1997.

(56) References Cited

OTHER PUBLICATIONS

Hassainya et al., "Identification of naturally processed HLA-A2-restricted pro insulin epitopes by reverse immunology.," Diabetes, 54: 2053-2059, 2006.
Herold et al., "Anti-CD3 monoclonal antibody in new onset type I diabetes mellitus," N. Eng. J. Med., 346:1692-169S, 2002.
Ho et al., "The clinical relevance of autoantibodies in scleroderma," Arthritis Res Ther. 5(2):80-93, 2003.
Holgate and Polosa, Treatment strategies for allergy and asthma. Nature, 8: 218-230, 2008.
Honeyman et al., "Analysis of families at risk for insulin-dependent diabetes mellitus reveals that HLA antigens influence progression to clinical disease," Mol. Med., 1: 576-5S2, 1995.
Itoh et al., "Mononuclear cell infiltration and its relation to the expression of major histocompatibility complex antigens and adhesion molecules in pancreas biopsy specimens from newly diagnosed insulin-dependent diabetes mellitus patients," J. Clin. Invest., 92: 2313-2322, 1993.
Japan Intractable Diseases Information Center. "Crohn's Disease,"nanbyou.or.jp/entry/111. 2015.
Japan Intractable Diseases Information Center. "Sjogren's Syndrome," nanbyou.or.jp/entry/S1. 2015.
Japanese Patent Application No. 2015-536240 Office Action dated Aug. 16, 2017.
Japanese Patent Application No. 2017-014194 Office Action dated Sep. 13, 2017.
Jarchum et al., "Identification of novel IGRP epitopes targeted in type I diabetes patients," Clin. Immunol., 127:359-365, 2008.
Jarchum et al., "In vivo cytotoxicity of insulin-specific CDS+ T-cells in HLA-A *020 1 transgenic NOD mice," Diabetes, 56: 2551-60, 2007.
Jarius et al., "Mechanisms of Disease: aquaporin-4 antibodies in neuromyelitis optica," Nat Clin Pract Neurol. 4(4):202-214, 2008.
Judge et al, "Interleukin 15 controls both proliferation and survival of a subset of memoryphenotype CDS+ T cells," J. Exp. Med., 196: 935-946, 2002.
Jun et al., "A new look at viruses in type 1 diabetes," Diabetes Metab. Res. Rev. 19:8-31, 2003.
Jurewicz et al., "MHC class !-restricted lysis of human oligodendrocytes by myelin basic protein peptide-specific CDS T lymphocytes," J. Immunol., 160: 3056-3059, 1998.
Kamikura et al., "VII. Adhesion, Costimulatory Molecule, Trafficking, Homing: 1. Cancer X Immunotherapy and Costimulatory Molecule," Annual Review, Immunity 162:2-13, 2004.
Kappas et al., "Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group," Nat. Med., 6:1176-11S2, 2000.
Karin et al., "Reversal of experimental autoimmune encephalomyelitis by a soluble peptide variant of a myelin basic protein epitope: T cell receptor antagonism and reduction of interferon gamma and tumor necrosis factor alpha production," J. Exp. Med., 180: 2227-2237, 1994.
Karounos et al., Metabolically inactive insulin analog prevents Type 1 diabetes in prediabetic NOD mice. JCI, 100(6):1344-1348, 1997.
Kent et al., "Expanded T cells from pancreatic lymph nodes of type 1 diabetic subjects recognize an insulin epitope," Nature, 435: 224-228, 2005.
Keymeulen et al., "Insulin needs after CD3-antibody therapy in new-onset type 1 diabetes," N. Engl. J. Med., 352: 2598-2608, 2005.
Kim et al., "Induction and visualization of mucosal memory CDS T cells following systemic virus infection," J. Immunol., 163:4125-4132, 1999.
Kita et al., "Quantitative and functional analysis of PDC-E2-specific autoreactive cytotoxic T lymphocytes in primary biliary cirrhosis," J Clin Invest. 109(9):1231-1240, 2002.
Komai-Koma. "TIR2 is expressed on activated T cells as a costimulatory receptor," Proceedings of the National Academy of Sciences, 181(9):3829-3834, 2004.
Krishnamoorthy et al., Myelin-specific T cells also recognize neuronal autoantigen in a transgenic mouse model of multiple sclerosis, Nature Medicine 15(6):626-633, 2009.
Kukreja et al., NKT cells and Type-1 diabetes and the « Hygiene Hypothesis » to explain the rising incidence rates. Diabet. Tech. Ther. 4(3):323-333, 2002.
Kulmala et al., "Prediabetes in Children," Pediatr Drugs, 5(4):211-221, 2003.
Kwong et al. "Synthesis and characterization of antibody-nano particle conjugates for locally sequestered tumor immunotherapy," Abstracts of Papers American Chemical Society, 240: POLY 61, 2010.
Kyger et al., "Effective Arrestin-Specific Immunotherapy of Experimental Autoimmune Uveitis with RTL: A Prospect for Treatment of Human Uveitis," Transl Vis Sci Technol. 2(2): 1-15, 2013.
Laurence and O'Shea, TH-17 differentiation: of mice and men. Nature Immunology, 8(9):903-905, 2007.
Lechner et al., "Analysis of successful immune responses in persons infected with hepatitis C virus," J. Exp. Med., 191:1499-1510, 2000.
Lee, et at. "Biodegradable nanoparticles containing TLR3 or TLR9 agonists together with antigen enhance MHC-restricted presentation of the antigen," Archives of Pharmacal Research, 33(11):1859-1866,2010.
Liblau et al., "Autoreactive CDS T cells in organ-specific autoimmunity: emerging targets for therapeutic intervention," Immunity, 17:1-6, 2002.
Lieberman and DiLorenzo, "A comprehensive guide to antibody and T-cell responses in type 1 diabetes.," Tissue Antigens, 62: 359-377, 2003.
Lieberman et al., "Identification of the 3 cell antigen targeted by a prevalent population of pathogenic CD8+ T cells in autoimmune," Proc. Nat!. A cad. Sci. USA, 100: 8384-8388, 2003.
Lieberman et al., "Individual nonobese diabetic mice exhibit unique patterns of CDS+ T cell reactivity to three islet antigens, including the newly identified widely expressed dystrophia myotonica kinase," J. Immunol., 173: 6727-6734, 2004.
Longhi et al., "Autoantigen-Specific Regulatory T Cells, a Potential Tool for Immune-Tolerance Reconstitution in Type-2 Autoimmune Hepatitis," Hepatology 53(2):536-547, 2011.
Lowery et al., "Immunonanoshells for targeted photothermal ablation of tumor cells," Int J Nanomedicine 1 (2):149-154, 2006.
Ma et al., TCR triggering by pMHC ligands tethered on surfaces via Poly(Ethylene Glycol) depends on polymer length. PLOS one, 9(11):e112292, pp. 1-10, 2014.
Mallone et al., "CD8+ T-cell responses identify beta-cell autoimmunity in human type 1 diabetes," Diabetes, 56: 613-621, 2007.
Mallone et al., "T Cell Recognition of Autoantigens in Human Type 1 Diabetes: Clinical Perspectives," Clinical and Developmental Immunology (513210): 1-16, 2011.
Maree et al., "Modeling competition among autoreactive CDS+ T cells in autoimmune diabetes: implications for antigen-specific therapy," Int. Immunol., 18: 1067-1077, 2006.
Mars et al., "CDS T cell responses to myelin oligodendrocyte glycoprotein-derived peptides in humanized HLA-A *0201-transgenic mice," J. Immunol., 179: 5090-5098, 2007.
Marsh et al., "Nomenclature for factors of the HLA system, update Oct. 2010," Human Immunology 72(4):364-369, 2011.
McKown et al., "Lack of efficacy of oral bovine type II collagen added to existing therapy in rheumatoid arthritis," Arthritis Rheum., 42: 1204-1208, 1999.
Mei, et al., Chemical Industry Press. Biotechnology pharmaceutic preparation: foundation and application: 199, 2004.
Mescher et al., "Signals required for programming effector and memory development by CD8+ T cells," Immunol. Rev., 211: 8I-92, 2006.
Mestas et al., Of mice and not men: Differences between mouse and human immunology. The Journal of Immunology, 172:2731-2738, 2004.
Metzler and Wraith, "Inhibition of experimental autoimmune encephalomyelitis by inhalation but not oral administration of the encephalitogenic peptide: influence of MHC binding affinity," Int. Immunol., 5:1159-1165, 1993.

(56) References Cited

OTHER PUBLICATIONS

Mexican Patent Application No. MX/a/2014/011623 office action dated Jul. 28, 2017.
Miller et al., "The induction of cell-mediated immunity and tolerance with protein antigens coupled to syngeneic lymphoid cells," J. Exp. Med., 149: 758-766, 1979.
Moore et al., Tracking the recruitment of diabetogenic CD8+ T-cells to the pancreas in real time. Diabeters, 53:1459-1466, 2004.
Nakayama et al., "Prime role for an insulin epitope in the development of type 1 diabetes in NOD mice," Nature, 435: 220-224, 2005.
Nelson, J., 6 Types of asthma and how they're treated. J. mnn.com, Nov. 17, 2015, 4 pages.
Oh et al., "IL-15/IL avidity maturation of memory CDS+ T cells," Proc. Natl. Acad. Sci. USA, 101: 15154-15159, 2004.
Oleszak et al., Theiler's Virus Infection: a Model for Multiple Sclerosis, Clinical Microbiology Reviews 17(1 ):174-207, 2004.
Ouyang et al., "Recognition of HLA class I-restricted beta-cell epitopes in type 1 diabetes," Diabetes, 55: 3068-3074, 2006.
Pachner. "Experimental models of multiple sclerosis," Current Opinion in Neurology 24:291-299, 2011.
Packard et al, "COPD is associated with production of autoantibodies to a broad spectrum of self-antigens, correlative with disease phenotype," Immunol Res. 55(1-3):48-57, 2013.
Pakula et al., "Genetic Analysis of Protein Stability and Function," Annu. Rev. Genet. 23:289-310, 1989.
Palmer et al., "Insulin antibodies in insulin-dependent diabetics before insulin treatment," Science, 222: 1337-1339, 1983.
Pascolo et al., "HLA-A2.1-restricted education and cytolytic activity of CD8(+) T lymphocytes from beta2 microglobulin (beta2m) HLA-A2.1 monochain transgenic H-2Db beta2m double knockout mice," J. Exp. Med., 185: 2043, 1997.
Patel et al., Cationic nanoparticles for delivery of CpG oligodeoxynucleotide and ovalbumin: In vitro and in vivo assessment. J. Biomed Nanotechnology, 3(1):97-106, 2007.
PCT/EP2011/066994 International Search Report and Written Opinion dated Nov. 21, 2011.
PCT/EP2011/069931 International Search Report and Written Opinion dated Jul. 10, 2012.
PCT/IB2013/003033 International Search Report and Written Opinion dated Jul. 14, 2014.
PCT/IB2013/052352 International Search Report and Written Opinion dated Oct. 2, 2013.
PCT/IB2014/003014 International Search Report and Written Opinion dated May 12, 2015.
PCT/IB2016/000691 International Search Report and Written Opinion dated Mar. 7, 2017.
PCT/US2008/056279 International Search Report and Written Opinion dated Oct. 22, 2008.
Petros, et al. "Antibody conjugation to PRINT nanoparticles as a cellular targeting strategy," Abstracts of Papers American Chemical Society, 233:COLL 14, 2007.
Pinkse et al., "Autoreactive CDS T cells associated with beta cell destruction in type 1 diabetes," Proc. Nat!. Acad. Sci. USA, 102: 18425-18430, 2005.
Purton, et al. "Antiviral CD4 memory T cells are IL-15 dependent," Journal of Experimental Medicine, 204(4):951-961, 2007.
Ransohoff, R. M., Animal models of multiple sclerosis: the good, the bad and the bottom line, Nature Neuroscience 15(8):1074-1077, 2012.
Riemekasten et al., "Key autoantigens in SLE," Rheumatology (Oxford) 44(8):975-982, 2005.
Routsias et al., "Autoimmune response and target autoantigens in Sjogren's syndrome," Eur J Clin Invest. 40(11):1026-1036, 2010.
Santamaria, "Effector lymphocytes in autoimmunity," Curr. Opin. Immunol., 13: 663-669, 2001.
Santamaria et al., "Beta-cell-cytotoxic CDS+ T cells from nonobese diabetic mice use highly homologous T cell receptor alpha-chain CDR3 sequences," J. Immunol., 154: 2494, 1995.
Santamaria et al., "Characterization of T lymphocytes infiltrating human pancreas allograft affected by isletitis and recurrent diabetes," Diabetes, 41: 53-61, 1992.
Santamaria et al., "Skewed TCR usage and junctional heterogeneity among isletitis ab and gd T cells in human type 1 diabetes," Diabetes, 43: 599-606, 1994.
Saragovi and Burgess, Exp Opin Ther Patents. 1999; 9: 737-751.
Schirle et al. Combining computer algorithms with experimental approaches permits the rapid and accurate identification ofT cell epitopes from defined antigens. J. Immunol. Methods. 257: 1-16:2001.
Schneider et al, "The end of the era of generosity? Global health amid economic crisis," Philos Ethic Humanit Med. 4:1, 2009.
Schreiber, et al. "Using carbon 31-33 magnetic nanoparticles to target, track, and manipulate dendritic cells," Journal of Immunological Methods, 365(1-2):47-59, 2010.
Schutgen et al., "A directional strategy for monitoring ere-mediated recombination and the cellular level in the mouse," Nat. Biotech., 21: 562-566, 2003.
Serreze et al., "Autoreactive diabetogenic T-cells in NOD mice can efficiently expand from a greatly reduced precursor pool," Diabetes, 50: 1992-2000, 2001.
Shanks et al., Are animal models predictive for humans? Philosophy, Ethics, and Humanities in Medicine, 4(2):20 pages, 2009.
Shao et al., "Nanoparticle-Based Immunotherapy for Cancer," ACS Nano 9(1):16-30, 2015.
Shukla et al., "Emerging nanotechnologies for cancer immunotherapy," Exp Bioi Med (Maywood) 241 (10):1116-1126, 2016.
Sibley et al., "Recurrent diabetes mellitus in the pancreas iso- and allograft. A light and electron microscopic and immunohistochemical analysis off our cases," Lab. Invest., 53: 132-144, 1985.
Sollid et al., "Nomenclature and listing of celiac disease relevant gluten T-cell epitopes restricted by HLA-DQ molecules," Immunogenetics 64(6):455-460, 2012.
Somoza et al., "Pancreas in recent onset insulin-dependent diabetes mellitus. Changes in HLA, adhesion molecules and autoantigens, restricted T cell receptor V beta usage, and cytokine profile," J. Immunol., 153:1360-1377, 1994.
Spada et al., Self-recognition of CD1 by y/x T cells: Implications for innate immunity. J. Exp. Med. 191(6): 937-948, 2000.
Sprent and Surh, "T cell memory," Annu. Rev. Immunol., 20: 551-579, 2002.
Sprent and Tough, "T cell death and memory," Science, 293: 245-248, 2001.
Standifer et al., "Identification of novel HLA-A *0201-restricted epitopes in recent-onset type 1 diabetic subjects and antibody-positive relatives," Diabetes, 55:3061-3067, 2006.
Szczerkowska-Dobosz, A. "Human Leukocyte Antigens as Psoriasis Inheritance and Susceptibility Markers," Arch Immunol Ther Exp (Warsz) 53(5):428-433, 2005.
T Hart et al., Modelling of multiple sclerosis: lessons learned in a non-human primate, Lancet Neurology 3: 588-597, 2004.
Tait et al., "HLA antigens and age at diagnosis of insulin-dependent diabetes mellitus," Hum. Immunol., 42:116-124, 1995.
Takahashi et al., Isolation and characterization of a colonic autoantigen specifically recognized by colon tissue bound immunoglobulin G from idiopathic ulcerative colitis. J.Clinical Invest., 76:311-318, 1985.
Takaki et al., "HLA-A *0201-restricted T cells from humanized NOD mice recognize autoantigens of potential clinical relevance to type 1 diabetes," J. Immunol., 176: 3257-3265, 2006.
Tan et al., "Interleukin (IL)-15 and IL-7 jointly regulate homeostatic proliferation of memory phenotype CDS+ cells but are not required for memory phenotype CD4+ cells," J. Exp. Med., 195:1523-1532, 2002.
Tanimura et al., "Beta2-Giycoprotein 1/HLA class II complexes are novel autoantigens in antiphospholipid syndrome," Blood 125(18):2835-2844, 2015.
Toes et al., "Peptide vaccination can lead to enhanced tumor growth through specific T-cell tolerance induction," Proc. Natl. Acad. Sci. USA, 93: 7855-7860, 1996.
Toma et al., "Recognition of a subregion of human proinsulin by class I-restricted T cells in type 1 diabetic patients," Proc. Natl. Acad. Sci. USA, 102: 10581-10585, 2005.

(56) References Cited

OTHER PUBLICATIONS

Trenttham et al., "Effects of oral administration of type II collagen on rheumatoid arthritis," Science, 261:1727-1730, 1993.
Trudeau et al., "Prediction of spontaneous autoimmune diabetes in NOD mice by quantification of auto reactive T cells in peripheral blood," J. Clin. Invest., 111: 217-223, 2003.
Tsai et al., Reversal of autoimmunity by boosting memory-like autoregulatory T cells. Immunity, 32:568-580, 2010.
Tsuchida et al., "Autoreactive CDS+ T-cell responses to human myelin protein-derived peptides," Proc. Nat. Acad. Sci. USA, 91:10859-63, 1994.
Tufveson et al., New immunosuppressants: Testing and development in animal models and the clinic: with special reference to DSG. Immun. Reviews, 136:101-107, 1993.
Unger et al., "Human clonal CDS autoreactivity to an IGRP islet epitope shared between mice and men," Ann. N.Y. A cad. Sci., 1103: 192-195, 2007.
U.S. Appl. No. 15/348,959 First Action Interview Pilot Program, Pre-Interview Communication dated Apr. 13, 2017.
U.S. Appl. No. 12/044,435 Office Action dated Jun. 8, 2011.
U.S. Appl. No. 12/044,435 Office Action dated May 2, 2012.
U.S. Appl. No. 12/044,435 Office Action dated Nov. 24, 2010.
U.S. Appl. No. 12/848,055 Office Action dated Apr. 4, 2012.
U.S. Appl. No. 12/848,055 Office Action dated Aug. 23, 2012.
U.S. Appl. No. 12/848,055 Office Action dated Dec. 19, 2012.
U.S. Appl. No. 12/848,055 Office Action dated Dec. 24, 2014.
U.S. Appl. No. 12/848,055 Office Action dated Jun. 6, 2014.
U.S. Appl. No. 12/848,055 Office Action dated May 13, 2016.
U.S. Appl. No. 13/249,105 Office Action dated Apr. 3, 2015.
U.S. Appl. No. 13/249,105 Office Action dated Nov. 30, 2015.
U.S. Appl. No. 13/249,105 Office Action dated Sep. 8, 2017.
U.S. Appl. No. 13/294,109 Office Action dated Jan. 12, 2015.
U.S. Appl. No. 13/294,109 Office Action dated Jun. 4, 2013.
U.S. Appl. No. 13/294,109 Office Action dated Nov. 13, 2013.
U.S. Appl. No. 13/712,832 Office Action dated Feb. 27, 2015.
U.S. Appl. No. 13/830,521 Office Action dated Jul. 25, 2014.
U.S. Appl. No. 13/830,521 Office Action dated Jun. 28, 2016.
U.S. Appl. No. 13/830,521 Office Action dated Mar. 5, 2015.
U.S. Appl. No. 13/842,302 Office Action dated Apr. 30, 2014.
U.S. Appl. No. 13/842,302 Office Action dated Feb. 18, 2015.
U.S. Appl. No. 13/842,302 Office Action dated Jul. 6, 2016.
U.S. Appl. No. 13/842,302 Office Action dated May 3, 2017.
U.S. Appl. No. 14/684,153 Office Action dated Jun. 30, 2016.
U.S. Appl. No. 14/723,268 Office Action dated Mar. 30, 2016.
U.S. Appl. No. 14/723,268 Office Action dated Oct. 16, 2015.
U.S. Appl. No. 15/348,959 Office Action dated Aug. 30, 2017.
U.S. Appl. No. 15/433,898 Office Action dated Sep. 28, 2017.
Van Belle et al., Type 1 Diabetes: Etiology, Immunology and Therapeutic Strategies, Physiol. Rev. 91:79-118, 2001.
Van Boekel et al., "Autoantibody systems in rheumatoid arthritis: specificity, sensitivity and diagnostic value," Arthritis Res. 4(2):87-93, 2002.
Van Driel et al., "Role of regulatory T cells in gastrointestinal inflammatory disease," Journal of Gastroenterology and Hepatology 23:171-177, 2008.
Vandenbarkk et al., "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," Journal of Immunology 171(1):127-33, 2003.
Verdaguer et al., "Acceleration of spontaneous diabetes in TCR-transgenic nonobese diabetic mice by beta cell-cytotoxic CDS+ T-cells in autoimmunity," Curr. Opin. Immunol., 17: 624-631, 2005.
Verdaguer et al., "Spontaneous autoimmune diabetes in monoclonal T cell nonobese diabetic mice," J. Exp. Med., 186: 1663-1676, 1997.
Verdu et al., Oral administration of antigens from intestinal flora anaerobic bacteria reduces the severity of experimental acute colitis in BALB/c mice. Clin Exp Immunol, 120:46-50, 2000.

Vincent et al.,"Understanding the function of CD1-restricted T cells," Nat. Immunol. 4(6):517-523, 2003.
Wainwright et al., "HLA-F Is a Predominantly Empty, Intracellular, TAP-Associated MHC Class Ib Protein with a Restricted Expression Pattern," J. Immunol. 164(1):319-32S, 2000.
Walter and Santamaria, "CD8+ T cells in autoimmunity," Curr. Opin. Immunol., 17: 624-631, 2005.
Wang, et at. "Induction of Potent CDS T-Cell Responses by Novel Biodegradable nanopartictes carrying Human Immunodeficiency Virus Type 1 gp 120," Journal of Virology, 81(19):10009-10016, 2007.
Warnock et al., Normoglycaemia after transplantation of freshly isolated and cryopreserved pancreatic islets in Type 1 (insulin-dependent) diabetes mellitus. Diabetologia, 34: 55-58, 1991.
Weiner, "Double-blind pilot trial of oral tolerization with myelin antigens in multiple sclerosis," Science, 259: 1321-1324, 1993.
Weiss et al., Covalent HLA-B27/peptide complex induced by specific recognition of an aziridine mimic of arginine. Proc. Natl. Acad. Sci. USA, 93:10945-10948, 1996.
Wekerle et al., Animal models of multiple sclerosis, Drug Discovery Today: Disease Models 3(4):359-367, 2006.
Wen et al., "3. Surface effect of the nanoparticles," Introduction to Nature Science:373-374, 2007.
Williams et al., "Developing and maintaining protective CDS+ memory T cells," Immunol. Rev., 211:146-153, 2006.
Wilson et al., "pH-Responsive Nanoparticle Vaccines for Dual-Delivery of Antigens and Immunostimulatory Oligonucleotides," ASC Nano 7(5):3912-3925, 2013.
Winer et al., "Autoimmune islet destruction in spontaneous type I diabetes is not beta-cell exclusive," Nat. Med., 9:198-205, 2003.
WO2004078909—Bibliographic data page from EPO webiste showing it was also published as US2007154953, downloaded Nov. 15, 2010, 1 page.
Wong et al., "Identification of an MHC class !-restricted autoantigen in type I diabetes by screening an organ-specific eDNA library," Nat. Med., 5:1026-1031, 1999.
Wraith et al., "Antigen recognition in autoimmune encephalomyelitis and the potential for peptide-mediated immunotherapy," Cell, 59: 247-255, 1989.
Wu et al., "Magnetic Iron Oxide Nanoparticles: Synthesis and Surface Functionalization Strategies," Nanoscale Res Lett. 3:397-415, 2008.
Wucherpfennig et al., "Structural basis for major histocompatibility complex (MHC)-linked susceptibility to autoimmunity: charged residues of a single MHC binding pocket confer selective presentation of self-peptides in pemphigus vulgaris," PNAS 92(25):11935-11939, 1995.
Xu, H. "13.3.3 Relationship between gene transduction and nanoparticle size," Nano Medicine:35S, 2004.
Yadav et al., "Recombinant T-Cell Receptor Ligand (RTL) for Treatment of Multiple Sclerosis: A Double-Blind, Placebo-Controlled, Phase 1, Dose-Escalation Study," Autoimmune Diseases 2012(954 739):1-11, 2012.
Yamanouchi et al., "Interleukin-2 gene variation impairs regulatory T cell function and causes autoimmunity," Nat. Genet., 39:329-337, 2007.
Yeste et al., "Nanoparticle-mediated codelivery of myelin antigen and a tolerogenic small molecule suppresses experimental autoimmune encephalomyelitis," PNAS 109(28): 11270-11275, 2012.
Zajac et al., "Viral immune evasion due to persistence of activated T cells without effector function," J. Exp. Med., 188:2205-2213, 1998.
Zhang et al. HMGB1, an innate alarmin, in the pathogenesis of type 1 diabetes. Int J Clin Exp Pathol., 3(1 ):24-38, 2010.
Altman, J.D. et al. Phenotypic Analysis of Antigen-Specific T Lymphocytes. Science 274:94-96, 1996.
Australia Patent Application No. 2016203231 Examination Report No. 2 dated Nov. 30, 2017.
Babbe, H. et al. Clonal expansions of CD8(+) T cells dominate the T cell infiltrate in active multiple sclerosis lesions as shown by micromanipulation and single cell polymerase chain reaction. J. Exp. Med. 192, 393-404, 2000.

(56) References Cited

OTHER PUBLICATIONS

Bacchetta, R. et al. High levels of interleukin 10 production in vivo are associated with tolerance in SCID patients transplanted with HLA mismatched hematopoietic stem cells. J. Exp. Med. 179:493-502, 1994.
Bailey-Bucktrout, S. L. et al. Self-antigen-driven activation induces instability of regulatory T cells during an inflammatory autoimmune response. Immunity 39, 949-962, 2013.
Bakker et al. MHC Multimer Technology: Current Status and Future Prospects. Current Opinion in Immunology, 17(4):428-433, 2005.
Buenafe et al., Regulatory T-cells play a role in T-cell receptor CDR2 peptide regulation of experimental autoimmune encephalomyelitis. Immunology, 135(2):168-179, 2012.
Burke et al., The influence of adjuvant on the therapeutic efficacy of a recombinant genital herpes vaccine. J. Inf. Dis., 170:1110-1119, 1994.
Burton, B.R. et al. Sequential transcriptional changes dictate safe and effective antigen-specific immunotherapy. Nature Commun. 5:4741-4747, 2014.
Caruso et al., Investigation of electrostatic interactions in polyelectrolyte multilayer films: Binding of anionic fluorescent probes to layers assembled onto colloids. Macromolecules, 32(7):2317-2328, 1999.
Caruso et al., Protein multilayer formation on colloids through a stepwise self-assembly technique. J.Amer. Chem. Soc., 121(25):6039-6046, 1999.
Chen, et al., IL-2 controls the stability of Foxp3 expression in TGF-beta-induced Foxp3+ T cells in vivo. J. Immunol. 186:6329-6337, 2011.
Cirillo et al, "S1OOB protein in the gut: The evidence for enteroglial-sustained intestinal inflammation," World J Gastroenterol. 17(10):1261-1266, 2011.
Colombia Patent Application No. NC2017/0011437 Office Action dated Nov. 19, 2017.
Davies, Engineered particle surfaces. Advanced Materials, 10(15):1264-1270, 1998.
Desreumaux, P. et al. Safety and Efficacy of Antigen-Specific Regulatory T-Cell Therapy for Patients With Refractory Crohn's Disease. Gastroenterology 143:1207-1217, 2012 (Abstract only).
Edelman, Gerald M. et al. The covalent structure of an entire yGimmunoglobulin molecule. PNAS, 63(1):78-85, 1969.
Eggena et al., "Identification of Histone H1 as a Cognate Antigen of the Ulcerative Colitisassociated Marker Antibody pANCA," Journal of Autoimmunity 14:83-97, 2000.
Reijonen, H. et al. Detection of GAD65-specific T-cells by major histocompatibility complex class II tetramers in type 1 diabetic patients and at-risk subjects. Diabetes 51:1375-1382, 2002.
Ellman et al., Biosynthetic method for introducing unnatural amino acids site-specifically into proteins. Meth. Enzym. 202:301-336, 1991.
European Patent Application No. 13856460.4 Communication dated Nov. 15, 2017.
European Patent Application No. 17173410.61 extended European Search Report dated Dec. 15, 2017.
Firestein, G. S. Evolving concepts of rheumatoid arthritis. Nature 423:356-361, 2003.
Gagliani, et al. Coexpression of CD49b and LAG-3 identifies human and mouse T regulatory type 1 cells. Nat. Med. 19:739-746, 2013 (Abstract only).
Garboczi, et al. HLA-A2-peptide complexes: Refolding and crystallization of molecules expressed in *Escherichia coli* and complexed with single antigenic peptides. Proc Natl Acad Sci USA 89:3429-3433, 1992.
GenBank accession No. NM_001008228.2.
GenBank accession No. NP_001008229.1.
Getts, et al. Microparticles bearing encephalitogenic peptides induce T-cell tolerance and ameliorate experimental autoimmune encephalomyelitis. Nature Biotechnol. 30:1217-1224, 2012.
Gill et al., Characterization of primary T cell subsets mediating rejection of pancreatic islet grafts. Journal of Immunology, 143(7):2176-2178, 1989.

Giuliani et al,. Additive effect of the combination of glatiramer acetate and minocycline in a model of MS. J. Neuroimmunol. 158:213-221, 2005.
Gong, et al "Immobilized MHC class I chain-related protein A synergizes with IL-15 and soluble 4-1BB ligand to expand NK cells with high cytotoxicity ex vivo," Cellular & Molecular Immunology, 7(6)477-484, 2010.
Gunn et al., "A multimodal targeting nanoparticle for selectively labeling T cells," Small. 4(6):712-715, 2008.
Gupta et al., "Synthesis and surface engineering of iron oxide nanoparticles for biomedical applications," Biomaterials 26:3995-4021, 2005.
Hale, et al. Distinct memory CD4+ T cells with commitment to T follicular helper- and T helper 1-cell lineages are generated after acute viral infection. Immunity 38:805-817, 2013.
Hall et al., Mapping labeled sites in *Escherichia coli* ribosomal RNA: Distribution of methyl groups and identification of a a photoaffinity-labeled RNA region putatively at the Peptidyltransferase center. Biochemistry 24:5702-5711, 1985.
Hanprasopwattana, Titania coatings on monodisperse silica spheres (Characterization using 2-propanol dehydration and TEM). Langmuir, 12:3173-3179, 1996.
Holgate et al., "Treatment strategies for allergy and asthma," Nature 8:218-230, 2008.
Holst, J. et al. Generation of T-cell receptor retrogenic mice. Nat. Protoc. 1:406-417, 2006.
Israel Patent Application No. 249165 Office Action dated Dec. 17, 2017.
Japanese Patent Application No. 2016-159414 Office Action dated Oct. 30, 2017.
Jokerst et al., Nanoparticle PEGylation for imaging and therapy. Nanomedicine, 6(4):715-728, 2011.
Kamanaka, M. et al. Expression of interleukin-10 in intestinal lymphocytes detected by an interleukin-10 reporter knockin tiger mouse. Immunity 25:941-952, 2006.
Komatsu, N. et al. Heterogeneity of natural Foxp3+ T cells: a committed regulatory T-cell lineage and an uncommitted minor population retaining plasticity. Proc. Natl. Acad. Sci. U.S.A. 106:1903-1908, 2009.
Komatsu, N. et al. Pathogenic conversion of Foxp3+ T cells into TH17 cells in autoimmune arthritis. Nat. Med. 20:62-68, 2014.
Krishnamoorthy et al., "Myelin-specific T cells also recognize neuronal autoantigen in a transgenic mouse model of multiple sclerosis," Nature Medicine 15(6):626-633, 2009.
Kulmala, P. "Prediabetes in Children," Pediatr Drugs, 5(4):211-221, 2003.
Leavenworth et al., Amelioration of arthritis through mobilization of peptide-specific CD8+ regulatory T cells. J. Clin. Invest. 123:1382-1389, 2013.
Marwaha, A. K. et al. Cutting edge: Increased IL-17-secreting T cells in children with new-onset type 1 diabetes. J. Immunol. 185:3814-3818, 2010.
McClymont, S. A. et al. Plasticity of human regulatory T cells in healthy subjects and patients with type 1 diabetes. J. Immunol. 186:3918-3926, 2011.
McLarnon, A. Regulatory T-cell therapy is a safe and well-tolerated potential approach for treating refractory Crohn's disease. Nature Rev. Gastroenterol. Hepatol. 9:559, 2012.
Merchant et al., An efficient route to human bispecific IgG. Nature Biotechnology, 16:677-681, 1998.
Mestas and Hughes, Of mice and not men: Differences between mouse and human immunology. J. of Immunology, 172:2731-2738, 2004.
Miyara, M. et al. Functional delineation and differentiation dynamics of human CD4+ T cells expressing the FoxP3 transcription factor. Immunity 30:899-911, 2009.
Moore et al., Tracking the recruitment of diabetogenic CD8+ T-cells to the pancreas in real time. Diabetes, 53(6):1459-1466, 2004.
Mukherjee, R. et al. Identification of CD4+ T cell-specific epitopes of islet-specific glucose-6-phosphatase catalytic subunit-related protein: A novel Beta cell autoantigen in Type 1 diabetes. J. Immunol. 174:5306-5315, 2005.

(56) References Cited

OTHER PUBLICATIONS

Musacchio, et al. PEG-PE micelles loaded with Paclitaxel and surface-modified by a PBR-ligand: Synergistic anticancer effect. Mol Pharm 6:468-479, 2009.
Nelson et al. "6 types of asthma and how they're treated," Mother Nature Network, mnn.com. 2015.
New Zealand Patent Application No. 706970 First Examination Report dated Nov. 8, 2017.
Noren et al. A general method for site-specific incorporation of unnatural amino acids into proteins. Science 244(4901):182-188, 1989.
Oleszak et al., "Theiler's Virus Infection: a Model for Multiple Sclerosis," Clinical Microbiology Reviews 17(1):174-207, 2004.
Onoda, T. et al. Human CD4+ central and effector memory T cells produce IL-21: effect on cytokine-driven proliferation of CD4+ T cell subsets. Int. Immunol. 19:1191-1199, 2007.
Partch and Brown, Aerosol and solution modification of particle-polymer surfaces. J. Adhesion, 67:259-276, 1998.
PCT/IB2016/000691 International Preliminary Report on Patentability dated Nov. 7, 2017.
Pekarek et al., Double-walled polymer microspheres for controlled drug release. Nature, 367:258-260, 1994.
Perrault, S.D. et al. Mediating tumor targeting efficiency of nanoparticles through design. Nano Lett, 9(5):1909-1915, 2009.
Ponder and Richards, Tertiary templates for proteins. Use of packing criteria in the enumeration of allowed sequences for different structural classes. J. Mol. Biol. 193:775-791, 1987.
Pot, C. et al. Cutting edge: IL-27 induces the transcription factor c-Maf, cytokine IL-21, and the costimulatory receptor ICOS that coordinately act together to promote differentiation of IL-10-producing TR1 cells. J. Immunol. 183:797-801, 2009.
Ransohoff et al., "Animal models of multiple sclerosis: the good, the bad and the bottom line," Nature Neuroscience 15(8):1074-1077, 2012.
Roncarolo, et al., Clinical tolerance in allogeneic hematopoietic stem cell transplantation. Immunol. Rev. 241:145-163, 2011.
Roncarolo, et al. Interleukin-10-secreting type 1 regulatory T cells in rodents and humans. Immunol. Rev. 21:28-50, 2006.
Russia Patent Application No. 2015116509 Office Action dated Nov. 29, 2017.
Russia Patent Application No. 2014141984 second Office Action dated Nov. 23, 2017.
Sakaguchi, S. et al. Foxp3+ CD25+ CD4+ natural regulatory T cells in dominant self-tolerance and autoimmune disease. Immunol. Rev. 212:8-27, 2006.
Santamaria, P. The long and winding road to understanding and conquering type 1 diabetes. Immunity 32:437-445, 2010.
Saraiva, M. et al. Interleukin-10 production by Th1 cells requires interleukin-12-induced STAT4 transcription factor and ERK MAP kinase activation by high antigen dose. Immunity 31:209-219, 2009.
Sato, K. et al. Marked induction of c-Maf protein during Th17 cell differentiation and its implication in memory Th cell development. J. Biol. Chem. 286:14963-14971, 2011.
Schirle et al., "Combining computer algorithms with experimental approaches permits the rapid and accurate identification of T cell epitopes from defined antigens," J. Immunol. Methods 257:1-16, 2001.
Scott et al., "Synthesis, Characterization, and Applications of Dendrimer-Encapsulated Nanoparticles". The Journal of Physical Chemistry B (109):692-704, 2005.
Shanke et al., Are animal models predictive for humans? Philosophy, Ethics, and Humanities in Medicine, 9:1-20, 2007.
Spensieri, F. et al. Human circulating influenza-CD4+ ICOS1+IL-21+ T cells expand after vaccination, exert helper function, and predict antibody responses. Proc. Natl. Acad. Sci. U.S.A. 110:14330-14335, 2013.

Stratmann, T. et al. Susceptible MHC alleles, not background genes, select an autoimmune T cell reactivity. J. Clin. Invest. 112:902-914, 2003.
Stratmann, T. et al. The I-Ag7 MHC class II molecule linked to murine diabetes is a promiscuous peptide binder. J. Immunol. 165:3214-3225, 2000.
Sukhorukov et al., Stepwise polyelectrolyte assembly on particle surfaces: a novel approach to colloid design. Polymers Adv. Tech., 9(10-11):759-767, 1998.
T Hart et al., "Modelling of multiple sclerosis: lessons learned in a non-human primate," Lancet Neurology 3:588-597, 2004.
Tigges et al., Human herpes simplex virus (HSV)-specific CD8+ CTL clones recognize HSV-2-infected fibroblasts after treatment with IFN-gamma or when virion host shutoff functions are disabled. J. Immunol., 156(10):3901-3910, 1996.
Tsai, et al., CD8+ T-cells in autoimmune diabetes. Adv. Immunol. 100:79-124, 2008.
Tufveson, et aL, "New Immunosuppressants: Testing and Development in animal models and the clinic with special reference to DSG", Immunological Reviews, 136:101-•107, 2009.
UniProtKB: D4VD94. from www.uniprot.org/uniprot!D4VD94. 2010.
Vakil, R. et al. Effect of cholesterol on the release of amphotericin B from PEG-phospholipid micelles. Mol Pharm 5:98-104, 2008.
Van Belle, Type 1 Diabetes: Etiology, Immunology, and Therapeutic Strategies. Physiol Rev. 91:79-118, 2011.
Verdu et al., "Oral administration of antigens from intestinal flora anaerobic bacteria reduces the severity of experimental acute colitis in BALB/c mice," Clin Exp Immunol. 120:46-50, 2000.
Wang, J. et al. In situ recognition of autoantigen as an essential gatekeeper in autoimmune CD8+ T cell inflammation. Proc. Natl. Acad. Sci. U.S.A. 107: 9317-9322, 2010.
Wekerle et al., "Animal models of multiple sclerosis," Drug Discovery Today: Disease Models 3(4):359-367, 2006.
Xu and Sun, Mini Review: Monodisperse magnetic nanoparticles for biomedical applications. Polymer International 56:821-826, 2007.
Yang, J. et al. CD4+ T cells from type 1 diabetic and healthy subjects exhibit different thresholds of activation to a naturally processed proinsulin epitope. J. Autoimmun. 31:30-41, 2008.
Yang, J. et al. Islet-specific glucose-6-phosphatase catalytic subunit-related protein-reactive CD4+ T cells in human subjects. J. Immunol. 176:2781-2789, 2006.
Yang, X. P. et al. Opposing regulation of the locus encoding IL-17 through direct, reciprocal actions of STAT3 and STAT5. Nat. Immunol. 12, 247-25, 2011.
Yoshida, K. et al. Evidence for shared recognition of a peptide ligand by a diverse panel of non-obese diabetic mice-derived, islet-specific, diabetogenic T cell clones. Int. Immunol. 14:1439-1447, 2002.
Yoshizaki, A. et al. Regulatory B cells control T-cell autoimmunity through IL-21-dependent cognate interactions. Nature 491:264-268, 2012.
Yu, et al. Cutting edge: Single-chain trimers of MHC Class 1 molecules form stable structures that potentially stimulate antigen-specific T cells and B cells. J Immunol 168:3145-3149, 2002.
Zang, Y. C. et al. Increased CD8+ cytotoxic T cell responses to myelin basic protein in multiple sclerosis. J. Immunol. 172:5120-5127, 2004.
Zhang et al., "HMGB1, an innate alarmin, in the pathogenesis of type 1 diabetes," Int. J. Clin. Exp. Pathol. 3(1 ):24-38, 2010.
Zhou, et al., Plasticity of CD4+ T cell lineage differentiation. Immunity 30:646-655, 2009.
Zhou, X. et al. Instability of the transcription factor Foxp3 leads to the generation of pathogenic memory T cells in vivo. Nat. Immunol. 10:1000-1007, 2009.
U.S. Appl. No. 15/348,959 Office Action dated Jan. 12, 2018.
Peng et al. Synthesis and characterization of monodisperse hollow Fe3O4 nanoparticles. Angew Chem 119:4233-4236 (2007).

* cited by examiner

METHODS AND COMPOSITIONS FOR SUSTAINED IMMUNOTHERAPY

CROSS-REFERENCE TO RELATED APPLICATION

This application claims priority under 35 U.S.C. § 119(e) to U.S. Provisional Patent Application No. 61/899,826, filed Nov. 4, 2013, the entire content of which is hereby incorporated by reference into the present disclosure.

SEQUENCE LISTING

The instant application contains a Sequence Listing which has been submitted electronically in ASCII format and is hereby incorporated by reference in its entirety. Said ASCII copy, created on Dec. 5, 2014, is named 378701-0651 SL.txt and is 11,629 bytes in size.

FIELD OF DISCLOSURE

This disclosure is directed to compositions and methods related to immunotherapy and medicine.

BACKGROUND

Throughout and within this disclosure are technical and patent publications, referenced by an identifying citation or by an Arabic number. The full bibliographic citation corresponding to the Arabic number is found in the specification, preceding the claims. The disclosures of all references cited herein are incorporated by reference into the present application to more fully describe the state of the art to which this invention pertains.

Autoimmune diseases are caused by an attack of self-tissues by the immune system. An ideal therapy would be one capable of selectively blunting the autoimmune response (against all antigenic epitopes targeted in that disease) without impairing systemic immunity (immune responses to foreign antigens). Unfortunately, the lymphocyte specificities involved in any one autoimmune disease are many and incompletely defined, making this a challenging goal.

SUMMARY

In response to this need in the art, described herein are therapeutic compositions useful in treating autoimmune disorders. One aspect relates to a method for expanding and/or developing populations of anti-pathogenic autoreactive T cells and/or B-cells in a subject in need thereof, which method comprises, or consists essentially of, or yet further consists of, administering to that subject an antigen-MHC class II-nanoparticle ("NP") complex ("NP-complex"), wherein the antigen is an autoimmunity related antigen or autoantigen. In some aspects all the antigens on the particular NP are identical or they can be different. In another aspect, the antigens on the NP have different amino acid sequences but are isolated from the same antigenic protein. In a further aspect, the antigens on the NP are from different antigens. In another aspect, the MHCII are the same or different.

In one aspect, this disclosure provides a NP-complex comprising, or alternatively consisting essentially of, or yet further consisting of, a nanoparticle; a MHC class II protein and a disease-relevant antigen that can be in the form of an antigen/MHCII complex, for use in expanding and/or developing one or more populations of B-regulatory cells and TR1 cells (e.g., TR1 and CD4+ cells), in a subject, wherein the nanoparticle has a diameter selected from the group of: from about 1 nm to about 100 nm in diameter; from about 1 nm to about 50 nm in diameter or from about 1 nm to about 20 nm or from about 5 nm to about 20 nm in diameter and the ratio of the number of antigen-MHCII complexes to nanoparticles is from about 10:1 to about 1000:1. In one aspect, the complex has a MHC class II density from about 0.05 pMHCII/100 nm$^2$ NP surface area (including coating) to about 25 pMHCII/100 nm$^2$ NP surface area (including coating). The antigen is an autoantigen involved in an autoimmune response or mimic thereof such as, for example, pre-diabetes, diabetes, multiple sclerosis ("MS") or a multiple sclerosis-related disorder, and optionally wherein when the disease is pre-diabetes or diabetes, the autoantigen is an epitope from an antigen expressed by pancreatic beta cells or the autoantigen IGRP, Insulin, GAD or IA-2 protein. In another aspect, the MHC class II component comprises all or part of a HLA-DR, HLA-DQ, or HLA-DP. The antigen-MHC class II complex is covalently or non-covalently linked to the nanoparticle. The nanoparticle can be bioabsorbable and/or biodegradable.

In a further aspect, the nanoparticle is non-liposomal and/or has a solid core, preferably a gold or iron oxide core. When covalently linked, the antigen-MHC class II complex is covalently linked to the nanoparticle through a linker less than 5 kD in size. In one aspect, the linker comprises polyethylene glycol (PEG). The pMHC can be linked to the nanoparticle or the nanoparticle coating by any structure, including but not limited to linkers or by cross-linking. In one aspect, the MHC is linked to the nanoparticle or the coating directionally through the C-terminus.

Applicant has discovered that the density of the antigen-MHC class II complexes on the nanoparticle contributes to the therapeutic benefit. Thus as disclosed herein, the antigen-MHCII nanoparticle complex can have a defined density in the range of from about 0.05 MHC molecules per 100 nm$^2$ of surface area of the nanoparticle (the surface area measured to include any coating), assuming at least 2 MHCII, or alternatively at least 8, or alternatively at least 9, or alternatively at least 10, or alternatively at least 11, or alternatively at least 12, MHCII complexed to the nanoparticle. In one aspect the complex has a density of MHCII from about 0.01 MHCII per 100 nm$^2$ (0.05 MHCII/100 nm$^2$) to about 30 MHCII/100 nm$^2$, or alternatively from 0.1 MHCII/100 nm$^2$ to about 25 MHCII/100 nm$^2$, or alternatively from about 0.3 MHCII/100 nm$^2$ to about 25 MHCII/100 nm$^2$, or alternatively from about 0.4 MHCII/100 nm$^2$ to about 25 MHCII/100 nm$^2$, or alternatively from about 0.5 MHCII/100 nm$^2$ to about 20 MHCII/100 nm$^2$, or alternatively from 0.6 MHCII/100 nm$^2$ to about 20 MHCII/100 nm$^2$, or alternatively from about 1.0 MHCII/100 nm$^2$ to about 20 MHCII/100 nm$^2$, or alternatively from about 5.0 MHCII/100 nm$^2$ to about 20 MHCII/100 nm$^2$, or alternatively from about 10.0 MHCII/100 nm$^2$ to about 20 MHCII/100 nm$^2$, or alternatively from about 15 MHCII/100 nm$^2$ to about 20 MHCII/100 nm$^2$, or alternatively at least about 0.5, or alternatively at least about 1.0, or alternatively at least about 5.0, or alternatively at least about 10.0, or alternatively at least about 15.0 MHCII/100 nm$^2$, the nm$^2$ surface area of the nanoparticle to include any coating. In one aspect, when 9 or at least 9 MHCII are complexed to a nanoparticle, the density range is from about 0.3 MHCII/100 nm$^2$ to about 20 MHCII/100 nm$^2$.

This disclosure also provides a composition comprising a therapeutically effective amount of the NP-complex as described herein and a carrier, e.g., a pharmaceutically acceptable carrier. In one aspect, all NP-complexes in the composition are identical. In another aspect, the NP-complexes of the composition include diverse or different MHC-antigen complexes.

Methods to make the complexes and compositions are further provided herein. The method can comprise, or alternatively consist essentially of, or yet further consist of, non-covalently coating or covalently complexing antigen-MHC complexes (e.g., MHCII complexes) onto a nanoparticle.

Medical and diagnostic methods are also provided. In one aspect, a method is provided for promoting the formation, expansion and recruitment of B-regulatory cells and/or TR1 cells (e.g., TR1 and CD4+ cells) in an antigen-specific manner in a subject in need thereof, comprising, or alternatively consisting essentially of, or yet further consist of, administering to the subject an effective amount of the NP-complex or composition as described herein.

In another aspect, a method for treating or preventing an autoimmune disease or disorder as described herein, e.g., MS, a MS-related disorder, diabetes or pre-diabetes, in a subject in need thereof is provided, the method comprising, or alternatively consisting essentially of, or yet further consisting of, administering to the subject an effective amount of the NP-complex or composition as described herein, wherein the autoantigen is disease-relevant for the disease to be treated, e.g., for the prevention or treatment of diabetes, the antigen is a diabetes-relevant antigen. In a further aspect, the autoimmune disease is MS or a MS-related disorder and the antigen is MS-relevant.

Kits are also provided. The kits comprise, or alternatively consist essentially of, or yet further consist of a NP-complex as described herein or a composition and instructions for use.

In one aspect, provided herein is a method of making nanoparticles comprising thermally decomposing or heating a nanoparticle precursor. In one embodiment, the nanoparticle is a metal or a metal oxide nanoparticle. In one embodiment, the nanoparticle is an iron oxide nanoparticle. In one embodiment, the nanoparticle is a gold nanoparticle. In one embodiment, provided herein are the nanoparticles prepared in accordance with the present technology. In one embodiment, provided herein is a method of making iron oxide nanoparticles comprising a thermal decomposition reaction of iron acetyl acetonate. In one embodiment, the iron oxide nanoparticle obtained is water-soluble. In one aspect, iron oxide nanoparticle is suitable for protein conjugation. In one embodiment, the method comprises a single-step thermal decomposition reaction.

In one aspect, the thermal decomposition occurs in the presence of functionalized PEG molecules. Certain non-limiting examples of functionalized PEG linkers are shown in Table 1.

In one aspect, the thermal decomposition comprises heating iron acetyl acetonate. In one embodiment, the thermal decomposition comprises heating iron acetyl acetonate in the presence of functionalized PEG molecules. In one embodiment, the thermal decomposition comprises heating iron acetyl acetonate in the presence of benzyl ether and functionalized PEG molecules.

Without being bound by theory, in one embodiment, functionalized PEG molecules are used as reducing reagents and as surfactants. The method of making nanoparticles provided herein simplifies and improves conventional methods, which use surfactants that are difficult to be displaced, or are not displaced to completion, by PEG molecules to render the particles water-soluble. Conventionally, surfactants can be expensive (e.g., phospholipids) or toxic (e.g., Oleic acid or oleilamine). In another aspect, without being bound by theory, the method of making nanoparticles obviates the need to use conventional surfactants, thereby achieving a high degree of molecular purity and water solubility.

In one embodiment, the thermal decomposition involves iron acetyl acetonate and benzyl ether and in the absence of conventional surfactants other than those employed herein.

In one embodiment, the temperature for the thermal decomposition is about 80 to about 300° C., or about 80 to about 200° C., or about 80 to about 150° C., or about 100 to about 250° C., or about 100 to about 200° C., or about 150 to about 250° C., or about 150 to about 250° C. In one embodiment, the thermal decomposition occurs at about 1 to about 2 hours of time.

In one embodiment, the method of making the iron oxide nanoparticles comprises a purification step, such as by using MILTENYI Biotec LS magnet column.

In one embodiment, the nanoparticles are stable at about 4° C. in phosphate buffered saline (PBS) without any detectable degradation or aggregation. In one embodiment, the nanoparticles are stable for at least 6 months.

In one aspect, provided herein is a method of making nanoparticle complexes comprising contacting pMHC with iron oxide nanoparticles provided herein. Without being bound by theory, pMHC encodes a Cysteine at its carboxy-terminal end, which can react with the maleimide group in functionalized PEG at about about pH 6.2 to about pH 6.5 for about 12 to about 14 hours.

In one aspect, the method of making nanoparticle complexes comprises a purification step, such as by using MILTENYI Biotec LS magnet column.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a schematic of a single-chain pMHC-class I expression construct (top) and a representative flow cytometric profile of the binding of the corresponding pMHC tetramer (fluorochrome-labeled) to cognate CD8+ T-cells. FIG. 1A discloses "6xHis" as SEQ ID NO: 70. FIG. 1B is a schematic showing the linkers and two dimensional structure of NP-complexes. As can be seen, one NP can contain the same antigen complexed to the nanoparticle core through various chemical linkers. FIG. 1B discloses "6xHis" as SEQ ID NO: 70. FIG. 1C shows maleimide-functionalized NPs conjugated to NPs.

FIG. 2 discloses "6xHis" as SEQ ID NO: 70.

FIG. 3A shows individual mouse blood glucose curves. Mice were considered 'cured' when stably normoglycemic for 4 wk, after which treatment was withdrawn. HEL$_{14-22}$, a foreign antigen, was used as control. FIG. 3B shows incidence of disease reversal.

FIG. 9 shows ability of $IGRP_{4-22}/IA^{g7}$-NPs to restore normoglycemia (top), expand cognate Tr1 cells (bottom left) and suppress autoantigen presentation in the PLNs (to $IGRP_{206-214}$-reactive CD8+ T-cells; bottom right) of mice treated with cytokine blocking antibodies ("Abs"). Anti-IL10 and anti-TGFβ Abs partially restore autoantigen presentation and inhibit the therapeutic effect of pMHC-NPs, without impairing Tr1 cell expansion.

FIG. 10A shows that pMHC-NP-treated NOD mice can readily clear an acute viral (vaccinia virus) infection (bottom, compare day 4 versus day 14 after infection) despite systemic expansion of autoregulatory Tr1 CD4+ T-cells (top). FIG. 10B shows that pMHC-NP-treated mice (10 doses) can mount antibody responses against KLH-DNP upon immunization in CFA, as compared to untreated and unvaccinated mice.

FIG. 12A is a cartoon depicting the different chemistries that can be used to covalently coat pMHCs onto functionalized, biocompatible iron oxide NPs. FIG. 12B is a transmission electron micrograph of pMHC-coated NPs. FIG. 12C shows Dynamic Light Scattering profiles of pMHC-coated vs. uncoated NPs.

In FIG. 13A, 1:1 mixtures of PKH26-labeled/pulsed with 2.5mi peptide B-cells (bottom) (or dendritic cells, top) plus CFSE-labeled/GPI peptide-pulsed B-cells (bottom) (or dendritic cells, top) were injected into 2.5mi/IAg7-NP-treated NOD mice. Seven days later, the hosts were analyzed for presence of both subsets of B-cells (bottom) or dendritic cells (top). Left panels show representative results and Right histograms show a summary of the results obtained over several experiments. The data indicate that 2.5mi-peptide-pulsed B-cells (but not DCs) expand in 2.5mi/IAg7-NP-treated NOD mice. In B (left panel), Applicant compared the B-cell content in the pancreatic (PLN) and mesenteric (MLN) lymph nodes of NOD mice treated with 2.5mi/IAg7-NPs versus NPs coated with control (diabetes-irrelevant) pMHC-NPs. Data show increased recruitment of B-cells in the former. In B (right panel), Applicant compared the recruitment of B-cells to the PLNs as a function of Tr1 cell recruitment. Data were obtained using several different pMHC-NP preparations. Data show a statistically-significant correlation between recruitment of pMHC-NP-expanded TR1 cells and B-cell recruitment to the PLNs. In FIG. 13B, Applicant transferred B-cells, pulsed with 2.5mi or control peptides, from IL10-eGFP knock-in NOD mice into several different donor mouse types (top labels). After 7 days, spleens were analyzed for conversion of the transfused B-cells into IL10-producing (eGFP+) B-cells expressing high levels of CD1d and CD5 (B-regulatory cells). Data show robust expansion and conversion of cognate (2.5mi-loaded) B-cells into B-reg cells only in 2.5mi/IAg7-NP-treated hosts.

DETAILED DESCRIPTION

Figure 1A:
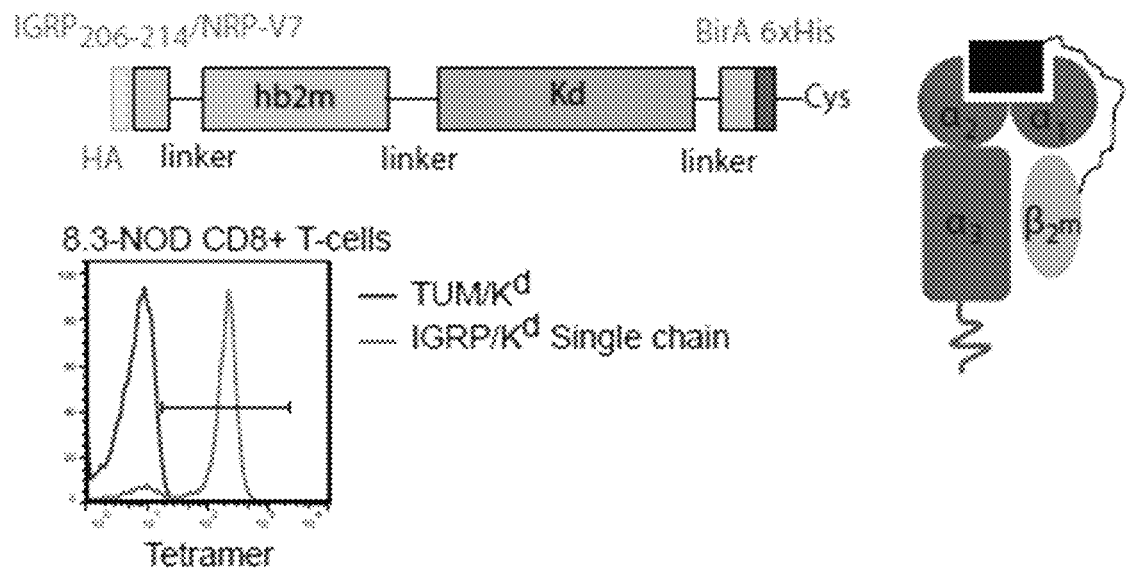
FIGS. 1A-1C show schematics of NP-complexes.
Figure 1B:
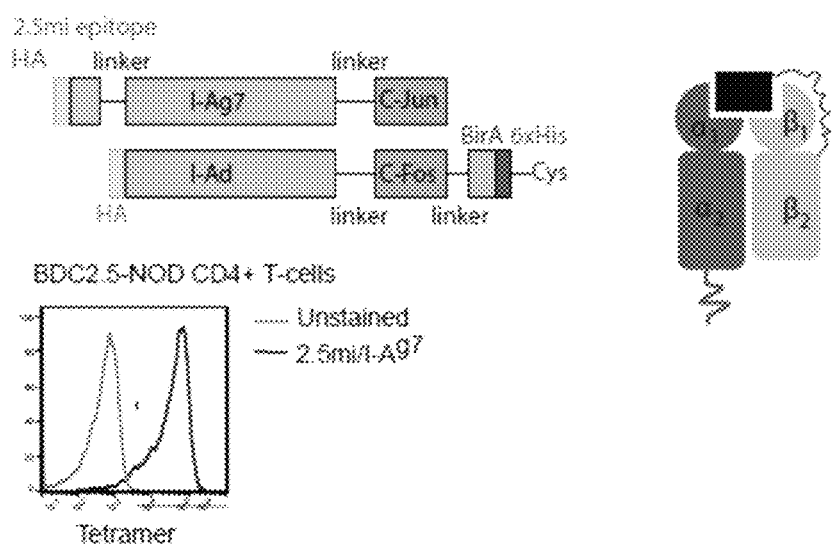

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

I. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel character-istic(s) of the claimed invention, such as compositions for treating or preventing multiple sclerosis. "Consisting of" shall mean excluding more than trace elements of other ingredients and substantial method steps. Embodiments defined by each of these transition terms are within the scope of this invention.

An "auto-reactive T cell" is a T cell that recognizes an "auto-antigen", which is a molecule produced and contained by the same individual that contains the T cell.

A "pathogenic T cell" is a T cell that is harmful to a subject containing the T cell. Whereas, a non-pathogenic T cell is not substantially harmful to a subject, and an anti-pathogenic T cells reduces, ameliorates, inhibits, or negates the harm of a pathogenic T cell.

As used herein the terms regulatory B-cells or B-regulatory cells ("B-regs") intend those cells that are responsible for the anti-inflammatory effect, that is characterized by the expression of CD1d, CD5 and the secretion of IL-10. B-regs are also identified by expression of Tim-1 and can be induced through Tim-1 ligation to promote tolerance. The ability of being B-regs was shown to be driven by many stimulatory factors such as toll-like receptors, CD40-ligand and others. However, full characterization of B-regs is ongoing. B-regs also express high levels of CD25, CD86, and TGF-β. This subset of B cells is able to suppress Th1 proliferation, thus contributing to the maintenance of self-tolerance. The potentiation of B-reg function should become the aim of many immunomodulatory drugs, contributing to a better control of autoimmune diseases. See for example:_ncbi.nlm.nih.gov/pubmed/23707422, last accessed on Oct. 31, 2013.

T Regulatory 1 cells (Tr1) are a subset of CD4+ T cells that have regulatory properties and are able to suppress antigen-specific immune responses in vitro and in vivo. These T-regulatory 1 (Tr1) cells are defined by their unique profile of cytokine production and make high levels of IL-10 and TGF-beta, but no IL-4 or IL-2. The IL-10 and TGF-beta produced by these cells mediate the inhibition of primary naive T cells in vitro. There is also evidence that Tr1 cells exist in vivo, and the presence of high IL-10-producing CD4(+) T cells in patients with severe combined immunodeficiency who have received allogeneic stem-cell transplants have been documented. Tr1 cells are involved in the regulation of peripheral tolerance and they could potentially be used as a cellular therapy to modulate immune responses in vivo. See for example: ncbi.nlm.nih.gov/pubmed/10887343, last accessed on Oct. 31, 2013.

Type-1 T regulatory (Tr1) cells are defined by their ability to produce high levels of IL-10 and TGF-beta. Tr1 cells specific for a variety of antigens arise in vivo, but may also differentiate from naive CD4+ T cells in the presence of IL-10 in vitro. Tr1 cells have a low proliferative capacity, which can be overcome by IL-15. Tr1 cells suppress naive and memory T helper type 1 or 2 responses via production of IL-10 and TGF-beta. Further characterization of Tr1 cells at the molecular level will define their mechanisms of action and clarify their relationship with other subsets of Tr cells. The use of Tr1 cells to identify novel targets for the development of new therapeutic agents, and as a cellular therapy to modulate peripheral tolerance, can be foreseen. See for example, ncbi.nlm.nih.gov/pubmed/11722624, last accessed on Oct. 31, 2013.

The terms "inhibiting," "reducing," or "prevention," or any variation of these terms, when used in the claims and/or the specification includes any measurable decrease or complete inhibition to achieve a desired result.

Throughout this application, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 10%, 5%, or 1%.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, will be used preferentially. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to nanoparticles made from materials which undergo bioabsorption in vivo over a period of time such that long term accumulation of the material in the patient is avoided. In a preferred embodiment, the biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the nanoparticles used in this invention. In one embodiment, iron oxide and a biocompatible, bioabsorbable polymer can be combined. For example, iron oxide and PGLA can be combined to form a nanoparticle.

An antigen-MHC-nanoparticle complex ("NP-complex") refers to presentation of a peptide, carbohydrate, lipid, or other antigenic segment, fragment, or epitope of an antigenic molecule or protein (i.e., self peptide or autoantigen) on a surface, such as a biocompatible biodegradable nanosphere. "Antigen" as used herein refers to all, part, fragment, or segment of a molecule that can induce an immune response in a subject or an expansion of anti-pathogenic cells.

A "mimic" is an analog of a given ligand or peptide, wherein the analog is substantially similar to the ligand. "Substantially similar" means that the analog has a binding profile similar to the ligand except the mimic has one or more functional groups or modifications that collectively accounts for less than about 50%, less than about 40%, less than about 30%, less than about 20%, less than about 10%, or less than about 5% of the molecular weight of the ligand.

The term "anti-pathogenic autoreactive T cell" refers to a T cell with anti-pathogenic properties (i.e., T cells that counteract an autoimmune disease such as MS, a MS-related disease or disorder, or pre-diabetes). These T cells can include anti-inflammatory T cells, effector T cells, memory T cells, low-avidity T cells, T helper cells, autoregulatory T cells, cytotoxic T cells, natural killer T cells, TR1 cells, CD4+ T cells, CD8+ T cells and the like.

The term "anti-inflammatory T cell" refers to a T cell that promotes an anti-inflammatory response. The anti-inflammatory function of the T cell may be accomplished through production and/or secretion of anti-inflammatory proteins, cytokines, chemokines, and the like. Anti-inflammatory proteins are also intended to encompass anti-proliferative signals that suppress immune responses. Anti-inflammatory proteins include IL-4, IL-10, IL-13, IL-21, IL-23, IL-27, IFN-α, TGF-β, IL-1ra, G-CSF, and soluble receptors for TNF and IL-6. Accordingly, aspects of the disclosure relate to methods for treating, in a patient, an autoimmune disorder, such as MS, a MS-related disorder, diabetes or pre-diabetes, the method comprising, consisting essentially of or yet further consisting of administering to that patient an antigen-MHCII-nanoparticle complex, wherein the antigen is a disease-relevant antigen.

The term "IL-10" or "Interleukin-10" refers to a cytokine encoded by the IL-10 gene. The IL-10 sequence is represented by the GenBank Accession No.: NM_000572.2 (mRNA) and NP_000563.1 (protein).

The term "TGF-β" or "Transforming growth factor beta" refers to a protein that can have an anti-inflammatory effect. TGF-β is a secreted protein that exists in at least three isoforms called TGF-β1, TGF-β2 and TGF-β3. It was also the original name for TGF-β1, which was the founding member of this family. The TGF-β family is part of a superfamily of proteins known as the transforming growth factor beta superfamily, which includes inhibins, activin, anti-müllerian hormone, bone morphogenetic protein, decapentaplegic and Vg-1.

A "an effective amount" is an amount sufficient to achieve the intended purpose, non-limiting examples of such include: initiation of the immune response, modulation of the immune response, suppression of an inflammatory response and modulation of T cell activity or T cell populations. In one aspect, the effective amount is one that functions to achieve a stated therapeutic purpose, e.g., a therapeutically effective amount. As described herein in detail, the effective amount, or dosage, depends on the purpose and the composition, component and can be determined according to the present disclosure.

The use of the word "a" or "an" when used in conjunction with the term "comprising" in the claims and/or the specification may mean "one," but it is also consistent with the meaning of "one or more," "at least one," and "one or more than one."

By "nanosphere," "NP," or "nanoparticle" herein is meant a small discrete particle that is administered singularly or pluraly to a subject, cell specimen or tissue specimen as appropriate. In certain embodiments, the nanoparticles are substantially spherical in shape. In certain embodiments, the nanoparticle is not a liposome or viral particle. In further embodiments, the nanoparticle is solid or has a solid core. The term "substantially spherical," as used herein, means that the shape of the particles does not deviate from a sphere by more than about 10%. Various known antigen or peptide complexes of the invention may be applied to the particles. The nanoparticles of this invention range in size from about 1 nm to about 1 μm and, preferably, from about 1 nm to about 100 nm or alternatively from about 1 nm to about 50 nm, or alternatively from about 5 to 50 nm or alternatively from about 5 nm to 100 nm, and in some aspects refers to the average or median diameter of a plurality of nanoparticles when a plurality of nanoparticles are intended. Smaller nanosize particles can be obtained, for example, by the process of fractionation whereby the larger particles are allowed to settle in an aqueous solution. The upper portion of the solution is then recovered by methods known to those of skill in the art. This upper portion is enriched in smaller size particles. The process can be repeated until a desired average size is generated.

The use of the term "or" in the claims is used to mean "and/or" unless explicitly indicated to refer to alternatives only or the alternatives are mutually exclusive, although the disclosure supports a definition that refers to only alternatives and "and/or."

As used herein the phrase "immune response" or its equivalent "immunological response" refers to the development of a cell-mediated response (mediated by antigen-specific T cells or their secretion products). A cellular immune response is elicited by the presentation of polypeptide epitopes in association with Class I or Class II MHC molecules, to treat or prevent a viral infection, expand antigen-specific Breg cells, TC1, $CD4^+$ T helper cells and/or CD8+ cytotoxic T cells and/or disease generated, autoregulatory T cell and B cell "memory" cells. The response may also involve activation of other components.

The terms "inflammatory response" and "inflammation" as used herein indicate the complex biological response of vascular tissues of an individual to harmful stimuli, such as pathogens, damaged cells, or irritants, and includes secretion of cytokines and more particularly of pro-inflammatory cytokines, i.e. cytokines which are produced predominantly by activated immune cells and are involved in the amplification of inflammatory reactions. Exemplary pro-inflammatory cytokines include but are not limited to IL-1, IL-6, IL-10, TNF-a, IL-17, IL21, IL23, IL27 and TGF-β. Exemplary inflammations include acute inflammation and chronic inflammation. Acute inflammation indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). Chronic inflammation indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be inhibited in the sense of the present disclosure by affecting and in particular inhibiting any one of the events that form the complex biological response associated with an inflammation in an individual.

An autoimmune disorder may include, but is not limited to, diabetes melitus, pre-diabetes, transplantation rejection, multiple sclerosis, a multiple-sclerosis related disorder, premature ovarian failure, scleroderm, Sjogren's disease, lupus, vilelego, alopecia (baldness), polyglandular failure, Grave's disease, hypothyroidism, polymyositis, pemphigus, Crohn's disease, colititis, autoimmune hepatitis, hypopituitarism, myocardititis, Addison's disease, autoimmune skin diseases, uveitis, pernicious anemia, hypoparathyroidism, and/or rheumatoid arthritis. In certain aspects, a peptide component of an antigen/MHCII/particle complex is derived or designed from an autoantigen or an autoantigen epitope, or a mimic thereof, involved in the autoimmune response to be probed, modulated, or blunted by the treatment. In particular aspects, the autoantigen is a peptide, carbohydrate, or lipid. In certain aspects, an autoantigen is a fragment, epitope, or peptide of a protein, carbohydrate, or lipid expressed by certain cells of a subject, such as pancreatic beta cells, and include, but is not limited to a fragment of IGRP, Insulin, GAD or IA-2 protein. Various such proteins or epitopes have been identified for a variety of autoimmune conditions. The autoantigen may be a peptide, carbohydrate, lipid or the like derived from a second endocrine or neurocrine component, such as peri-islet Schwann cell or the like.

As used herein, the term "disease-relevant" antigen intends an antigen or fragment thereof selected to treat a selected disease. For example, a diabetes-relevant antigen is an antigen or fragment thereof that will treat diabetes. A MS-relevant antigen is selected to treat MS. A diabetes-relevant antigen would not be selected to treat MS. Similarly, an autoimmunity related antigen is an antigen that is relevant to an autoimmune disease and would not be selected for the treatment of a disorder or disease other than autoimmunity, e.g., cancer.

As used herein, the term "diabetes" intends a variable disorder of carbohydrate metabolism caused by a combination of hereditary and environmental factors and is usually characterized by inadequate secretion or utilization of insulin, by excessive urine production, by excessive amounts of sugar in the blood and urine, and by thirst, hunger, and loss of weight. Diabetes is characterized by Type 1 diabetes and Type 2 diabetes. The nonobese diabetic ("NOD") mouse is an accepted animal model for the study and treatment of diabetes. Type 1 Diabetes (T1D) in mice is associated with autoreactive CD8+ T-cells. Nonobese diabetic (NOD) mice develop a form of T1D, closely resembling human T1D, that results from selective destruction of pancreatic β cells by T-cells recognizing a growing list of autoantigens. Although initiation of T1D clearly requires the contribution of CD4+ cells, there is compelling evidence that T1D is CD8+ T-cell-dependent. It has been discovered that a significant fraction of islet-associated CD8+ cells in NOD mice use CDR3-invariant Vα17-Jα42+ TCRs, referred to as '8.3-TCR-like'. These cells, which recognize the mimotope NRP-A7 (defined using combinatorial peptide libraries) in the context of the MHC molecule $K^d$, are already a significant component of the earliest NOD islet CD8+ infiltrates, are diabetogenic, and target a peptide from islet-specific glucose-6-phosphatase catalytic subunit-related protein (IGRP), a protein of unknown function. The CD8+ cells that recognize this peptide ($IGRP_{206-214}$, similar to NRP-A7) are unusually frequent in the circulation (>1/200 CD8+ cells). Notably, progression of insulitis to diabetes in NOD mice is invariably accompanied by cyclic expansion of the circulating $IGRP_{206-214}$-reactive CD8+ pool, and by avid maturation of its islet-associated counterpart. More recently, it has been shown that islet-associated CD8+ cells in NOD mice recognize multiple IGRP epitopes, indicating that IGRP is a dominant autoantigen for CD8+ cells, at least in murine T1D. NOD islet-associated CD8+ cells, particularly those found early on in the disease process also recognize an insulin epitope (Ins $B_{15-23}$).

Association studies have suggested that certain HLA class I alleles (i.e., HLA-A*0201) afford susceptibility to human T1D. Pathology studies have shown that the insulitis lesions of newly diagnosed patients consist mostly of (HLA class I-restricted) CD8+ T-cells, which are also the predominant cell population in patients treated by transplantation with pancreas isografts (from identical twins) or allografts (from related donors).

Insulin is a key target of the antibody and CD4+ response in both human and murine T1D. The human insulin B chain epitope $hInsB_{10-18}$ is presented by HLA-A*0201 to autoreactive CD8+ cells both in islet transplant recipients and in the course of spontaneous disease. In addition, four additional peptides have been identified from mouse pre-proinsulin 1 or 2 that are recognized by islet-associated CD8+ T-cells from HLA-A*0201-transgenic mice in the context of HLA-A*0201.

As used herein, the term "pre-diabetes" intends an asymptomatic period preceding a diabetic condition characterized by subclinical beta cell damage wherein the patient exhibits normal plasma glucose levels. It also is characterized by the presence of islet cell autoantibodies (ICAs) and, when close to the onset of clinical symptoms, it may be accompanied by intolerance to glucose.

As used herein, the term "multiple sclerosis" or "MS" intends the autoimmune disorder in which the body's immune system eats away at the protective sheath that covers nerves. This interferes with the communication between the brain and the rest of the body. Ultimately, this may result in deterioration of the nerves themselves, a process that is not reversible.

As used herein, the term "multiple sclerosis-related disorder" intends a disorder that co-presents with a susceptibility to MS or with MS. Non-limiting examples of such include neuromyelitis optica (NMO), uveitis, neuropathis pain sclerosis, atherosclerosis, arteriosclerosis, sclerosis disseminata systemic sclerosis, spino-optical MS, primary progressive MS (PPMS), and relapsing remitting MS (RRMS), progressive systemic sclerosis, and ataxic sclerosis, The terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-20 amino acids in a unique spatial conformation. Methods of determining spatial conformation of epitopes include, for example, x-ray crystallography and 2-dimensional nuclear magnetic resonance. See, e.g., Glenn E. Morris, Epitope Mapping Protocols (1996). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis., 170:1110-1119, 1994), by antigen-dependent killing (cytotoxic T lymphocyte assay, Tigges et al., J. Immunol., 156(10):3901-3910, 1996) or by cytokine secretion. The presence of a cell-mediated immunological response can be determined by proliferation assays ($CD4^+$ T cells) or CTL (cytotoxic T lymphocyte) assays.

Optionally, an antigen or preferably an epitope of an antigen, can be chemically conjugated to, or expressed as, a fusion protein with other proteins, such as MHC and MHC related proteins.

As used herein, the terms "patient" and "subject" are used synonymously and refer to a mammal. In some embodiments the patient is a human. In other embodiments the patient is a mammal commonly used in a laboratory such as a mouse, rat, simian, canine, feline, bovine, equine, or ovine.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It also is contemplated that a particular polypeptide from a given species may be encoded by nucleic acids containing natural variations that have slightly different nucleic acid sequences but, nonetheless, encode the same or substantially similar protein, polypeptide, or peptide.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

It is to be inferred without explicit recitation and unless otherwise intended, that when the present invention relates to an antigen, polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference antigen, protein, antibody, fragment, polypeptide or nucleic acid, and intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

"Homology" or "identity" or "similarity" can also refer to two nucleic acid molecules that hybridize under stringent conditions.

As used herein, the terms "treating," "treatment" and the like are used herein to mean obtaining a desired pharmacologic and/or physiologic effect. The effect may be therapeutic in terms of a partial or complete cure for a disorder and/or adverse effect attributable to the disorder. In one aspect, treatment indicates a reduction in the signs of the disease using an established scale.

IGRP, which is encoded by a gene (located on chromosome 2q28-32 that overlaps a T1D susceptibility locus, IDDM7 (2q31), has also been recently identified as a beta-cell autoantigen of potential relevance in human T1D. Two HLA-A*0201-binding epitopes of human IGRP (hIGRP$_{228-236}$ and hIGRP$_{265-273}$) are recognized by islet-associated CD8+ cells from murine MHC class I-deficient NOD mice expressing an HLA-A*0201 transgene. Non-limited examples of IGRP antigens binding to the murine MHC class II molecule (IAg7) include for example, IGRP$_{206-214}$, which comprises the antigenic peptide VYLK-TNVFL (SEQ ID NO: 4) and IGRP$_{4-22}$, which comprises the antigenic peptide LHRSGVLIIHHLQEDYRTY (SEQ ID NO: 68) or an equivalent thereof, and IGRP$_{128-145}$, which comprises the antigenic peptide TAALSYTISRMEESSVTL (SEQ ID NO: 69) or an equivalent thereof.

"To prevent" intends to prevent a disorder or effect in vitro or in vivo in a system or subject that is predisposed to the disorder or effect.

A "composition" is intended to mean a combination of active agent and another compound or composition, inert (for example, a detectable agent or label) or active, such as an adjuvant. In certain embodiments, the composition does not contain an adjuvant.

A "pharmaceutical composition" is intended to include the combination of an active agent with a carrier, inert or active, making the composition suitable for diagnostic or therapeutic use in vitro, in vivo or ex vivo.

The term "functionally equivalent codon" is used herein to refer to codons that encode the same amino acid, such as the six codons for arginine or serine, and also refers to codons that encode biologically equivalent amino acids (see below Table).

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |// continued

| Codon Table | | | |
|---|---|---|---|
| Amino Acids | | | Codons |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACI |
| Valine | Val | V | GUA GUC GUG GUU |
| Tryptophan | Trp | W | UGG |
| Tyrosine | Tyr | Y | UAC UAU |

As used herein, a "protein" or "polypeptide" or "peptide" refers to a molecule comprising at least five amino acid residues.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

II. DESCRIPTIVE EMBODIMENTS

There is currently no therapeutic platform that enables complete suppression of polyclonal autoimmune responses without compromising systemic immunity. Applicant's disclosure described herein enables the design of autoimmune disease-specific medicines that turn autoreactive disease-specific CD4+ T-cells and B-cells into cognate, mono-specific regulatory CD4+ T-cells and B-cells that coordinately suppress all other autoreactive T and B-cell responses of the host, regardless of their fine antigenic specificity, and yet with exquisite disease-specificity and without impairing systemic immunity.

The Autoantigenic Complexity of Type 1 Diabetes (T1D).

T1D is caused by a chronic autoimmune response that progressively erodes the pancreatic Beta-cell mass. B-cell destruction in both humans and NOD mice is effected by T-cells recognizing many autoantigens (Tsai, S. et al. (2008) Adv. Immunol. 100:79-124; Lieberman, S. et al. (2003) Tissue Antigens 62:359-377). Although the precise sequence of events remains ill defined, current evidence suggests that T1D requires CD4+ and CD8+ cells; that autoreactive T cells differentiate into killers by engaging B-cell antigens on local APCs; and that these T-cells target a wide repertoire of autoantigens (Tsai, S. et al. (2008) Adv. Immunol. 100:79-124; Santamaria, P. (2010) Immunity 32:437-445).

It has been shown that soluble peptides can induce peptide-specific T-cell tolerance in vivo, but cannot blunt poly-specific autoimmune responses (Han et al. (2005) Nature Medicine 11(6):645-652). Unexpectedly, it was found that, unlike therapy with soluble peptide, therapy with NPs coated with a single T1D-relevant pMHC class I (originally used as a negative control) blunted the progression of T1D in pre-diabetic NOD mice and restored normoglycemia in diabetic animals (Tsai, S. et al. (2010) Immunity 32:568-580). Subsequent work led to the unexpected discovery that pMHC-NP therapy functions by expanding, in an epitope-specific manner, autoantigen-experienced autoreactive CD8+ cells that suppressed the recruitment of other autoantigenic T cell specificities by inhibiting and killing autoantigen-loaded APCs. More recently, Applicant has found that this therapeutic platform can be harnessed for the in vivo expansion of autoreactive T-regulatory CD4+ cells. Specifically, Applicant discovered that NPs coated with individual T1D-relevant pMHC class II expand disease-specific TR1 CD4+ T-cells, expressing the TR1 markers CD49b and LAG3 (Gagliani, N. et al. (2013) Nature Medicine 19:739-746) and producing the cytokines IL10 and TGF-β (see below).

Collectively, these observations support a new paradigm in the progression of autoimmunity, stating that chronic stimulation of naïve autoreactive CD8+ or CD4+ T cells by endogenous epitopes triggers their differentiation into memory-like autoreactive regulatory T cells; and that these memory autoreactive regulatory cells suppress the activation of both cognate and non-cognate high-avidity autoreactive T cell specificities by suppressing and/or killing autoantigen-loaded APCs (Tsai, S. et al. (2010) Immunity 32:568-580). Importantly, and without being bound by theory, any single epitope (pMHC) specificity involved in an autoimmune disease (among many) can be used, when coated as a ligand onto NPs, to blunt complex autoimmune responses. It is Applicant's belief that these NP preparations cannot activate naïve T-cells, hence induce effector T-cell responses, because they lack key co-stimulatory molecules, such as CD80 and CD86. In fact, cognate naïve and effector autoreactive cells are deleted by this approach. Therefore, the therapeutic approach that enabled its discovery provide a platform for a new class of therapeutics in autoimmunity, potentially capable of resolving polyclonal autoimmune responses in a disease- and organ-specific manner without compromising systemic immunity.

III. METHODS

Medical and diagnostic methods are also provided. In one aspect, a method is provided for promoting the formation, expansion and recruitment of B-regulatory cells and/or TR1 cells (e.g., TR1 and CD4+ cells) in an antigen-specific manner in a subject in need thereof, comprising, or alternatively consisting essentially of, or yet further consisting of, administering to the subject an effective amount of the NP-complex or composition as described herein.

In another aspect, a method for treating or preventing an autoimmune disease or disorder as described herein, e.g., MS, a MS-related disorder, diabetes or pre-diabetes, in a subject in need thereof is provided, the method comprising, or alternatively consisting essentially of, or yet further consisting of, administering to the subject an effective amount of the NP-complex or composition as described herein, wherein the autoantigen is disease-relevant for the disease to be treated, e.g., for the prevention or treatment of diabetes, the antigen is a diabetes-relevant antigen. In a further aspect, the autoimmune disease is multiple-sclerosis or a multiple-sclerosis related disorder and the antigen is MS-relevant.

Peptide antigens for the treatment or prevention of pre-diabetes or diabetes, include, but are not limited to hInsB$_{10-18}$ (HLVEALYLV (SEQ ID NO: 1)), hIGRP$_{228-236}$ (LNIDLLWSV (SEQ ID NO: 2)), hIGRP$_{265-273}$ (VLFGLGFAI (SEQ ID NO: 3)), IGRP$_{206-214}$ (VYLKTNVFL (SEQ ID NO: 4)), NRP-A7 (KYNKANAFL (SEQ ID NO: 5)), NRP-I4 (KYNIANVFL (SEQ ID NO: 6)), NRP-V7 (KYNKANVFL (SEQ ID NO: 7)), YAI/D$^b$ (FQDENYLYL (SEQ ID NO: 8)) and/or INS B$_{15-23}$ (LYLVCGERG (SEQ ID NO: 9)), GAD65$_{114-123}$, VMNILLQYVV (SEQ ID NO: 10); GAD65$_{536-545}$, RMMEYGTTMV (SEQ ID NO: 11); GFAP$_{143-151}$, NLAQTDLATV (SEQ ID NO: 12); GFAP$_{214-222}$, QLARQQVHV (SEQ ID NO: 13); IA-2$_{172-180}$, SLSPLQAEL (SEQ ID NO: 14); IA-2$_{482-490}$, SLAAGVKLL (SEQ ID NO: 15); IA-2$_{805-813}$, VIVMLTPLV (SEQ ID NO: 16); ppIAPP$_{5-13}$, KLQVFLIVL (SEQ ID NO: 17); ppIAPP$_{9-17}$, FLIVLSVAL (SEQ ID NO: 18); IGRP$_{152-160}$, FLWSVFMLI (SEQ ID NO: 19); IGRP$_{211-219}$, NLFLFLFAV (SEQ ID NO: 20); IGRP$_{215-223}$, FLFAVGFYL (SEQ ID NO: 21); IGRP$_{222-230}$, YLLLRVLNI (SEQ ID NO: 22); IGRP$_{228-236}$, LNIDLLWSV (SEQ ID NO: 23); IGRP$_{265-273}$, VLFGLGFAI (SEQ ID NO: 3); IGRP$_{293-301}$, RLLCALTSL (SEQ ID NO: 24); Pro-insulin$_{L2-10}$, ALWMRLLPL (SEQ ID NO: 25); Pro-insulin$_{L3-11}$, LWMRLLPLL (SEQ ID NO: 26); Pro-insulin$_{L6-14}$, RLLPLLALL (SEQ ID NO: 27); Pro-insulin$_{B5-14}$, HLCGSHLVEA (SEQ ID NO: 28); Pro-insulin$_{B10-18}$, HLVEALYLV (SEQ ID NO: 1); Pro-insulin$_{B14-22}$, ALYLVCGER (SEQ ID NO: 29); Pro-insulin$_{B15-24}$, LYLVCGERGF (SEQ ID NO: 30); Pro-insulin$_{B17-25}$, LVCGERGFF (SEQ ID NO: 31); Pro-insulin$_{B18-27}$, VCGERGFFYT (SEQ ID NO: 32); Pro-insulin$_{B20-27}$, GERGFFYT (SEQ ID NO: 33); Pro-insulin$_{B21-29}$, ERGFFYTPK (SEQ ID NO: 34); Pro-insulin$_{B25-C1}$, FYTPKTRRE (SEQ ID NO: 35); Pro-insulin$_{B27-C5}$, TPKTRREAEDL (SEQ ID NO: 36); Pro-insulin$_{C20-28}$, SLQPLALEG (SEQ ID NO: 37); Pro-insulin$_{C25-33}$, ALEGSLQKR (SEQ ID NO: 38); Pro-insulin$_{C29-A5}$, SLQKRGIVEQ (SEQ ID NO: 39); Pro-insulin$_{41-10}$, GIVEQCCTSI (SEQ ID NO: 40); Pro-insulin$_{A2-10}$, IVEQCCTSI (SEQ ID NO: 41); Pro-insulin$_{A12-20}$, SLYQLENYC (SEQ ID NO: 42) or equivalents and/or combinations thereof. Additional examples include ProIns 76-90, SLQPLALEGSLQKRG (SEQ ID NO: 43), ProIns 79-89, PLALEGSLQKR (SEQ ID NO: 44), ProIns 90-109, GIVEQCCTSICSLYQLENYC (SEQ ID NO: 45), ProIns 94-105, QCCTSICSLYQL (SEQ ID NO: 46), GAD 247-266, NMYAMMIARFKMFPEVKEKG (SEQ ID NO: 47), GAD 255-265, RFKMFPEVKEK (SEQ ID NO: 48), GAD 555-567, NFFRMVISNPAAT (SEQ ID NO: 49), IGRP 13-25, QHLQKDYRAYYTF (SEQ ID NO: 50), IGRP 8-27, GVLIIQHLQKDYRAYYTFLN (SEQ ID NO: 51), ProIns B24-C36, FFYTPMSRREVED (SEQ ID NO: 52) and equivalents of each thereof.

When the method is directed to the treatment of MS or MS-related disorders, the complex includes antigens related to multiple sclerosis. Such antigens include, for example, those disclosed in U.S. Patent Publication No. 2012/0077686, and antigens derived from myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, and 2'3'-cyclic nucleotide 3'-phosphodiesterase. In certain embodiments, the antigen is derived from Myelin Oligodendrocyte Glycoprotein (MOG). Non-limited examples include, for example, $MAG_{287-295}$, SLLLELEEV (SEQ ID NO: 53); $MAG_{509-517}$, LMWAKIGPV (SEQ ID NO: 54); $MAG_{556-564}$, VLFSSD-FRI (SEQ ID NO: 55); $MBP_{110-118}$, SLSRFSWGA (SEQ ID NO: 56); $MOG_{114-122}$, KVEDPFYWV (SEQ ID NO: 57); $MOG_{166-175}$, RTFDPHFLRV (SEQ ID NO: 58); $MOG_{172-180}$, FLRVPCWKI (SEQ ID NO: 59); $MOG_{179-188}$, KITLFVIVPV (SEQ ID NO: 60); $MOG_{188-196}$, VLG-PLVALI (SEQ ID NO: 61); $MOG_{181-189}$, TLFVIVPVL (SEQ ID NO: 62); $MOG_{205-214}$, RLAGQFLEEL (SEQ ID NO: 63); $PLP_{80-88}$, FLYGALLLA (SEQ ID NO: 64) or equivalents or combinations thereof.

Additional non-limiting examples of antigens that can be used in this invention comprise polypeptides comprising, or alternatively consisting essentially of, or yet further consisting of the polypeptides of the group: $MOG_{35-55}$, MEVGWYRSPFSRVVHLYRNGK (SEQ ID NO: 65); $MOG_{36-55}$, EVGWYRSPFSRVVHLYRNGK (SEQ ID NO: 66); $MAG_{287-295}$, SLLLELEEV (SEQ ID NO: 53); $MAG_{509-517}$, LMWAKIGPV (SEQ ID NO: 54); $MAG_{556-564}$, VLFSSD-FRI (SEQ ID NO: 55); $MBP_{110-118}$, SLSRFSWGA (SEQ ID NO: 56); $MOG_{114-122}$, KVEDPFYWV (SEQ ID NO: 57); $MOG_{166-175}$, RTFDPHFLRV (SEQ ID NO: 58); $MOG_{172-180}$, FLRVPCWKI (SEQ ID NO: 59); $MOG_{179-188}$, KITLFVIVPV (SEQ ID NO: 60); $MOG_{188-196}$, VLG-PLVALI (SEQ ID NO: 61); $MOG_{181-189}$, TLFVIVPVL (SEQ ID NO: 62); $MOG_{205-214}$, RLAGQFLEEL (SEQ ID NO: 63); $PLP_{80-88}$, FLYGALLLA (SEQ ID NO: 64), or an equivalent of each thereof, or combinations thereof.

Methods to determine and monitor the therapy are known in the art and briefly described herein. When delivered in vitro, administration is by contacting the composition with the tissue or cell by any appropriate method, e.g., by administration to cell or tissue culture medium and is useful as a screen to determine if the therapy is appropriate for an individual or to screen for alternative therapies to be used as a substitute or in combination with the disclosed compositions. When administered in vivo, administration is by systemic or local administration. In vivo, the methods can be practiced on a non-human animal to screen alternative therapies to be used as a substitute or in combination with the disclosed compositions prior to human administration. In a human or non-human mammal, they are also useful to treat the disease or disorder.

The above methods require administration of an effective amount of a NP-complex.

The MHC of the antigen-MHC-nanoparticle complex can be MHC I, MHC II, or non-classical MHC but preferably MHCII. MHC proteins are described herein. In one embodiment, the MHC of the antigen-MHC-nanoparticle complex is a MHC class I. In another embodiment, the MHC is a MHC class II. In other embodiments, the MHC component of the antigen-MHC-nanoparticle complex is MHC class II or a non-classical MHC molecule as described herein. In one aspect, the antigen comprises, or alternatively consists essentially of, or yet further consists of the polypeptide GWYRSPFSRVVH (SEQ ID NO: 67) or an equivalent of GWYRSPFSRVVH (SEQ ID NO: 67).

The size of the nanoparticle can range from about 1 nm to about 1 µm. In certain embodiments, the nanoparticle is less than about 1 µm in diameter. In other embodiments, the nanoparticle is less than about 500 nm, less than about 400 nm, less than about 300 nm, less than about 200 nm, less than about 100 nm, or less than about 50 nm in diameter. In further embodiments, the nanoparticle is from about 1 nm to about 10 nm, 15 nm, 20 nm, 25 nm, 30 nm, 40 nm, 50 nm, 75 nm, or 100 nm in diameter. In specific embodiments, the nanoparticle is from about 1 nm to about 100 nm, about 1 nm to about 50 nm, about 1 nm to about 20 nm, or about 5 nm to about 20 nm.

The size of the complex can range from about 5 nm to about 1 µm. In certain embodiments, the complex is less than about 1 µm or alternatively less than 100 nm in diameter. In other embodiments, the complex is less than about 500 nm, less than about 400 nm, less than about 300 nm, less than about 200 nm, less than about 100 nm, or less than about 50 nm in diameter. In further embodiments, the complex is from about 5 nm or 10 nm to about 50 nm, or about 5 nm to about 75 nm, or about 5 nm to about 50 nm, or about 5 nm to about 60 nm, or from about 10 nm to about 60 nm, or in one aspect about 55 nm.

Applicant has discovered that the density of the antigen-MHC complexes on the nanoparticle contributes to the therapeutic benefit. Thus, as disclosed herein the antigen-MHC nanoparticle complex can have a defined density in the range of from about 0.05 MHC molecules per 100 $nm^2$ of surface area of the nanoparticle including the complex, assuming at least 2 MHC, or alternatively at least 8, or alternatively at least 9, or alternatively at least 10, or alternatively at least 11, or alternatively at least 12, MHC complexed to the nanoparticle. In one aspect the complex has a density of MHC from about 0.01 MHC per 100 $nm^2$ (0.05 MHC/100 $nm^2$) to about 30 MHC/100 $nm^2$, or alternatively from 0.1 MHC/100 $nm^2$ to about 25 MHC/100 $nm^2$, or alternatively from about 0.3 MHC/100 $nm^2$ to about 25 MHC/100 $nm^2$, or alternatively from about 0.4 MHC/100 $nm^2$ to about 25 MHC/100 $nm^2$, or alternatively from about 0.5 MHC/100 $nm^2$ to about 20 MHC/100 $nm^2$, or alternatively from 0.6 MHC/100 $nm^2$ to about 20 MHC/100 $nm^2$, or alternatively from about 1.0 MHC/100 $nm^2$ to about 20 MHC/100 $nm^2$, or alternatively from about 5.0 MHC/100 $nm^2$ to about 20 MHC/100 $nm^2$, or alternatively from about 10.0 MHC/100 $nm^2$ to about 20 MHC/100 $nm^2$, or alternatively from about 15 MHC/100 $nm^2$ to about 20 MHC/100 $nm^2$, or alternatively at least about 0.5, or alternatively at least about 1.0, or alternatively at least about 5.0, or alternatively at least about 10.0, or alternatively at least about 15.0 MHC/100 $nm^2$. In one aspect, when 9 or at least 9 MHC are complexed to a nanoparticle, the density range is from about 0.3 MHC/100 $nm^2$ to about 20 MHC/100 $nm^2$.

In one of its method aspects, there is provided a method for accumulating B-regulatory cells and/or anti-inflammatory T cells in a patient in need thereof. In a further embodiment, the T cell is a CD4+ or CD8+ T cell. In a related embodiment, the T cell secretes IL-10 or TGF-β. The method comprises, consists essentially of, or yet further consists of administering to a patient in need thereof an effective amount of the antigen-MHC nanoparticle complex as described herein.

In one embodiment, the compositions and methods described herein are for treating an autoimmune disorder such as MS, MS-associated disorder, diabetes or pre-diabetes. The method comprises, consists essentially of, or yet further consists of administering to a patient in need thereof an effective amount of the antigen-MHCII nanoparticle complex as described herein.

Details regarding modes of administration in vitro and in vivo are described within.

This disclosure also provides use of the NP-complexes for the preparation of medicaments for the treatment and/or prevention of diseases and disorders as described herein.

IV. ANTIGEN-MHC-NANOPARTICLE COMPLEXES

A. Polypeptides and Polynucleotides

Further aspects relate to an isolated or purified polypeptide antigens, comprising, or consisting essentially of, or yet further consisting of, the amino acid sequences as described herein, or a polypeptide having at least about 80% sequence identity, or alternatively at least 85%, or alternatively at least 90%, or alternatively at least 95%, or alternatively at least 98% sequence identity to the amino acid sequences of the antigens, or polypeptides encoded by polynucleotides having at about 80% sequence identity, or alternatively at least 85%, or alternatively at least 90%, or alternatively at least 95%, or alternatively at least 98% sequence identity to the polynucleotide encoding the amino acid sequences of the antigen, or its complement, or a polypeptide encoded by a polynucleotide that hybridizes under conditions of moderate to high stringency to a polynucleotide encoding the amino acid sequence of the antigens, or its complement. Also provided are isolated and purified polynucleotides encoding the antigen polypeptides disclosed herein, or amino acids having at least about 80% sequence identity thereto, or alternatively at least 85%, or alternatively at least 90%, or alternatively at least 95%, or alternatively at least 98% sequence identity to the disclosed sequences, or an equivalent, or a polynucleotide that hybridizes under stringent conditions to the polynucleotide, its equivalent or its complement and isolated or purified polypeptides encoded by these polynucleotides. The polypeptides and polynucleotides can be combined with non-naturally occurring substances with which they are not associated with in nature, e.g., carriers, pharmaceutically acceptable carriers, vectors and MHC molecules, nanoparticles as known in the art and as described herein.

Antigens, including segments, fragments and other molecules derived from an antigenic species, including but not limited to peptides, carbohydrates, lipids or other molecules presented by classical and non-classical MHC molecules of the invention are typically complexed or operatively coupled to a MHC molecule or derivative thereof. Antigen recognition by T lymphocytes is major histocompatibility complex (MHC)-restricted. A given T lymphocyte will recognize an antigen only when it is bound to a particular MHC molecule. In general, T lymphocytes are stimulated only in the presence of self-MHC molecules, and antigen is recognized as fragments of the antigen bound to self MHC molecules. MHC restriction defines T lymphocyte specificity in terms of the antigen recognized and in terms of the MHC molecule that binds its antigenic fragment(s). In particular aspects certain antigens will be paired with certain MHC molecules or polypeptides derived therefrom.

The term "operatively coupled" or "coated" as used herein, refers to a situation where individual polypeptide (e.g., MHC) and antigenic (e.g., peptide) components are combined to form the active complex prior to binding at the target site, for example, an immune cell. This includes the situation where the individual polypeptide complex components are synthesized or recombinantly expressed and subsequently isolated and combined to form a complex, in vitro, prior to administration to a subject; the situation where a chimeric or fusion polypeptide (i.e., each discrete protein component of the complex is contained in a single polypeptide chain) is synthesized or recombinantly expressed as an intact complex. Typically, polypeptide complexes are added to the nanoparticles to yield nanoparticles with adsorbed or coupled polypeptide complexes having a ratio of number of molecules:number of nanoparticle ratios from about, at least about or at most about about 0.1, 0.5, 1, 3, 5, 7, 10, 15, 20, 25, 30, 35, 40, 50, 100, 125, 150, 175, 200, 225, 250, 275, 300, 325, 350, 375, 400, 425, 450, 475, 500, 600, 700, 800, 900, 1000, 1500 or more to:1, more typically 0.1:1, 1:1 to 50:1 or 300:1. The polypeptide content of the nanoparticles can be determined using standard techniques.

B. MHC Molecules

Intracellular and extracellular antigens present quite different challenges to the immune system, both in terms of recognition and of appropriate response. Presentation of antigens to T cells is mediated by two distinct classes of molecules MHC class I (MHC-I) and MHC class II (MHC-II) (also identified as "pMHC" herein), which utilize distinct antigen processing pathways. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. In certain embodiments of the invention, a particular antigen is identified and presented in the antigen-MHC-nanoparticle complex in the context of an appropriate MHC class I or II polypeptide. In certain aspects, the genetic makeup of a subject may be assessed to determine which MHC polypeptide is to be used for a particular patient and a particular set of peptides. In certain embodiments, the MHC class 1 component comprises all or part of a HLA-A, HLA-B, HLA-C, HLA-E, HLA-F, HLA-G or CD-1 molecule. In embodiments wherein the MHC component is a MHC class II component, the MHC class II component can comprise all or part of a HLA-DR, HLA-DQ, or HLA-DP.

Non-classical MHC molecules are also contemplated for use in MHC complexes of the invention. Non-classical MHC molecules are non-polymorphic, conserved among species, and possess narrow, deep, hydrophobic ligand binding pockets. These binding pockets are capable of presenting glycolipids and phospholipids to Natural Killer T (NKT) cells or certain subsets of CD8+ T-cells such as Qa1 or HLA-E-restricted CD8+ T-cells. NKT cells represent a unique lymphocyte population that co-express NK cell markers and a semi-invariant T cell receptor (TCR). They are implicated in the regulation of immune responses associated with a broad range of diseases.

C. Antigenic Components

Certain aspects of the invention include methods and compositions concerning antigenic compositions including segments, fragments, or epitopes of polypeptides, peptides, nucleic acids, carbohydrates, lipids and other molecules that provoke or induce an antigenic response, generally referred to as antigens. In particular, antigenic segments or fragments of antigenic determinants, which lead to the destruction of a cell via an autoimmune response, can be identified and used in making an antigen-MHC-nanoparticle complex described herein. Embodiments of the invention include compositions and methods for the modulation of an immune response in a cell or tissue of the body.

Antigenic polypeptides and peptides of the invention may be modified by various amino acid deletions, insertions, and/or substitutions. In particular embodiments, modified polypeptides and/or peptides are capable of modulating an immune response in a subject. In some embodiments, a wild-type version of a protein or peptide are employed, however, in many embodiments of the invention, a modified protein or polypeptide is employed to generate an antigen-MHC-nanoparticle complex. An antigen-MHC-nanoparticle complex can be used to generate an anti-inflammatory immune response, to modify the T cell population of the immune system (i.e., re-educate the immune system), and/or foster the recruitment and accumulation of anti-inflammatory T cells to a particular tissue. The terms described above may be used interchangeably herein. A "modified protein" or "modified polypeptide" or "modified peptide" refers to a protein or polypeptide whose chemical structure, particularly its amino acid sequence, is altered with respect to the wild-type protein or polypeptide. In some embodiments, a modified protein or polypeptide or peptide has at least one modified activity or function (recognizing that proteins or polypeptides or peptides may have multiple activities or functions). It is specifically contemplated that a modified protein or polypeptide or peptide may be altered with respect to one activity or function yet retains a wild-type activity or function in other respects, such as immunogenicity or ability to interact with other cells of the immune system when in the context of an MHC-nanoparticle complex.

Non-limiting examples, of peptide antigens include, but are not limited to $hInsB_{10-18}$ (HLVEALYLV (SEQ ID NO: 1)), $hIGRP_{228-236}$ (LNIDLLWSV (SEQ ID NO: 2)), $hIGRP_{265-273}$ (VLFGLGFAI (SEQ ID NO: 3)), $IGRP_{206-214}$ (VYLKTNVFL (SEQ ID NO: 4)), NRP-A7 (KYNKANAFL (SEQ ID NO: 5)), NRP-I4 (KYNIANVFL (SEQ ID NO: 6)), NRP-V7 (KYNKANVFL (SEQ ID NO: 7)), $YAI/D^b$ (FQDENYLYL (SEQ ID NO: 8)) and/or INS $B_{15-23}$ (LYLVCGERG (SEQ ID NO: 9)), as well as peptides and proteins disclosed in U.S. Patent Application Publication No. 2005/0202032 and equivalents and/or combinations thereof.

In certain aspects, a peptide antigen for treatment of T1D is $GAD65_{114-123}$, VMNILLQYVV (SEQ ID NO: 10); $GAD65_{536-545}$, RMMEYGTTMV (SEQ ID NO: 11); $GFAP_{143-151}$, NLAQTDLATV (SEQ ID NO: 12); $GFAP_{214-222}$, QLARQQVHV (SEQ ID NO: 13); $IA-2_{172-180}$, SLSPLQAEL (SEQ ID NO: 14); $IA-2_{482-490}$, SLAAGVKLL (SEQ ID NO: 15); $IA-2_{805-813}$, VIVMLTPLV (SEQ ID NO: 16); $ppIAPP_{5-13}$, KLQVFLIVL (SEQ ID NO: 17); $ppIAPP_{9-17}$, FLIVLSVAL (SEQ ID NO: 18); $IGRP_{152-160}$, FLWSVFMLI (SEQ ID NO: 19); $IGRP_{211-219}$, NLFLFLFAV (SEQ ID NO: 20); $IGRP_{215-223}$, FLFAVGFYL (SEQ ID NO: 21); $IGRP_{222-230}$, YLLLRVLNI (SEQ ID NO: 22); $IGRP_{228-236}$, LNIDLLWSV (SEQ ID NO: 23); $IGRP_{265-273}$, VLFGLGFAI (SEQ ID NO: 3); $IGRP_{293-301}$, RLLCALTSL (SEQ ID NO: 24); Pro-insulin$_{L2-10}$, ALWMRLLPL (SEQ ID NO: 25); Pro-insulin$_{L3-11}$, LWMRLLPLL (SEQ ID NO: 26); Pro-insulin$_{L6-14}$, RLLPLLALL (SEQ ID NO: 27); Pro-insulin$_{B5-14}$, HLCGSHLVEA (SEQ ID NO: 28); Pro-insulin$_{B10-18}$, HLVEALYLV (SEQ ID NO: 1); Pro-insulin$_{B14-22}$, ALYLVCGER (SEQ ID NO: 29); Pro-insulin$_{B15-24}$, LYLVCGERGF (SEQ ID NO: 30); Pro-insulin$_{B17-25}$, LVCGERGFF (SEQ ID NO: 31); Pro-insulin$_{B18-27}$, VCGERGFFYT (SEQ ID NO: 32); Pro-insulin$_{B20-27}$, GERGFFYT (SEQ ID NO: 33); Pro-insulin$_{B21-29}$, ERGFFYTPK (SEQ ID NO: 34); Pro-insulin$_{B25-C1}$, FYTPKTRRE (SEQ ID NO: 35); Pro-insulin$_{B27-C5}$, TPKTRREAEDL (SEQ ID NO: 36); Pro-insulin$_{C20-28}$, SLQPLALEG (SEQ ID NO: 37); Pro-insulin$_{C25-33}$, ALEGSLQKR (SEQ ID NO: 38); Pro-insulin$_{C29-A5}$, SLQKRGIVEQ (SEQ ID NO: 39); Pro-insulin$_{41-10}$, GIVEQCCTSI (SEQ ID NO: 40); Pro-insulin$_{42-10}$, IVEQCCTSI (SEQ ID NO: 41); Pro-SLYQLENYC (SEQ ID NO: 42) or equivalents and/or combinations thereof.

Additional non-limiting examples of antigens include MS and MS-relevant or related antigens that can be used in this invention comprise polypeptides comprising, or alternatively consisting essentially of, or yet further consisting of the polypeptides of the group: $MOG_{35-55}$, MEVGWYRSPFSRVVHLYRNGK (SEQ ID NO: 65); $MOG_{36-55}$, EVGWYRSPFSRVVHLYRNGK (SEQ ID NO: 66); $MAG_{287-295}$, SLLLELEEV (SEQ ID NO: 53); $MAG_{509-517}$, LMWAKIGPV (SEQ ID NO: 54); $MAG_{556-564}$, VLFSSDFRI (SEQ ID NO: 55); $MBPI_{110-118}$, SLSRFSWGA (SEQ ID NO: 56); $MOG_{114-122}$, KVEDPFYWV (SEQ ID NO: 57); $MOG_{166-175}$, RTFDPHFLRV (SEQ ID NO: 58); $MOG_{172-180}$, FLRVPCWKI (SEQ ID NO: 59); $MOG_{179-188}$, KITLFVIVPV (SEQ ID NO: 60); $MOG_{188-196}$, VLGPLVALI (SEQ ID NO: 61); $MOG_{181-189}$, TLFVIVPVL (SEQ ID NO: 62); $MOG_{205-214}$, RLAGQFLEEL (SEQ ID NO: 63); $PLP_{80-88}$, FLYGALLLA (SEQ ID NO: 64), or an equivalent of each thereof, or combinations thereof.

In still further aspects peptide antigens for the treatment of MS and MS-related disorders include without limitation: $MOG_{35-55}$, MEVGWYRSPFSRVVHLYRNGK (SEQ ID NO: 65) $MOG_{36-55}$, EVGWYRSPFSRVVHLYRNGK (SEQ ID NO: 66) $MAG_{287-295}$, SLLLELEEV (SEQ ID NO: 53); $MAG_{509-517}$, LMWAKIGPV (SEQ ID NO: 54); $MAG_{556-564}$, VLFSSDFRI (SEQ ID NO: 55); $MBP_{110-118}$, SLSRFSWGA (SEQ ID NO: 56); $MOG_{114-122}$ KVEDPFYWV (SEQ ID NO: 57); $MOG_{166-175}$, RTFDPHFLRV (SEQ ID NO: 58); $MOG_{172-180}$, FLRVPCWKI (SEQ ID NO: 59); $MOG_{179-188}$, KITLFVIVPV (SEQ ID NO: 60); $MOG_{188-196}$, VLGPLVALI (SEQ ID NO: 61); $MOG_{181-189}$, TLFVIVPVL (SEQ ID NO: 62); $MOG_{205-214}$, RLAGQFLEEL (SEQ ID NO: 63); $PLP_{80-88}$, FLYGALLLA (SEQ ID NO: 64) $MAG_{287-295}$, SLLLELEEV (SEQ ID NO: 53); $MAG_{509-517}$, LMWAKIGPV (SEQ ID NO: 54); $MAG_{556-564}$, VLFSSDFRI (SEQ ID NO: 55), and equivalents and/or combinations thereof.

Antigens for the treatment of MS and MS-related disorders include, those disclosed in U.S. Patent Application Publication No. 2012/0077686, and antigens derived from myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, and 2'3'-cyclic nucleotide 3'-phosphodiesterase. In certain embodiments, the antigen is derived from Myelin Oligodendrocyte Glycoprotein (MOG).

In certain embodiments, the size of a protein or polypeptide (wild-type or modified), including any complex of a protein or peptide of interest and in particular a MHC-peptide fusion, may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. In certain aspects, 5, 6, 7, 8, 9, 10 or more contiguous amino acids, including derivatives thereof, and fragments of an antigen, such as those amino acid sequences disclosed and referenced herein, can be used as antigens. It is contemplated that polypeptides may be mutated by truncation, rendering them shorter than their corresponding wild-type form, but also they might be altered by fusing or conjugating a heterologous protein sequence with a particular function (e.g., for presentation as a protein complex, for enhanced immunogenicity, etc.).

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of autoantigenic epitopes and other polypeptides of these compositions can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a nonpolar or uncharged amino acid, and vice versa.

Proteins of the invention may be recombinant, or synthesized in vitro. Alternatively, a recombinant protein may be isolated from bacteria or other host cell.

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 µg/ml or mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be antigen-MHC-nanoparticle complex.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, Adv. Enzymol., 47:45-148, 1978; Chous and Fasman, Annu. Rev. Biochem., 47:251-276, 1978, Chou and Fasman, Biochemistry, 13(2):211-222, 1974; Chau and Fasman, Biochemistry, 13(2):222-245, 1974, Chou and Fasman, Biophys. J., 26(3):385-399, 1979). Any of these may be used, if desired, to supplement the teachings of Hopp in U.S. Pat. No. 4,554,101.

For any given autoimmune disease the antigen MHC complex can be identified and pre-selected using known methods in the art. Algorithms exist—derived from a set of aligned peptides known to bind to a given MHC molecule, which can be used as a predictor of both peptide-MHC binding and T-cell epitopes. See, e.g., Reche and Reinherz (2007) Methods Mol. Biol. 409:185-200.

Molecules other than peptides can be used as antigens or antigenic fragments in complex with MHC molecules, such molecules include, but are not limited to carbohydrates, lipids, small molecules, and the like. Carbohydrates are major components of the outer surface of a variety of cells. Certain carbohydrates are characteristic of different stages of differentiation and very often these carbohydrates are recognized by specific antibodies. Expression of distinct carbohydrates can be restricted to specific cell types.

D. Substrates/Nanoparticles

In certain aspect, antigen/MHC complexes are operatively coupled to a substrate which can be bound covalently or non-covalently to the substrate. A substrate can be in the form of a nanoparticle that optionally comprises a biocompatible and/or bioabsorbable material. Accordingly, in one embodiment, the nanoparticle is biocompatible and/or bioabsorbable. In another aspect, the nanoparticle has a solid core and/or is not a liposome. A substrate can also be in the form of a nanoparticle such as those described previously in U.S. Patent Publication No. 2009/0155292. Nanoparticles can have a structure of variable dimension and known variously as a nanosphere, a nanoparticle or a biocompatible biodegradable nanosphere or a biocompatible biodegradable nanoparticle. Such particulate formulations containing an antigen/MHC complex can be formed by covalent or non-covalent coupling of the complex to the nanoparticle.

The nanoparticles typically consist of a substantially spherical core and optionally one or more layers. The core may vary in size and composition. In addition to the core, the nanoparticle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired nanoparticle diameter), these layers typically being applied on the outer surface of the nanoparticle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997. In certain embodiments, the compositions of the core and layers may vary provided that the nanoparticles are biocompatible and bioabsorbable. The core could be of homogeneous composition, or a composite of two or more classes of material depending on the properties desired. In certain aspects, metal nanospheres will be used. These metal nanoparticles can be formed from Fe, Ca, Ga and the like. In certain embodiments, the nanoparticle comprises a core comprising metal or metal oxide such as gold or iron oxide.

As previously stated, the nanoparticle may, in addition to the core, include one or more layers. The nanoparticle may include a layer consisting of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxalkanoate)s of the PHB-PHV class; and other modified poly(saccharides) such as starch, cellulose and chitosan. Additionally, the nanoparticle may include a layer with suitable surfaces for attaching chemical functionalities for chemical binding or coupling sites.

Layers can be produced on the nanoparticles in a variety of ways known to those skilled in the art. Examples include sol-gel chemistry techniques such as described in Iler, Chemistry of Silica, John Wiley & Sons, 1979; Brinker and Scherer, Sol-gel Science, Academic Press, (1990). Additional approaches to producing layers on nanoparticles include surface chemistry and encapsulation techniques such as described in Partch and Brown, J. Adhesion, 67:259-276, 1998; Pekarek et al., Nature, 367:258, (1994); Hanprasopwattana, Langmuir, 12:3173-3179, (1996); Davies, Advanced Materials, 10:1264-1270, (1998); and references therein. Vapor deposition techniques may also be used; see for example Golman and Shinohara, Trends Chem. Engin., 6:1-6, (2000); and U.S. Pat. No. 6,387,498. Still other approaches include layer-by-layer self-assembly techniques such as described in Sukhorukov et al., Polymers Adv. Tech., 9(10-11):759-767, (1998); Caruso et al., Macromolecules, 32(7):2317-2328, (1998); Caruso et al., J. Amer. Chem. Soc., 121(25):6039-6046, (1999); U.S. Pat. No. 6,103,379 and references cited therein.

Nanoparticles may be formed by contacting an aqueous phase containing the antigen/MHC/co-stimulatory molecule complex and a polymer and a nonaqueous phase followed by evaporation of the nonaqueous phase to cause the coalescence of particles from the aqueous phase as taught in U.S. Pat. Nos. 4,589,330 or 4,818,542. Preferred polymers for such preparations are natural or synthetic copolymers or polymers selected from the group consisting of gelatin agar, starch, arabinogalactan, albumin, collagen, polyglycolic acid, polylactic acid, glycolide-L(−) lactide poly(epsilon-caprolactone, poly(epsilon-caprolactone-CO-lactic acid), poly(epsilon-caprolactone-CO-glycolic acid), poly(β-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic acid, glycolide-L (−) lactide poly(epsilon-caprolactone), poly(epsilon-caprolactone-CO-lactic acid), and poly(epsilon-caprolactone-CO-glycolic acid). Solvents useful for dissolving the polymer include: water, hexafluoroisopropanol, methylenechloride, tetrahydrofuran, hexane, benzene, or hexafluoroacetone sesquihydrate.

The size of the nanoparticle can range from about 1 nm to about 1 µm. In certain embodiments, the nanoparticle is less than about 1 µm in diameter. In other embodiments, the nanoparticle is less than about 500 nm, less than about 400 nm, less than about 300 nm, less than about 200 nm, less than about 100 nm, or less than about 50 nm in diameter. In further embodiments, the nanoparticle is from about 1 nm to about 10 nm, 15 nm, 20 nm, 25 nm, 30 nm, 40 nm, 50 nm, 75 nm, or 100 nm in diameter. In specific embodiments, the nanoparticle is from about 1 nm to about 100 nm, about 1 nm to about 50 nm, about 1 nm to about 20 nm, or about 5 nm to about 20 nm.

The size of the complex can range from about 5 nm to about 1 µm. In certain embodiments, the complex is less than about 1 µm or alternatively less than 100 nm in diameter. In other embodiments, the complex is less than about 500 nm, less than about 400 nm, less than about 300 nm, less than about 200 nm, less than about 100 nm, or less than about 50 nm in diameter. In further embodiments, the complex is from about 10 nm to about 50 nm, or about 20 nm to about 75 nm, or about 25 nm to about 60 nm, or from about 30 nm to about 60 nm, or in one aspect about 55 nm.

E. Coupling Antigen-MHC Complex with the Nanoparticle

In order to couple the substrate or nanospheres to the antigen-MHC complexes the following techniques can be applied.

The binding can be generated by chemically modifying the substrate or nanoparticle which typically involves the generation of "functional groups" on the surface, said functional groups being capable of binding to an antigen-MHC complex, and/or linking the optionally chemically modified surface of the substrate or nanoparticle with covalently or non-covalently bonded so-called "linking molecules," followed by reacting the antigen-MHC complex with the nanoparticles obtained.

The term "linking molecule" means a substance capable of linking with the substrate or nanoparticle and also capable of linking to an antigen-MHC complex. In certain embodiments, the antigen-MHC complexes are coupled to the nanoparticle by a linker Non-limiting examples of suitable linkers include dopamine (DPA)-polyethylene glycol (PEG) linkers such as DPA-PEG-NHS ester, DPA-PEG-orthopyridyl-disulfide (OPSS) and/or DPA-PEG-Azide. Other linkers include peptide linkers, ethylene glycol, biotin, and strepdavidin.

The term "functional groups" as used herein before is not restricted to reactive chemical groups forming covalent bonds, but also includes chemical groups leading to an ionic interaction or hydrogen bonds with the antigen-MHC complex. Moreover, it should be noted that a strict distinction between "functional groups" generated at the surface and linking molecules bearing "functional groups" is not possible, since sometimes the modification of the surface requires the reaction of smaller linking molecules such as ethylene glycol with the nanosphere surface.

The functional groups or the linking molecules bearing them may be selected from amino groups, carbonic acid groups, thiols, thioethers, disulfides, guanidino, hydroxyl groups, amine groups, vicinal diols, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or nanoparticle. Nucleic acids can provide a link to affinity molecules containing themselves nucleic acid molecules, though with a complementary sequence with respect to the linking molecule.

A specific example of a covalent linker includes poly(ethylene)glycol (PEG) such as functionalized PEGs. As used herein, "functionalized PEGs" refer to PEG moieties including terminal functional group, non-limiting examples of which include amino, mercapto, thioether, carboxyl, and the likes. Non-limiting examples of functionalized PEG linkers on various nanoparticle cores are provided in Tables 1 and 2 attached hereto, e.g., the PEG linker thiol-PEG-NH$_2$ linker.

In certain embodiments, the linker as described herein has a defined size. In some embodiments, the linker is less that about 10 kD, less than about 5 kD, less than about 4.5 kD, less than about 4 kD, less than about 3.5 kD, less than about 3 kD, less than about 2.5 kD, less than about 2 kD, or less than about 1 kD. In further embodiments, the linker is from about 0.5 kD to about 5, 4.5, 4, 3.5, 3, 2.5, 2, 1.5, or 1 kD. In yet further embodiments, the linker is from about 1 to about, 4.5, 4, 3.5, 3, 2.5, 2, or 1.5 kD.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

The surface of the substrate or nanoparticle can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction. This binding reaction can be performed with substrate or nanosphere as directly obtained from the preparation process or after a pre-treatment (for instance with trimethylsilyl bromide). In the first case the phosphonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or nanosphere involves heating in a diole such as ethylene glycol. It should be noted that this treatment may be redundant if the synthesis already proceeded in a diol. Under these circumstances the synthesis product directly obtained is likely to show the necessary functional groups. This treatment is however applicable to substrate or nanoparticle that were produced in N- or P-containing complexing agents. If such substrate or particle are subjected to an after-treatment with ethylene glycol, ingredients of the reaction medium (e.g. complexing agent) still binding to the surface can be replaced by the diol and/or can be dealkylated.

It is also possible to replace N-containing complexing agents still bound to the particle surface by primary amine derivatives having a second functional group. The surface of the substrate or nanoparticle can also be coated with silica. Silica allows a relatively simple chemical conjugation of organic molecules since silica easily reacts with organic linkers, such as triethoxysilane or chlorosilane. The nanoparticle surface may also be coated by homo- or copolymers. Examples for polymerizable coupling agents are N-(3-aminopropyl)-3-mercaptobenzamidine, 3-(trimethoxysilyl) propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or nanoparticles containing oxidic transition metal compounds is conversion of the oxidic transition metal compounds by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance-via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or nanosphere surface are particularly suitable. Examples for linking molecules which can be non-covalently linked to core/shell nanospheres involve anionic, cationic or zwitter-ionic surfactants, acidic or basic proteins, polyamines, polyamides, polysulfone or polycarboxylic acid. The hydrophobic interaction between substrate or nanosphere and amphiphilic reagent having a functional reactive group can generate the necessary link. In particular, chain-type molecules with amphiphilic character, such as phospholipids or derivatized polysaccharides, which can be crosslinked with each other, are useful. The absorption of these molecules on the surface can be achieved by coincubation. The binding between affinity molecule and substrate or nanoparticle can also be based on non-covalent, self-organising bonds. One example thereof involves simple detection probes with biotin as linking molecule and avidin- or strepdavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or nanosphere or thereafter. Further, it is possible, by means of incubation, to effect a direct binding of molecules to correspondingly pre-treated substrate or nanoparticle (for instance by trimethylsilyl bromide), which display a modified surface due to this pre-treatment (for instance a higher charge or polar surface).

F. Protein Production

The present invention describes polypeptides, peptides, and proteins for use in various embodiments of the present invention. For example, specific peptides and their complexes are assayed for their abilities to elicit or modulate an immune response. In specific embodiments, all or part of the peptides or proteins of the invention can also be synthesized in solution or on a solid support in accordance with conventional techniques. Various automatic synthesizers are commercially available and can be used in accordance with known protocols. See, for example, Stewart and Young, Solid Phase Peptide Synthesis, $2^{nd}$ Ed., Pierce Chemical Co. 1, (1984); Tam et al., J. Am. Chem. Soc., 105:6442, (1983); Merrifield, Science, 232(4748):341-347, (1986); and Barany and Merrifield, The Peptides, Gross and Meinhofer (Eds.), Academic Press, NY, 1-284, (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are known to one skilled in the art and are briefly discussed herein. Examples of mammalian host cell lines include, but are not limited to ero and HeLa cells, other B- and T-cell lines, such as CEM, 721.221, H9, Jurkat, Raji, as well as cell lines of Chinese hamster ovary (CHO), W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

G. Nucleic Acids

The present invention may include recombinant polynucleotides encoding the proteins, polypeptides, peptides of the invention, such as those encoding antigenic peptides.

In particular embodiments, the invention concerns isolated nucleic acid segments and recombinant vectors incorporating nucleic acid sequences that encode an autoantigen and/or a MHC molecule. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

V. PHARMACEUTICAL COMPOSITIONS AND ADMINISTRATION

Provided herein are pharmaceutical compositions useful for the treatment of disease.

A. Pharmaceutical Compositions

The antigen-MHC nanoparticle complexes can be administered alone or in combination with a carrier, such as a pharmaceutically acceptable carrier in a composition. Compositions of the invention may be conventionally administered parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. The preparation of an aqueous composition that contains an antigen-MHC-nanoparticle complex that modifies the subject's immune condition will be known to those of skill in the art in light of the present disclosure. In certain embodiments, a composition may be inhaled (e.g., U.S. Pat. No. 6,651,655, which is specifically incorporated by reference in its entirety). In one embodiment, the antigen-MHC-nanoparticle complex is administered systemically.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms antigen-MHC-nanoparticle complex per administration. Suitable regimes for initial administration and boosters are also variable, but are typified by an initial administration followed by subsequent administrations.

In many instances, it will be desirable to have multiple administrations of a peptide-MHC-nanoparticle complex, about, at most about or at least about 3, 4, 5, 6, 7, 8, 9, 10 or more. The administrations will normally range from 2 day to twelve week intervals, more usually from one to two week intervals. Periodic boosters at intervals of 0.25-5 years, usually two years, may be desirable to maintain the condition of the immune system. The course of the administrations may be followed by assays for inflammatory immune responses and/or autoregulatory T cell activity.

In some embodiments, pharmaceutical compositions are administered to a subject. Different aspects of the present invention involve administering an effective amount of a antigen-MHC-nanoparticle complex composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier may be a solvent or dispersion medium containing, for example, water, ethanol, polyol (for example, glycerol, propylene glycol, and liquid poly(ethylene glycol), and the like, suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization. Sterilization of the solution will be done in such a way as to not diminish the therapeutic properties of the antigen-MHC-nanoparticle complex. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterilized solution thereof. One such method of sterilization of the solution is sterile filtration, however, this invention is meant to include any method of sterilization that does not significantly decrease the therapeutic properties of the antigen-MHC-nanoparticle complexes. Methods of sterilization that involve intense heat and pressure, such as autoclaving, may compromise the tertiary structure of the complex, thus significantly decreasing the therapeutic properties of the antigen-MHC-nanoparticle complexes.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

B. Combination Therapy

The compositions and related methods of the present invention, particularly administration of an antigen-MHC-nanoparticle complex, may also be used in combination with the administration of traditional therapies. These include, but are not limited to, Avonex (interferon beta-1a), Betaseron (interferon beta-1b), Copaxone (glatiramer acetate), Novantrone (mitoxantrone), Rebif (interferon beta-1a), Tysabri (natalizumab), Gilenya (fingolimod), Glatiramer, steroids, Cytoxan, Imuran, Baclofen, deep brain stimulation, Ampyra (dalfampridine), acupuncture, and physical therapy.

When combination therapy is employed, various combinations may be employed, for example antigen-MHC-nanoparticle complex administration is "A" and the additional agent is "B":

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A/ | B/B/A/A |
| B/A/B/A | B/A/A/B | A/A/A/B | B/A/A/A | A/B/A/A | A/A/B/A |

Administration of the peptide-MHC complex compositions of the present invention to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

C. In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present invention, the compositions may be administered either in vitro, ex vivo, or in vivo. In certain in vitro embodiments, autologous T cells are incubated with compositions of this invention. The cells or tissue can then be used for in vitro analysis, or alternatively for ex vivo administration.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the invention. Changes therein and other uses which are encompassed within the spirit of the invention as defined by the scope of the claims will occur to those skilled in the art.

Example 1

Preparation and Analysis of pMHC Nanoparticles.
pMHC Production

Two different methods were used to express recombinant pMHC class I complexes. The first involved re-folding MHC class I heavy and light chains expressed in bacteria in the presence of peptide, followed by purification via gel filtration and anion exchange chromatography, as described (Garboczi, D. N. et al. (1992) Proc Natl. Acad Sci USA 89:3429-3433; Altman, J. D. et al. (1996) Science 274:94-96). The second involved expressing MHC class I complexes at high yields in lentiviral-transduced freestyle CHO cells as single chain constructs in which the peptide-coding sequence, the MHC class I light and heavy chains are sequentially tethered with flexible GS linkers (Yu, Y. Y. et al. (2002) J Immunol 168:3145-3149) followed by a carboxy-terminal linker encoding a BirA site, a 6xHis tag (SEQ ID NO: 70) ending with a free Cys. The secreted proteins were purified from culture supernatants using nickel columns and anion exchange chromatography and used directly for NP coating or biotinylated to produce pMHC tetramers using fluorochrome-conjugated streptavidin. Tetramers generated using representative single-chain pMHC complexes encoding the $IGRP_{206-214}$ autoantigenic peptide or its mimic NRP-V7 efficiently bind to cognate monoclonal autoreactive CD8+ T-cells but not to their polyclonal counterparts (not shown), as determined by flow cytometry.

Recombinant pMHC class II monomers were initially purified from Drosophila SC2 cells transfected with constructs encoding I-Aβ and I-Aα chains carrying c-Jun or c-Fos leucine zippers, respectively, and a BirA and 6xHis tags (SEQ ID NO: 70) as previously described (Stratmann, T. et al. (2000) J Immunol 165:3214-3225, Stratmann, T. et al. (2003) J. Clin. Invest. 112:3214-3225). As the yields of this approach were generally low and time-consuming, Applicant developed an expression system in freestyle CHO cells transduced with lentiviruses encoding a monocistronic message in which the peptide-IAβ and IAα chains of the complex are separated by the ribosome skipping P2A sequence (Holst, J. et al. (2006) Nat Protoc 1:406-417). As with the single chain pMHC class I constructs described above, a linker encoding a BirA site, a 6xHis tag (SEQ ID NO: 70) and a free Cys was added to the carboxyterminal end of the construct. The self-assembled pMHC class II complexes were purified from the cell culture supernatants by nickel chromatography followed by anion exchange and used for coating onto NPs or processed for biotinylation and tetramer formation as described above. pMHC class II tetramers generated using a representative pMHC class II complex encoding the 2.5mi autoantigenic peptide are specifically and efficiently bound by cognate monoclonal autoreactive CD4+ T-cells, as determined by flow cytometry.

pMHC Tetramer Staining

PE-conjugated TUM-H-2K$^d$, NRP-V7-H-2K$^d$, IGRP$_{206-214}$-H-2K$^d$, HEL$_{14-22}$/IA$^{g7}$ and BDC2.5mi/IA$^{g7}$ tetramers were prepared using biotinylated pMHC monomers as described (Stratmann, T. et al. (2000) J Immunol 165:3214-3225; Stratmann, T. et al. (2003) J. Clin. Invest. 112:3214-3225; Amrani, A. et al. (2000) Nature 406:739-742). Peripheral blood mononuclear cells, splenocytes and lymph node CD8+ or CD4+ T-cells were stained with tetramer (5 ug/mL) in FACS buffer (0.1% sodium azide and 1% FBS in PBS) for 1 h at 4° C., washed, and incubated with FITC-conjugated anti-CD8α or anti-CD4 (5 μg/mL) and PerCP-conjugated anti-B220 (2 μg/mL; as a 'dumb' gate) for 30 min at 4° C. Cells were washed, fixed in 1% PFA/PBS and analyzed by FACS.

NP Synthesis

Gold nanoparticles (GNPs) were synthesized using chemical reduction of gold chloride with sodium citrate as described (Perrault, S. D. et al. (2009) Nano Lett 9:1909-1915). Briefly, 2 mL of 1% of HAuCl$_4$ (Sigma Aldrich) was added to 100 mL H$_2$O under vigorous stirring and the solution heated in an oil bath. Six (for 14 nm GNPs) or two mL (for 40 nm GNPs) of 1% Na Citrate were added to the boiling HAuCl$_4$ solution, which was stirred for an additional 10 min and then cooled down to room temperature. GNPs were stabilized by the addition of 1 uMol of thiol-PEG linkers (Nanocs, Mass.) functionalized with —COOH or —NH$_2$ groups as acceptors of pMHC (Tables 1 and 2). Pegylated GNPs were washed with water to remove free thiol-PEG, concentrated and stored in water for further analysis. NP density was via spectrophotometry and calculated according to Beer's law.

The SFP series iron oxide NPs (SFP IONPs) were produced by thermal decomposition of iron acetate in organic solvents in the presence of surfactants, then rendered solvent in aqueous buffers by pegylation (Xie, J. et al. (2007) Adv Mater 19:3163; Xie, J. et al. (2006) Pure Appl. Chem. 78:1003-1014; Xu, C. et al. (2007) Polymer International 56:821-826). Briefly, 2 mMol Fe(acac)$_3$ (Sigma Aldrich, Oakville, ON) were dissolved in a mixture of 10 mL benzyl ether and oleylamine and heated to 100° C. for 1 hr followed by 300° C. for 2 hr with reflux under the protection of a nitrogen blanket. Synthesized NPs were precipitated by addition of ethanol and resuspended in hexane. For pegylation of the IONPs, 100 mg of different 3.5 kDa DPA-PEG linkers (S1-S5 in Table 1; Jenkem Tech USA) were dissolved in a mixture of CHCl$_3$ and HCON(CH$_3$)$_2$ (DMF). The NP solution (20 mg Fe) was then added to the DPA-PEG solution and stirred for 4 hr at room temperature. Pegylated SFP NPs were precipitated overnight by addition of hexane and then resuspended in water. Trace amounts of aggregates were removed by high-speed centrifugation (20,000×g, 30 min), and the monodisperse SFP NPs were stored in water for further characterization and pMHC conjugation. The concentration of iron in IONP products was determined by spectrophotometry at A410 in 2N HCL. Based on the molecular structure and diameter of SFP NPs (Fe$_3$O$_4$; 8±1 nm diameter) (Xie, J. et al. (2007) Adv Mater 19:3163; Xie, J. et al. (2006) Pure Appl. Chem. 78:1003-1014), Applicant estimates that SFP solutions containing 1 mg of iron contain $5 \times 10^{14}$ NPs.

Applicant subsequently developed a new IONP design that allowed the formation, also by thermal decomposition but in a single step, of pegylated IONPs in the complete absence of surfactants (PF series IONPs). In this novel design, PEG molecules were used both as reducing reagents and as surfactants. In a typical reaction, 3 g PEG (2 kDa) were melted slowly in a 50 mL round bottom boiling flask at 100° C. and then mixed with 7 mL of benzyl ether and 2 mMol Fe(acac)$_3$. The reaction was vigorously stirred for one hr and heated to 260° C. with reflux for an additional two hr. The reaction mixture was cooled down to room temperature, transferred to a centrifugation tube and mixed with 30 mL water. Insoluble materials were removed by centrifugation at 2,000×g for 30 min. The free PEG molecules were removed by ultrafiltration through Amicon-15 filters (MWCO 100 kDa, Millipore, Billerica, Mass.). Applicant was able to generate IONPs with most, albeit not all of the PEG molecules tested (Table 1, P1-P5). The size of the IONPs varied depending on the functional groups of the PEG linkers used in the thermal decomposition reactions (Tables 1 and 2). The NPs could be readily purified using magnetic (MACS) columns (MILTENYI Biotec, Auburn, Calif.) or an IMag cell separation system (BD BioSciences, Mississauga, ON). The purified IONPs were stored in water or in various buffers (pH 5-10) at room temperature or at 4° C. without any detectable aggregation. NP density was calculated as described above for SFP NPs.

pMHC Conjugation of NPs pMHC conjugation to NPs produced with PEG linkers carrying distal —NH$_2$ or —COOH groups was achieved via the formation of amide bonds in the presence of 1-Ethyl-3-[3-dimethylaminopropyl]carbodiimide hydrochloride (EDC). NPs (GNP—C, SFP—C and PF—C, Table 2) with —COOH groups were first dissolved in 20 mM MES buffer, pH 5.5. N-hydroxysulfosuccinimide sodium salt (sulpha-NHS, Thermo scientific, Waltham, Mass., final concentration 10 mM) and EDC (Thermo scientific, Waltham, Mass., final concentration 1 mM) were added to the NP solution. After 20 min of stirring at room temperature, the NP solution was added drop-wise to the solution containing pMHC monomers dissolved in 20 mM borate buffer (pH 8.2). The mixture was stirred for additional 4 hr. To conjugate pMHCs to NH$_2$-functionalized NPs (GNP—N, SFP—N and PF—N, Table 2), pMHC complexes were first dissolved in 20 mM MES buffer, pH 5.5, containing 100 mM NaCl. Sulpha-NHS (10 mM) and EDC (5 mM) were then added to the pMHC solution. The activated pMHC molecules were then added to the NP solution in 20 mM borate buffer (pH 8.2), and stirred for 4 hr at room temperature.

Figure 1C:
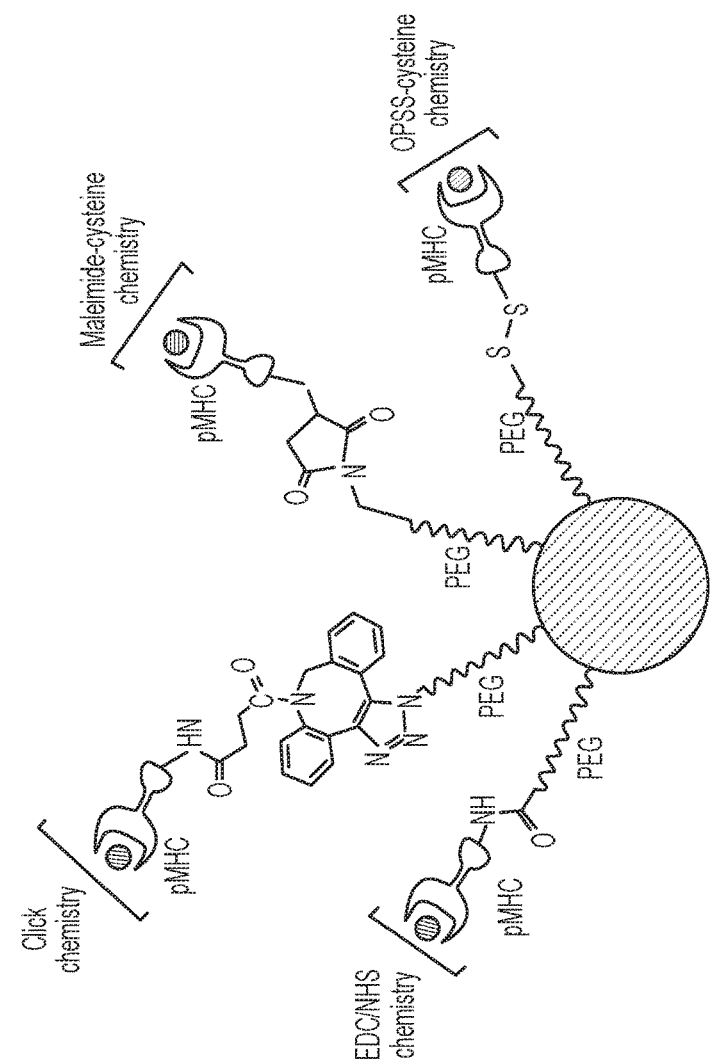
Figure 1C:
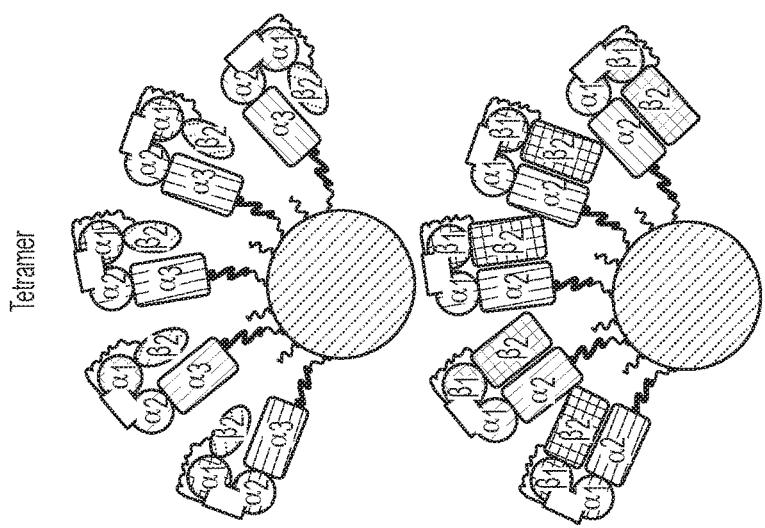

To conjugate pMHC to maleimide-functionalized NPs (SFP-M and PF-M, Table 2 and FIG. 1C), pMHC molecules were first incubated with Tributylphospine (TBP, 1 mM) for 4 hr at room temperature. pMHCs engineered to encode a free carboxyterminal Cys residue were then mixed with NPs in 40 mM phosphate buffer, pH 6.0, containing 2 mM EDTA, 150 mM NaCl, and incubated overnight at room temperature. pMHCs were covalently bound with NPs via the formation of a carbon-sulfide bond between meleimide groups and the Cys residue.

Click chemistry was used to conjugate pMHC or avidin to NPs functionalized with azide groups (SFP-Z, Table 2). For this reaction, pMHC or avidin molecules were first incubated with dibenzocyclooctyl (DBCO, Click Chemistry Tools, Scottdale, Ariz.) reagent for 2 hr at room temperature. Free DBCO molecules were removed by dialysis overnight. pMHC- or avidin-DBCO conjugates were then incubated with SFP-Z for 2 hr, resulting in formation of triazole bonds between pMHCs or avidin molecules and NPs.

Unconjugated pMHC complexes in the different pMHC-NP conjugating reactions were removed by extensive dialysis against PBS, pH 7.4, at 4° C. though 300 kDa molecular weight cut off membranes (Spectrum labs). Alternatively, pMHC-conjugated IONPs were purified by magnetic separation. The conjugated NPs were concentrated by ultrafiltration through Amicon Ultra-15 units (100 kDa MWCO) and stored in PBS.

Electron Microscopy, Dynamic Light Scattering, DLS and Small Angle Electro Beam Diffraction The core size and dispersity of unconjugated and pMHC-conjugated NPs were first assessed via transmission electron microscopy (TEM, Hitachi H7650). Dynamic light scattering (DLS) was used to determine the pMHC-NPs' hydrodynamic size, zeta potential and monodisperity using a ZetaSizer instrument (Malvern, UK). The chemical nature of the iron oxide core of the PF series of NPs was evaluated using small angle electro beam diffraction (SEBD).

Fourier Transformation Infrared spectroscopy

The surface chemical properties of the PF-series IONP designs were evaluated using Fourier Transformation Infrared spectroscopy (FTIR). The FTIR spectra of control PEG and PEG anchored on the PF-NP surface were obtained using a NICOLET FTIR spectrophotometer on an ATR (attenuated total reflection) mode. Each of the spectra was recorded as the average of 256 scans at 4 cm$^{-1}$ spectral resolution. The stretching vibration signatures of the PEG backbone C—O—C groups and their distal pMHC-acceptor functional groups were identified.

Agarose Gel Electrophoresis

To quickly evaluate changes on the NP charge as a function of pegylation or pMHC coating, NPs were subjected to electrophoresis on 0.8% agarose gels. Pegylated NPs migrated to negative or positive poles depending on the overall surface charge. Coomassie blue staining was done to confirm co-migration of the pMHCs with the NPs.

Native and Denaturing Polyacrylamide Gel Electrophoresis pMHC conjugated NPs were subjected to native-PAGE (10%) and SDS-PAGE (12%) analyses to confirm absence of free (unconjugated pMHC) in the pMHC-NP preparations and to confirm presence of intact trimolecular pMHC complexes on the NP's surface.

pMHC Valency Measurements

To evaluate the number of pMHC monomers conjugated onto individual NPs (pMHC valency), we measured the pMHC concentration of the pMHC-NP preps using different approaches, including Bradford assay (Thermo Scientific), amino acid analysis (HPLC-based quantification of 17 different amino acids in hydrolyzed pMHC-NP preparations) (University of Toronto), dot-ELISA and signature peptide analysis by mass spectrometry) and the values converted to ratios of pMHC molecular number to NP number. Briefly, in the "dot-ELISA" approach, pMHC-conjugated and unconjugated NPs and pMHC monomer solutions (as standards) were serially diluted in PBS and then absorbed to a PVDF membrane in a multiwell filter plate (PALL Corporation). The plate was allowed to partially dry at room temperature and then incubated with pMHC specific primary antibodies (i.e., anti-β2M and anti-K$^d$ antibodies for pMHC class I-coated NPs, clones 2M2 and SF1-1.1, BioLegend, San Diego, Calif.), followed by HRP- or AP-conjugated secondary antibodies. Upon development of the enzymatic color reactions, the contents of the wells were transferred to wells in a conventional ELISA plate and their absorbances measured at 450 nm using a plate reader. For the signature peptide mass spectrometry approach, pMHC-specific trypsin peptides (signature peptides TWTAADTAALITR (SEQ ID NO: 71) for K$^d$ complexes and AQNSELASTANMLR (SEQ ID NO: 72) for I-A$^{g7}$ complexes) were identified via mass spectrometry. The corresponding synthetic peptides were labeled with stable isotopes (AQUA peptide synthesis, Sigma Aldrich). The isotope-labeled peptides were then serially diluted to defined concentrations and mixed with pMHC-conjugated NPs for trypsin digestion. The mixtures were subjected to mass spectroscopy (Agilent QTOF6520) to quantify the ratios of isotope-labeled versus unlabeled signature peptides, as a read-out of pMHC concentration. Since the values generated by these different methods were similar, the Bradford assay (using unconjugated NPs as blanks) became the method of choice for ease and simplicity.

Agonistic Activity of pMHC-NPs In Vitro

FACS-sorted splenic CD8+ cells from TCR-TG mice ($2.5 \times 10^5$ cells/mL) were incubated with serially diluted pMHC conjugated or control NPs for 24-48 h at 37° C. The supernatants were assayed for IFNγ by ELISA. The cultured cells were pulsed with 1 mCi of [$^3$H]-thymidine and harvested after 24 h to measure [$^3$H] incorporation.

pMHC-NP Therapy

Cohorts of 10 wk-old female NOD mice were injected i.v. with pMHC-coated NPs in PBS twice a week for 5 wk (10 doses in total). Increases in the size of tetramer+CD8+ or CD4+ T-cell pools in blood, spleen, lymph nodes and/or marrow, as well as their phenotypic properties, were assessed by flow cytometry as described (Tsai, S. et al. (2010) Immunity 32:568-580) (and Clemente-Casares et al., submitted). In other experiments, mice displaying blood glucose levels >11 mM for 2 days were treated i.v. twice a wk with pMHC-NP and monitored for hyperglycemia until stably normoglycemic (for 4 wk). Animals were also assessed daily for glycosuria and given human insulin isophane (1 IU per day) s.c. if 3+.

Statistical Analyses

Data were compared by two-tailed Student's t, Mann-Whitney U, Chi-Square, or two-way ANOVA tests. Statistical significance was assumed at $P<0.05$.

Mice

NOD/Lt mice were from the Jackson Lab (Bar Harbor, Me.). 17.4α/8.3 (8.3-NOD), 17.6α/8.3α (17.6-NOD) and BDC2-5-NOD mice have been described (Katz, J. D. et al. (1993) Cell 74:1089-1100; Verdaguer, J. et al. (1997) J Exp Med 186:1663-1676; Han, B. et al. (2005) J Clin Invest 115:1879-1887).

Example 2

Production of T1D-Relevant pMHC Class II

Figure 2:
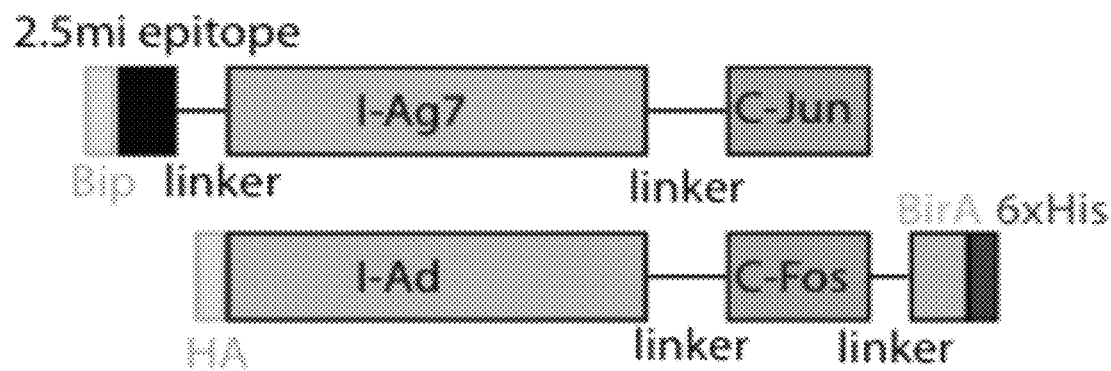
FIG. 2 shows the structure of a typical pMHC class II monomer (top) and a representative FACS profile of cognate CD4+ T-cells stained with the corresponding pMHC tetramer or left unstained.
Figure 2:
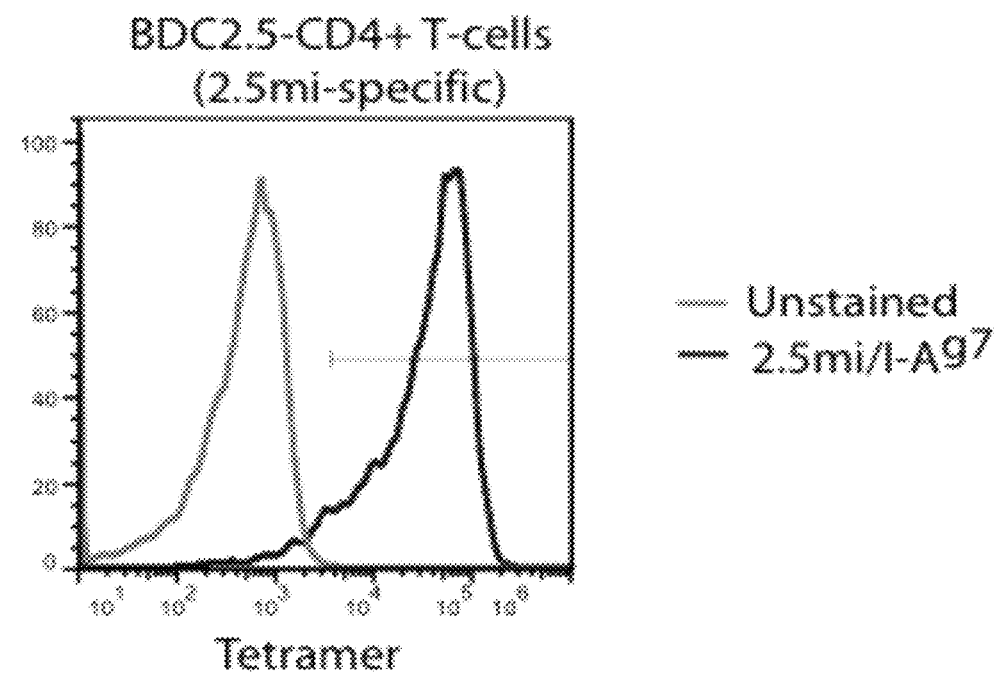

Several different T1D-relevant and irrelevant (i.e., negative control) peptide/I-A$^{g7}$ complexes were produced in eukaryotic (S2 or CHO cells). Studies using tetramers generated from these monomer preps confirm that these monomers are secreted into the supernatant as properly folded pMHC complexes. FIG. 2 provides an example.

Figure 3A:
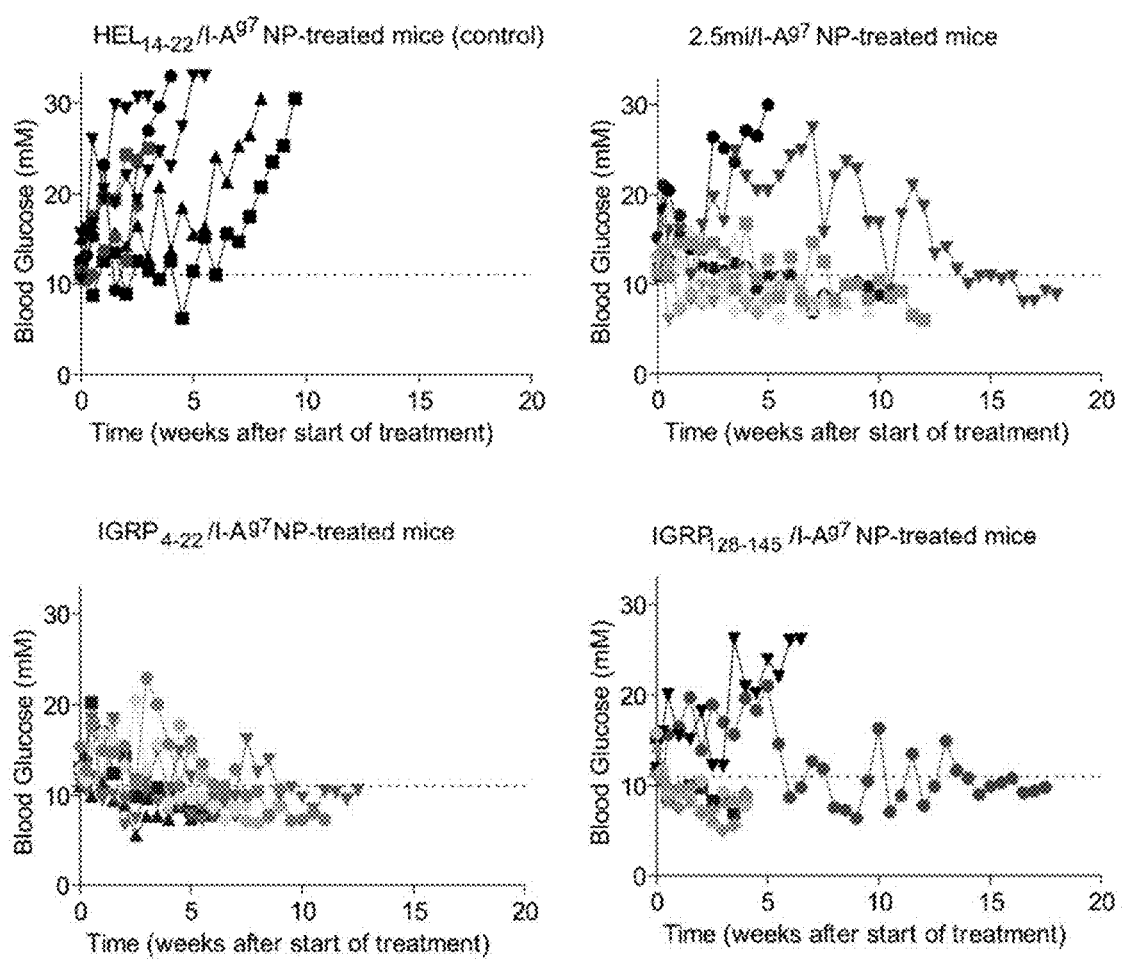
FIGS. 3A-3B show different T1D-relevant pMHC class II-NPs reverse hyperglycemia in newly diabetic NOD mice.
Figure 3B:
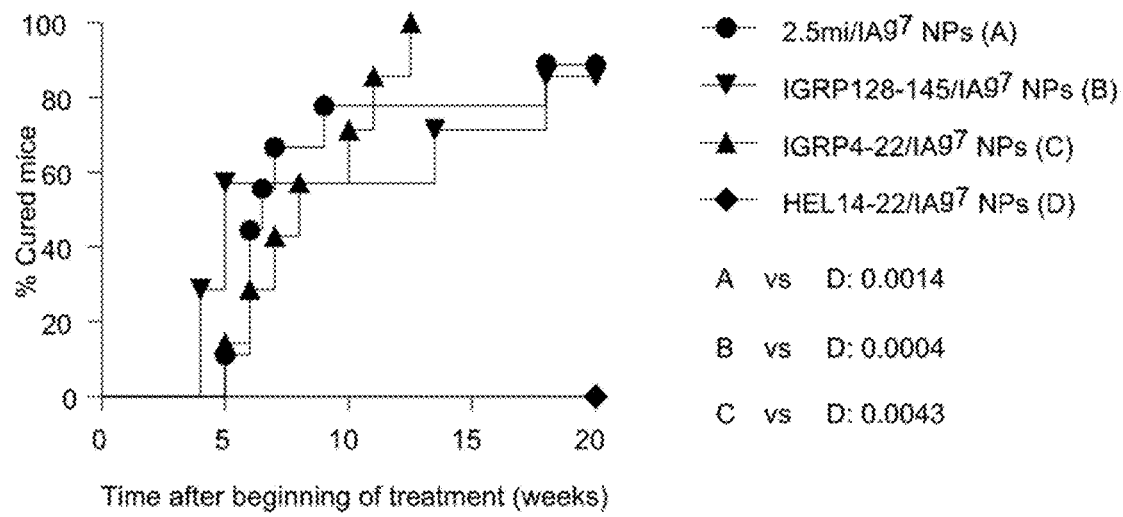
Figure 4:
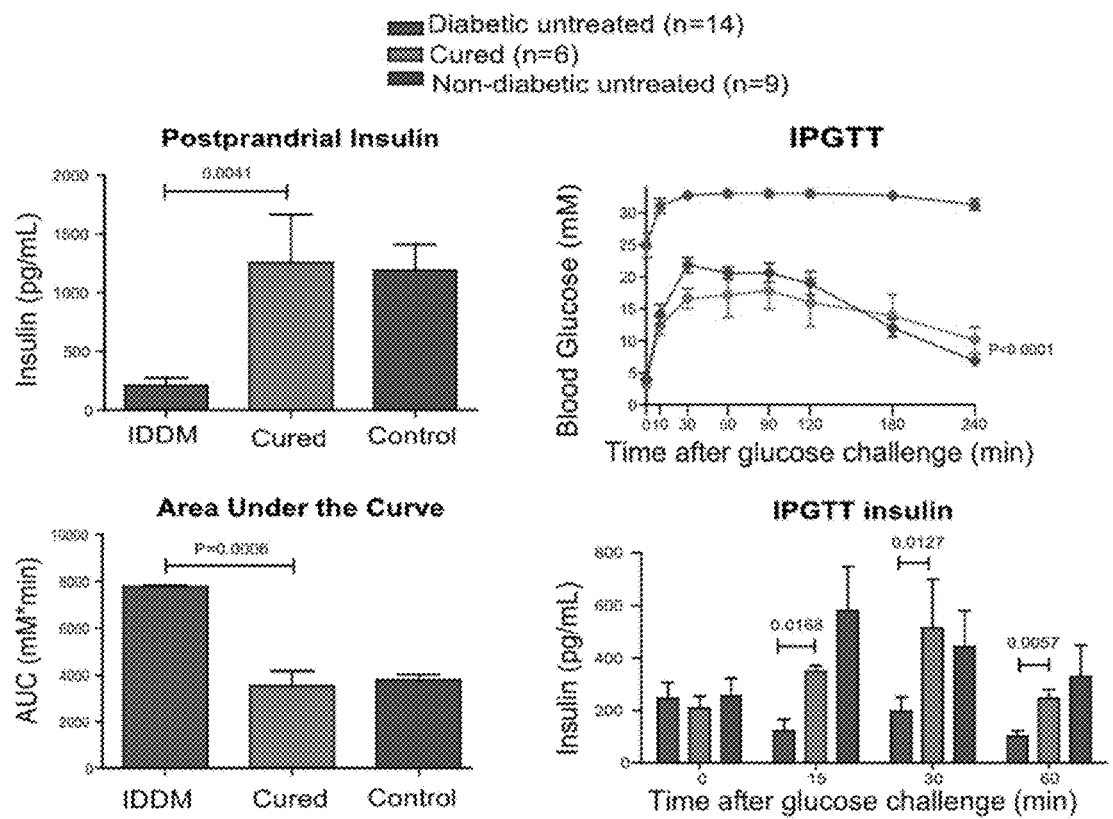
FIG. 4 shows intraperitoneal glucose-tolerance tests (IPT-GTTs) and insulin-production capacity in long-term cured mice. IDDM, diabetic untreated mice; Cured, mice with normoglycemia at 50 wk of age (>30 wk after treatment withdrawal); Control, age-matched non-diabetic untreated mice (50 wk-old).

Reversal of Hyperglycemia in NOD Mice by Treatment with T1D-Relevant pMHC Class II-NPs Diabetic NOD mice were treated twice a wk with 7.5 μg of pMHC class II-coated-NPs. Mice were considered cured when normoglycemic for 4 wk, at which point treatment was withdrawn. As shown in FIG. 3, whereas 2.5mi/I-A$^{g7}$-, IGRP$_{128-145}$/I-A$^{g7}$-, and IGRP$_{4-22}$/I-A$^{g7}$-NPs reversed hyperglycemia in 90-100% of mice (n=29 mice), treatment with HEL$_{14-22}$/I-A$^{g7}$-NPs (a foreign pMHC) had no effect. Intraperitoneal glucose tolerance tests (IPGTTs) in cured mice >30 wk after treatment withdrawal yielded curves that were very similar to those in age-matched non-diabetic untreated controls and significantly different than those obtained in untreated acutely diabetic NOD mice (FIG. 4). Thus, NPs coated with T1D-relevant pMHC class II restore glucose homeostasis in diabetic mice.

Figure 5:
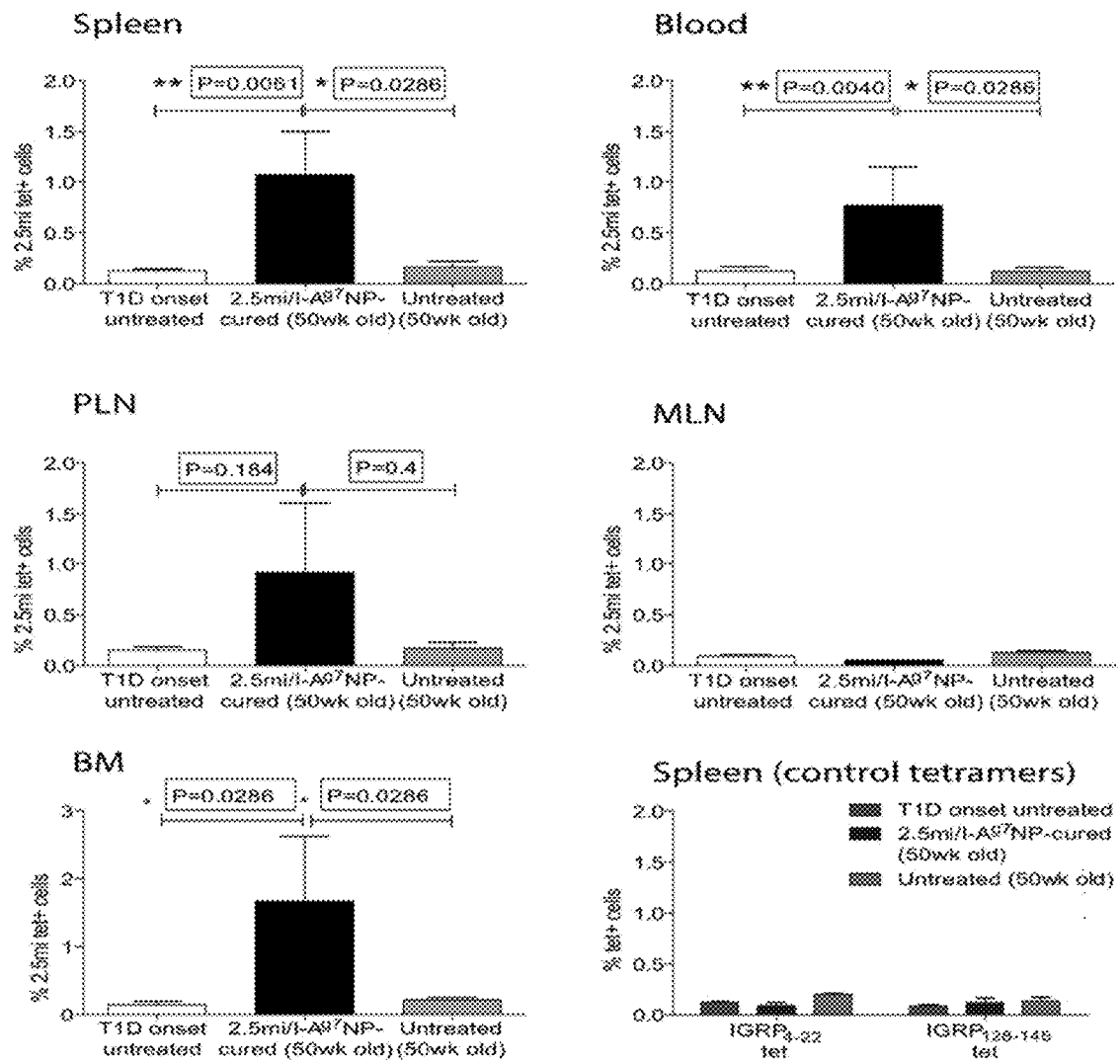
FIG. 5 shows that T1D-relevant pMHC class II-NPs expand cognate autoreactive CD4+ T-cells. Data correspond to mice treated with 2.5mi/I-Ag7-NPs. Bottom right, expansion is specific for the pMHC on the NPs, as mice treated with 2.5mi/I-Ag7-NPs did not show increased percentages of two other autoreactive CD4+ T-cell specificities. PLN, pancreatic lymph nodes; MN, mesenteric lymph nodes; BM, bone marrow (a reservoir of memory T-cells).
Figure 6:
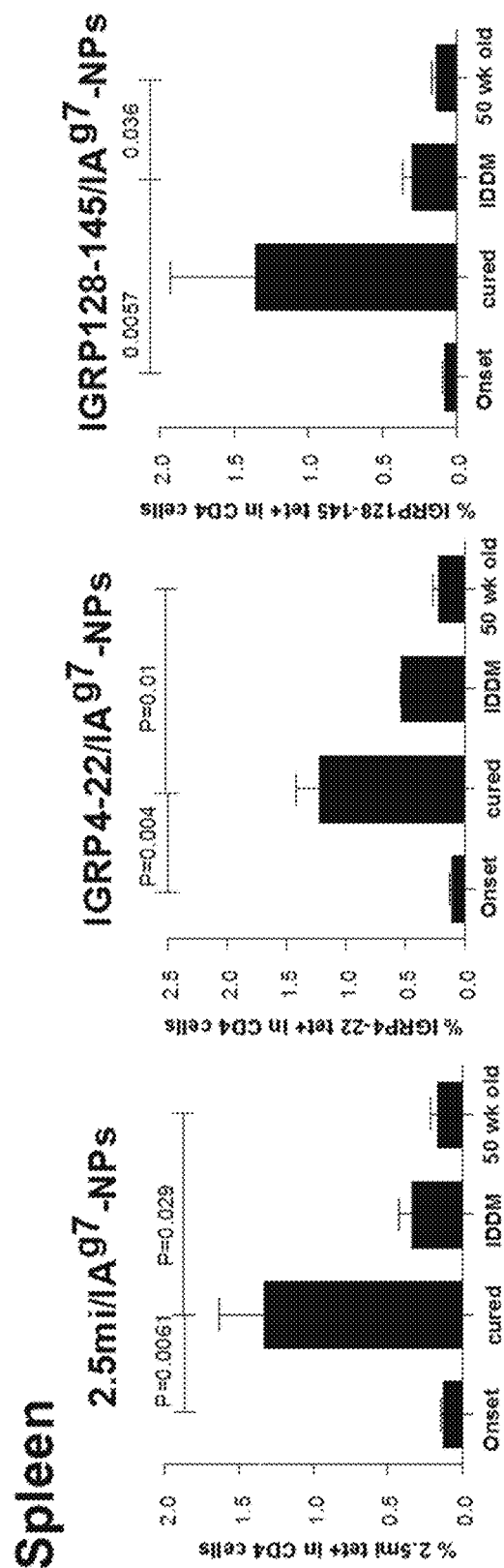
FIG. 6 shows that T1D-relevant pMHC class II-NPs expand cognate autoreactive CD4+ T-cells. Expansion is shown for spleen but similar patterns are seen in the pancreatic lymph nodes, blood and marrow. "Onset" correspond to pre-treatment values; "Cured" are mice rendered normoglycemic with pMHC-NP (analyzed at >30 wk of treatment withdrawal); "IDDM" are mice that relapsed upon treatment withdrawal (~25%); "50 wk-old" corresponds to age-matched untreated non-diabetic controls.
Figure 7:
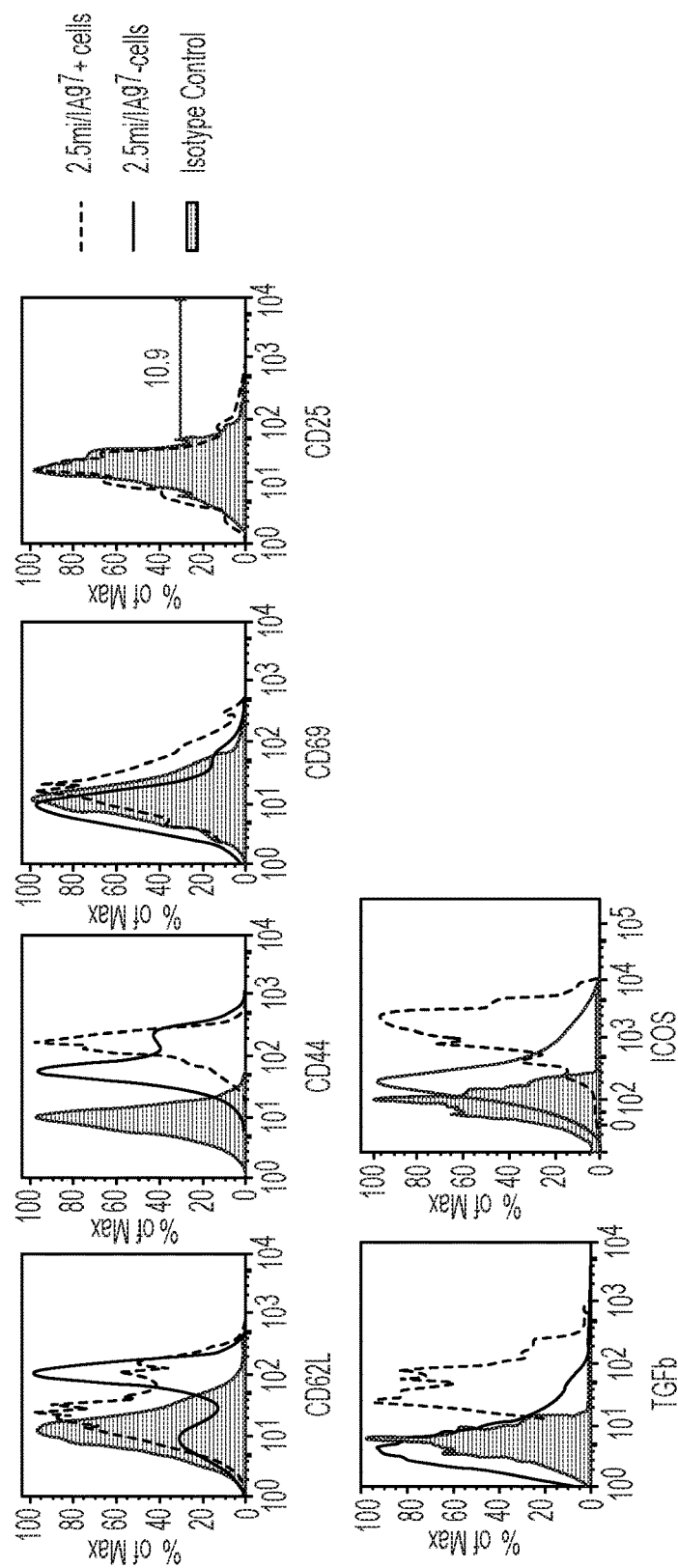
FIG. 7 shows that T1D-relevant pMHC class II-NPs expand cognate memory-like T-regulatory-1 ("Tr1 or TR1") cells.
Figure 7:
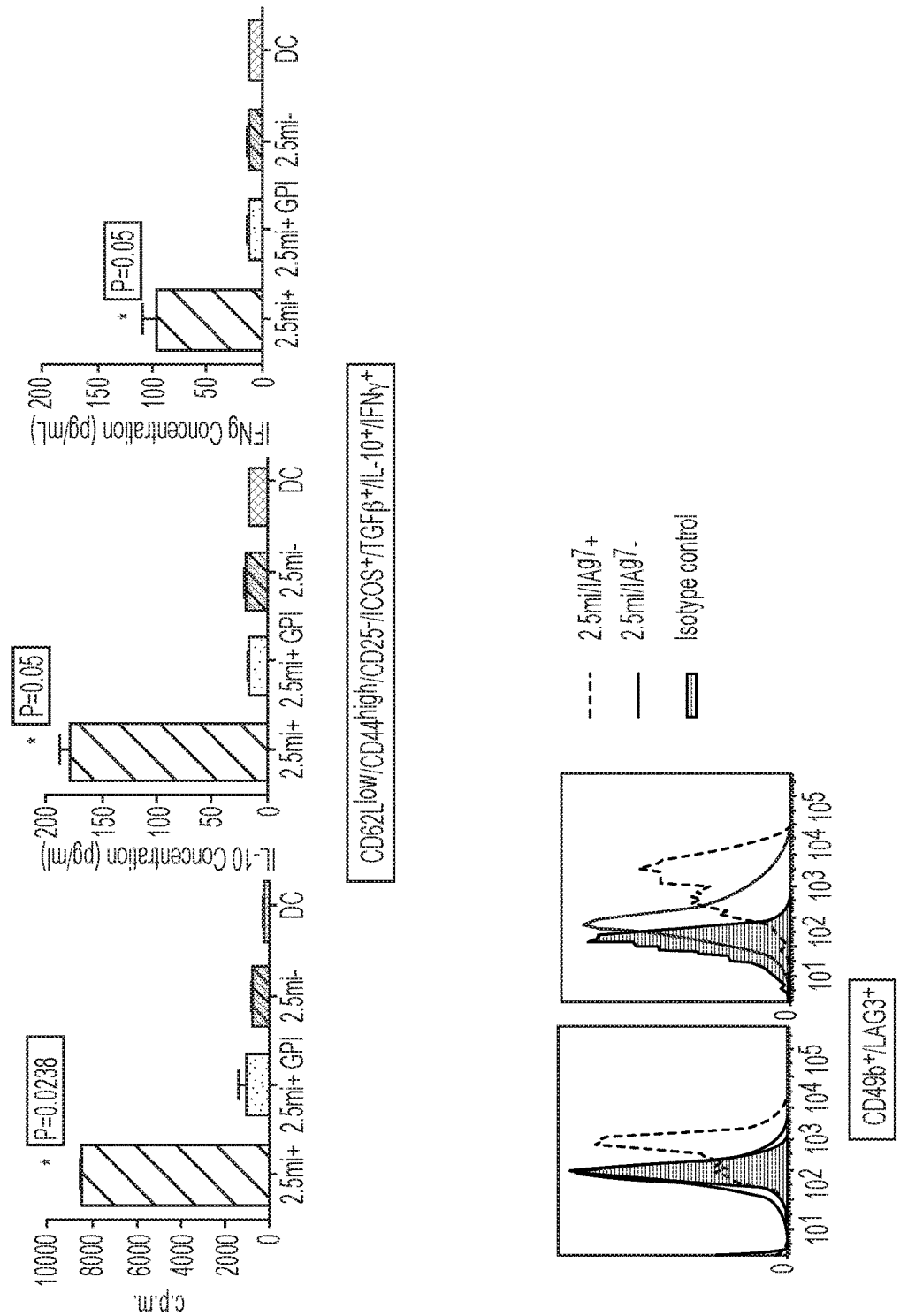

T1D-Relevant pMHC Class II-NPs Expand Cognate Memory TR1 Autoregulatory CD4+ T Cells Studies of blood, spleens, pancreatic lymph nodes (PLNs), mesenteric lymph nodes (MLNs) and bone marrow of 50 wk-old diabetic mice that had been rendered normoglycemic by treatment with 2.5mi/I-A$^{g7}$-NPs revealed significantly increased percentages of 2.5mi/I-A$^{g7}$ tetramer+ CD4+ cells, as compared to mice studied at diabetes onset or age-matched non-diabetic untreated animals (FIG. 5). CD4+ T-cell expansion was antigen-specific (FIG. 5). The tempo, magnitude and distribution of expansion were similar for the three T1D-relevant pMHC class II-NPs tested (FIG. 6). Phenotypic analyses of the NP-expanded tetramer+ cells vs. tetramer– cells in all these cohorts revealed a memory-like TR1 phenotype (FIG. 7, top) with co-expression of the TR1-specific markers described recently (Gagliani, N. et al. (2013) Nature Medicine 19:739-746) (FIG. 7, bottom): CD62$^{low}$/CD44$^{high}$/ICOS$^+$/CD25$^-$/FoxP3$^-$/surface TGFβ$^+$/CD49b$^+$/LAG3$^+$ That these cells were not FoxP3+ was confirmed in NOD mice expressing FoxP3 promoter-eGFP, in which all pMHC-NP-expanded cells were eGFP-negative (not shown).

Figure 8:
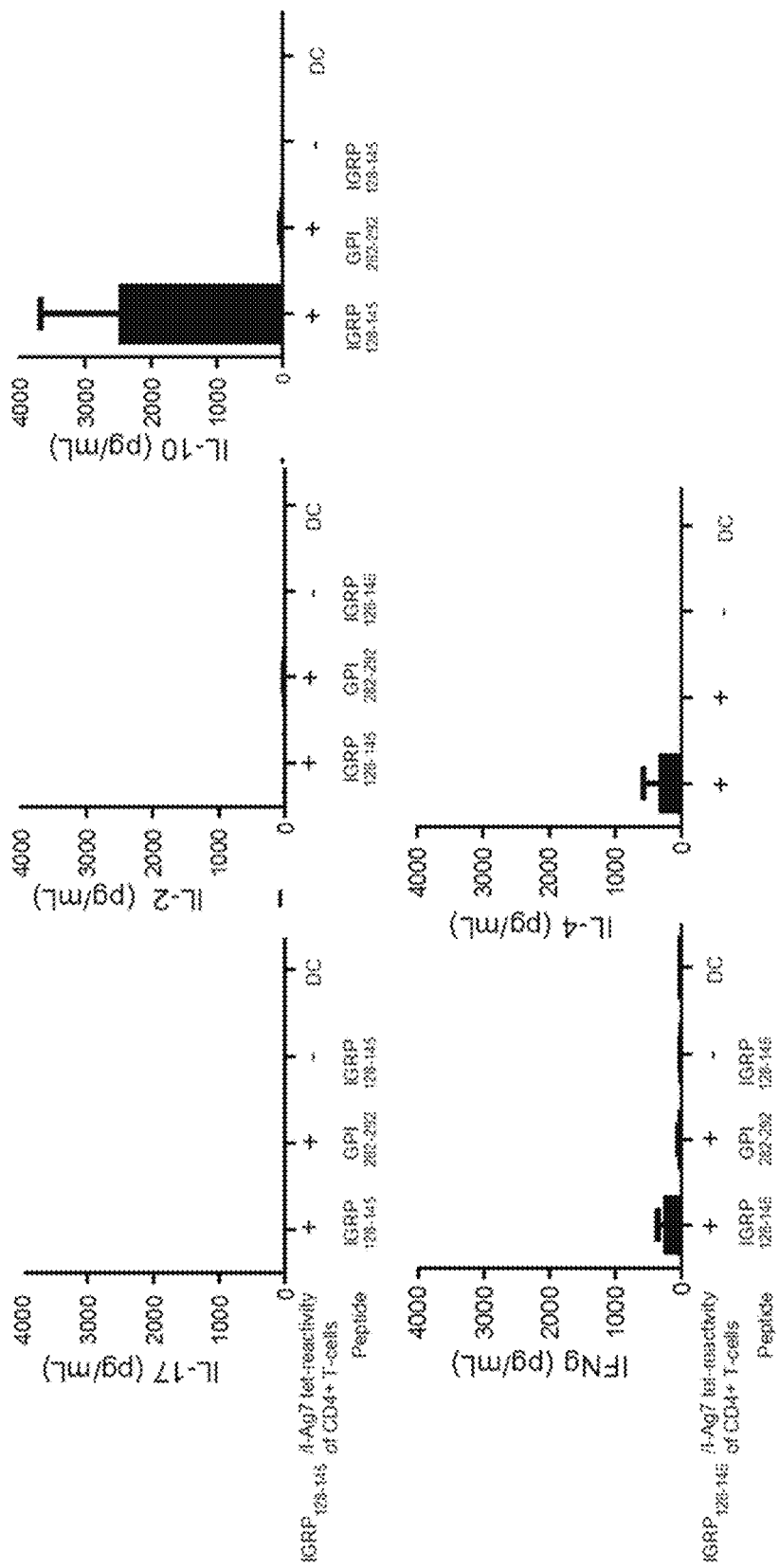
FIG. 8 shows that the autoreactive CD4+ T-cells expanded by pMHC class II-NP are IL-10 producers. $IGRP_{126-145}/I-A^{g7}$ tetramer+ cells from mice treated with $IGRP_{126-145}/I-A^{g7}$-NPs or control NPs were sorted, challenged with cognate and non-cognate peptides and the sups assayed for cytokine content with luminex technology.

Consistent with these phenotypic data, tetramer+ CD4+ cells sorted from pMHC-NP-treated mice responded to DCs pulsed with cognate peptide by almost exclusively secreting IL-10 and, to a lower extent, IFNγ (FIG. 8 and not shown). Importantly, purified CD4+ but not CD8+ T cells from pMHC-NP-treated donors inhibited T1D in NOD.scid mice transferred with diabetogenic splenocytes and hosts treated with pMHC class II-NPs were 100% protected for >100 days (not shown).

Figure 9:
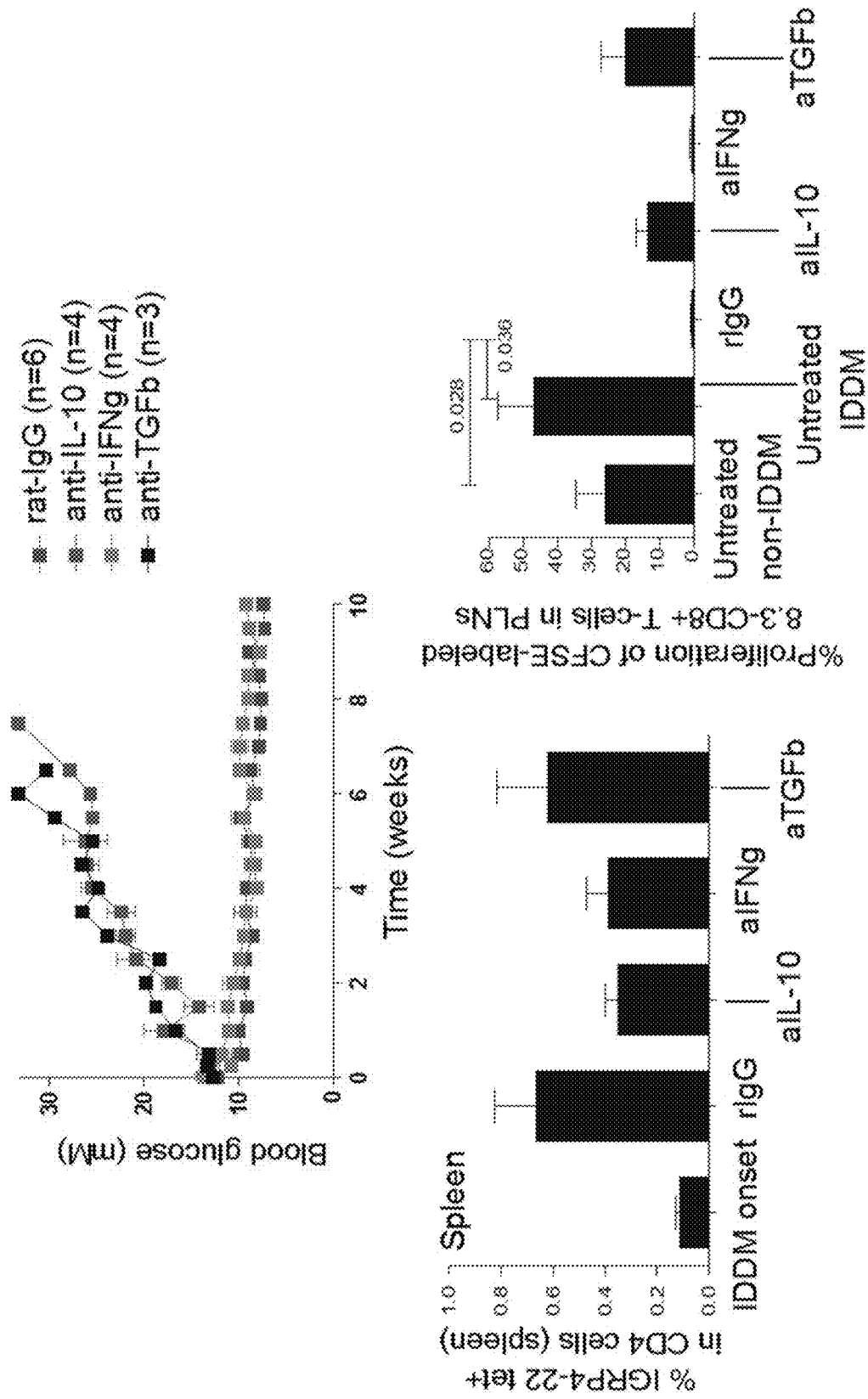
FIG. 9 shows that pMHC class II-NPs reverse hyperglycemia in an IL-10 and TGFb-dependent manner.

These pMHC class II-NP-expanded tetramer+ cells, unlike their tetramer– counterparts, inhibited the proliferation of non-cognate T-cells to peptide-pulsed DCs (presenting the peptides targeted by both the responder and tetramer+ TR1 cells). Addition of an anti-IL10 or anti-TGFβ mAbs to the cultures partially inhibited the suppression, versus cultures receiving anti-IFNγ or rat-IgG (not shown). Most importantly, studies of diabetic mice treated with IGRP$_{4-22}$ or 2.5mi/I-A$^{g7}$-NPs and blocking anti-IL-10, anti-TGFβ or anti-IFNγ mAbs or rat-IgG (FIG. 9) indicate that restoration of normoglycemia by pMHC class II-NPs requires IL-10 and TGFβ but not IFNγ. However, studies in spontaneously diabetic NOD.Il10$^{-/-}$ and NOD.Ifng$^{-/-}$ mice suggest that expression of both IL-10 and IFNγ are necessary for development of the TR1 cells that expand in response to pMHC class II-NPs; in these mice, pMHC-NP therapy expanded Th2-like cells (NOD.Ifng$^{-/-}$) or IFNγ+/IL-4$^+$/IL10$^-$ cells (NOD.Il10$^{-/-}$ mice). Studies in diabetic IGRP$^{-/-}$ NOD mice (unable to prime IGRP-reactive T cells) showed that these mice did not respond to IGRP$_{4-22}$/I-A$^{g7}$-NPs (there was no T cell expansion or restoration of normoglycemia) because these mice lacked IGRP$_{4-22}$-primed cells. In contrast, all the diabetic IGRP$^{-/-}$ NOD mice treated with 2.5mi/I-A$^{g7}$-NPs cured (not shown). Thus, pMHC class II-NPs, like pMHC class I-NPs, operate by expanding disease-primed regulatory memory, but cannot prime these responses de novo because they lack co-stimulatory signals.

Figure 10A:
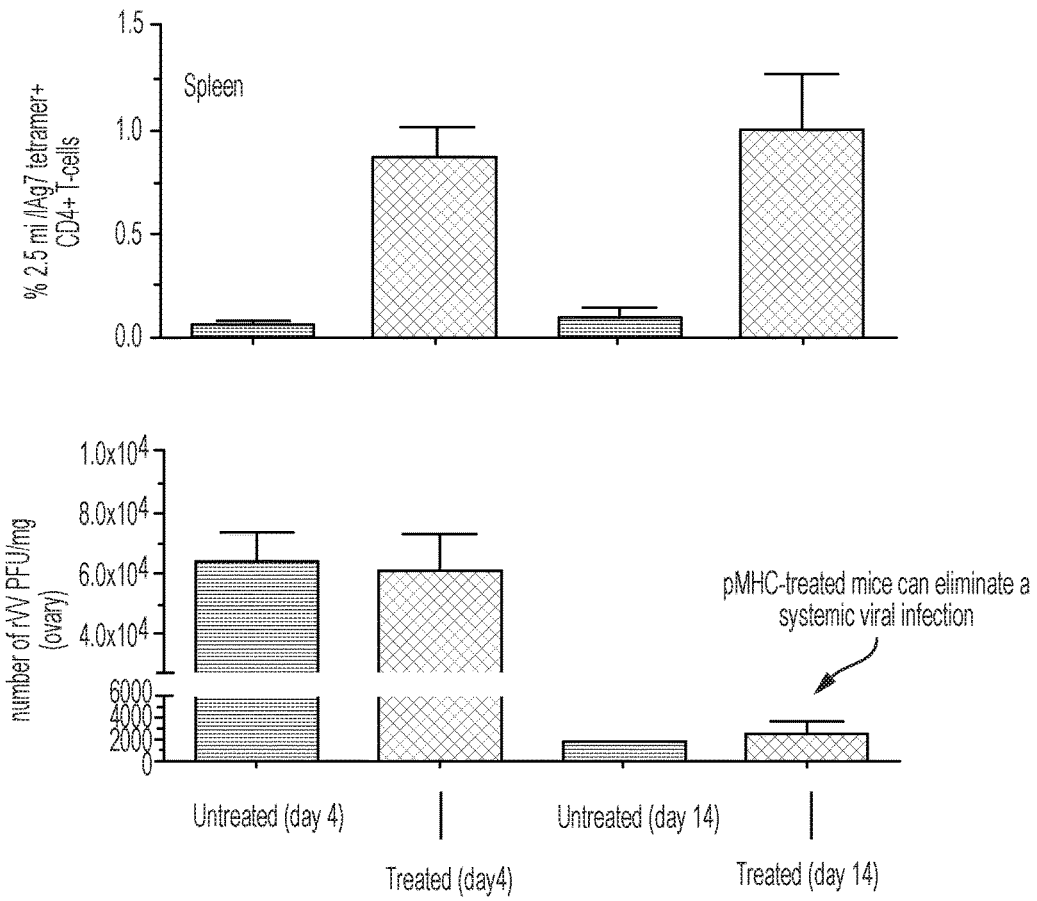
FIGS. 10A-10B show that pMHC class II-NP therapy does not compromise systemic immunity.
Figure 10B:
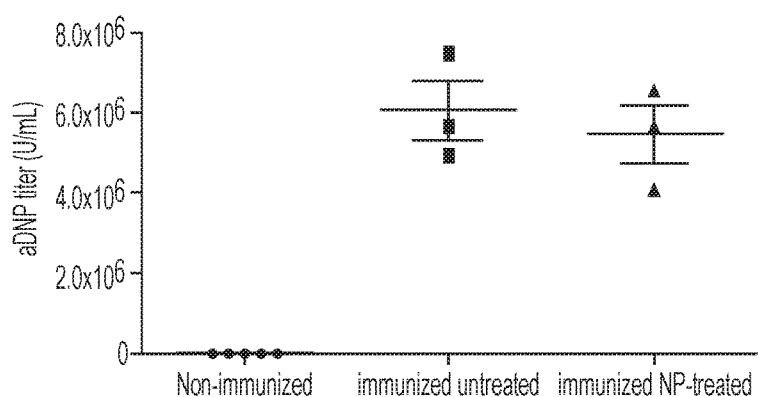

Lastly, studies with vaccinia virus (rVV) showed that pMHC class II-NP-treated NOD mice can readily clear an acute viral infection (FIG. 10A). In agreement with this, treated mice can mount antibody responses against a model antigen in adjuvant (FIG. 10B).

Example 3

Monospecific pMHC Class II-NPs Decrease the Severity of EAE

Figure 11:
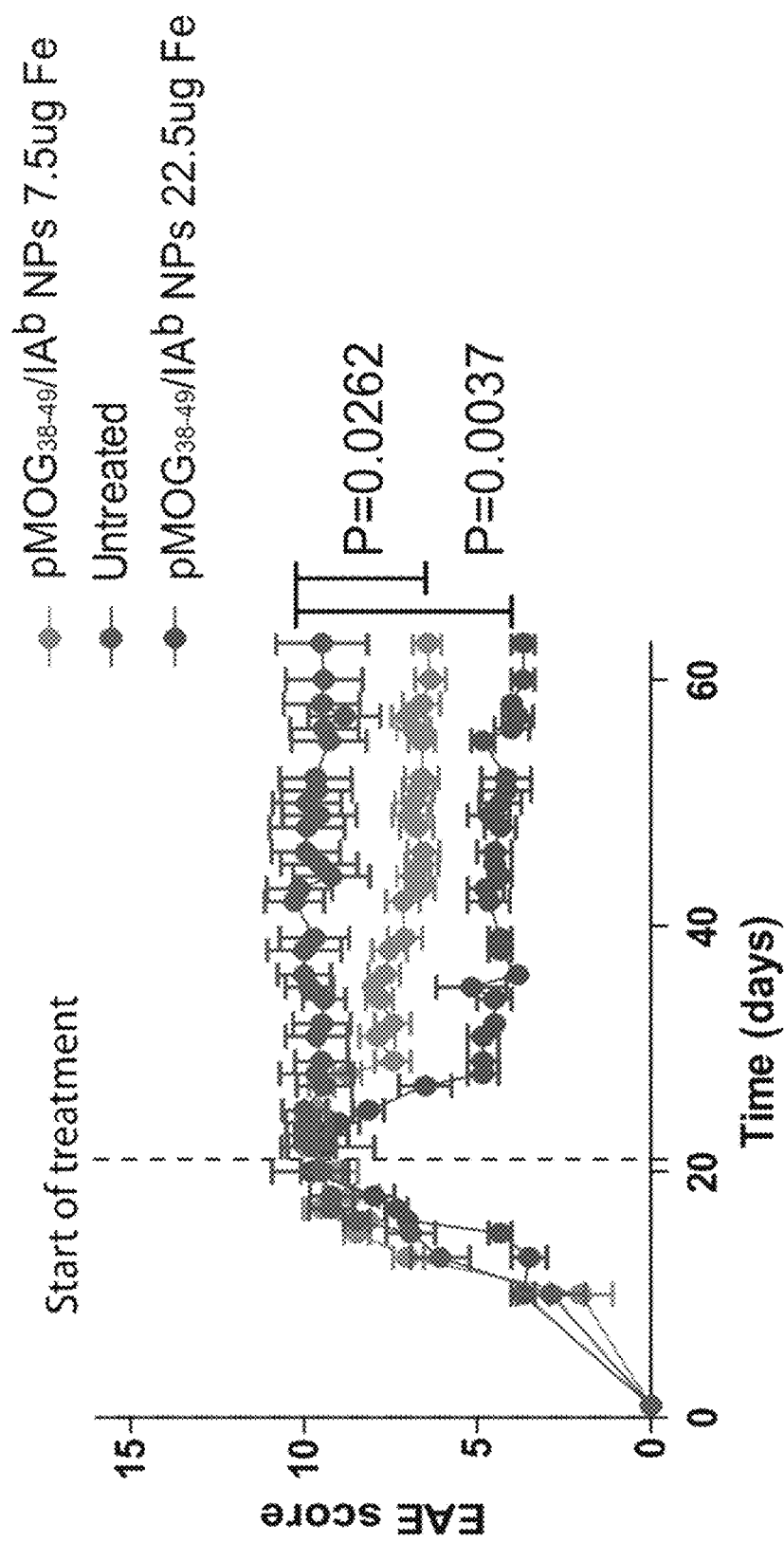
FIG. 11 shows that pMHC class II-NP therapy reduces the severity of established EAE in C57BL/6 mice. B6 mice were immunized with pMOG35-55 in CFA and treated with pertussis toxin i.v. Mice were scored for signs of EAE using established criteria over a 15-point scale. Affected mice were treated with two weekly doses of 7.5-22.5 ug of $pMOG_{38-49}/IA^{b}$-coated NPs, beginning 21 days after immunization.

Applicant then tested the therapeutic potential of a pMHC class II-based nanomedicine in Experimental Autoimmune Encephalomye-litis (EAE). This model was utilized in the most stringent test possible: to investigate if pMHC-NPs can reverse established EAE as opposed to prevent or blunt its development. This is not a trivial issue. A recent review of interventions in EAE shows that <1% of over 400 studies initiated treatment 21 days after EAE induction (Holst, J. et al. (2006) Nat Protoc 1:406-417); the reported data were obtained in mice in which treatment was initiated 21 days after EAE induction and improved disease scores in a dose-dependent manner (FIG. 11).

Example 4

Synthesis and Quality Control of pMHC Class II-Coated NPs

Figure 12A:
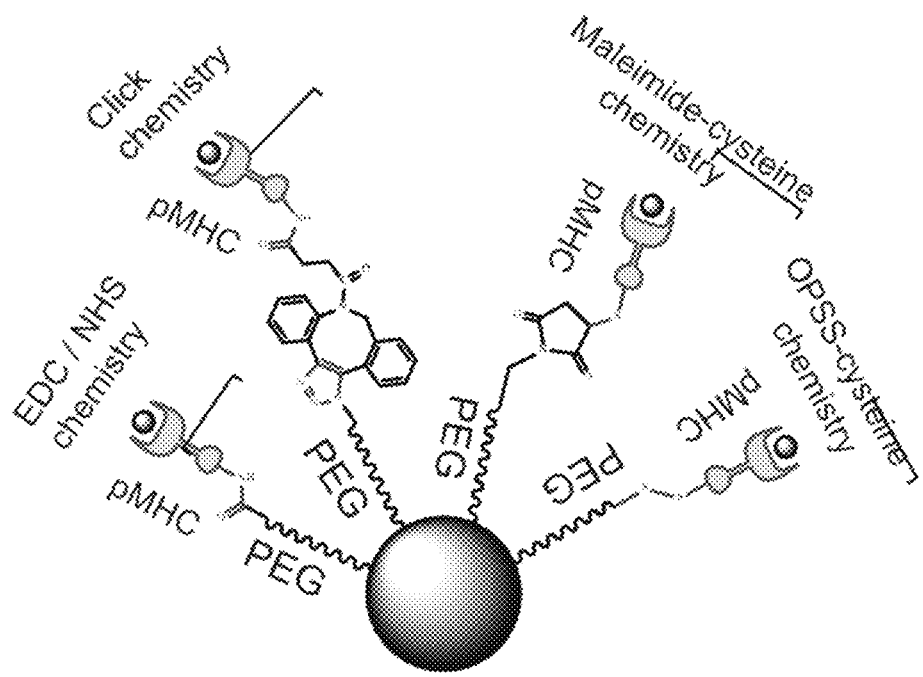
FIGS. 12A-12C show structure and properties of pMHC class II-NPs.
Figure 12B:
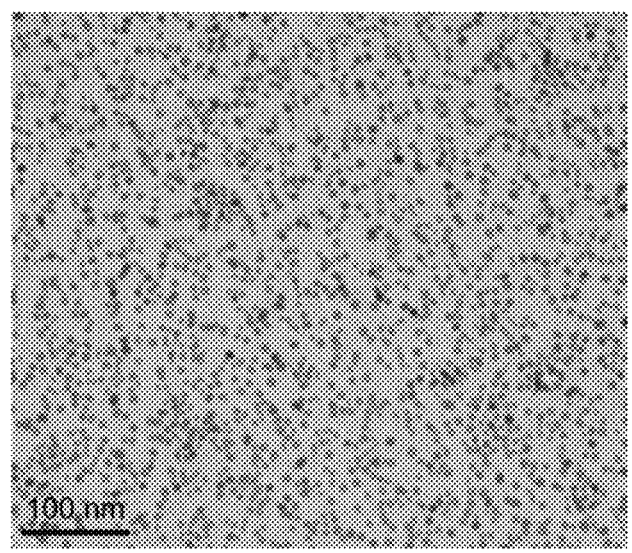
Figure 12C:
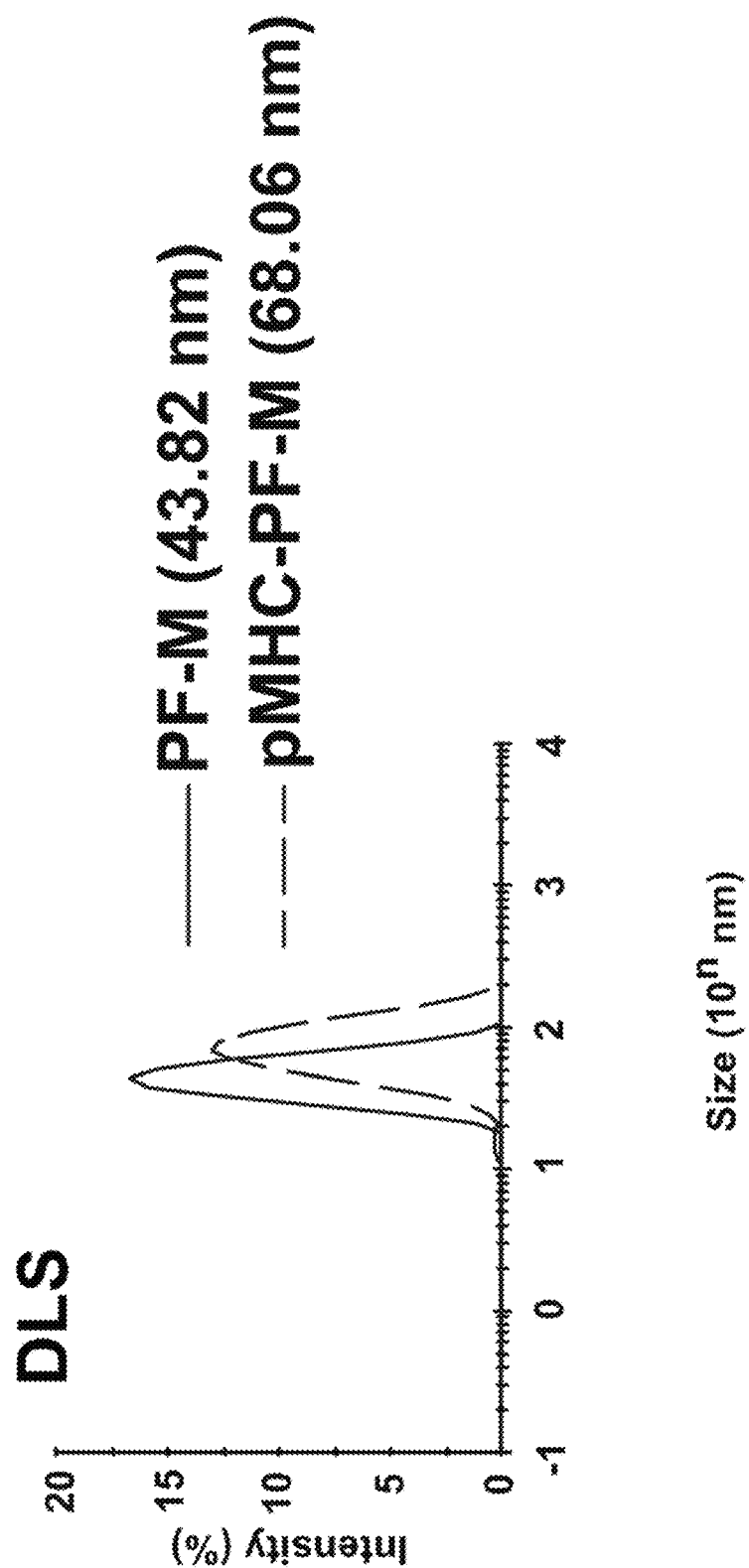

Applicant developed an optimized iron oxide NP design that does not employ surfactants for synthesis and yields highly stable, monodispersed preparations that can be loaded with optimal pMHC loads. Although several different pMHC-coating chemistries can be used (FIG. 12A), Applicant regularly uses NPs functionalized with maleimide-conjugated PEGs, which accept high valencies of pMHCs engineered to encode a free Cys at their carboxyterminal end (up to more than 60 pMHCs/NP). These pMHC class II-NPs are processed through several quality control checks to define pMHC valencies per NP (dot-ELISA, amino acid analysis), NP density, NP charge and NP size (metal core, as defined by TEM; and hydrodynamic diameter, as defined via dynamic light scattering (DLS)). FIG. 12B shows a representative TEM image and FIG. 12C shows DLS profiles of pMHC-uncoated vs. coated NPs. A typical dosing regimen involves the administration of 1-50 μg of total pMHC (NP-coated) per dose (about 2 uL of the preparation diluted in 100 uL of PBS).

Example 5

Treatment with pMHC Class II-Coated NPs

The above data are consistent with data Applicant previously obtained in mice treated with pMHC class I-NPs: pMHC class II-NPs expand cognate memory regulatory T cells (in this case TR1) that suppress the presentation of other autoantigenic peptides by local autoantigen-loaded APCs (Amrani, A. et al. (2000) Nature 406:739-742).

Figure 13A:
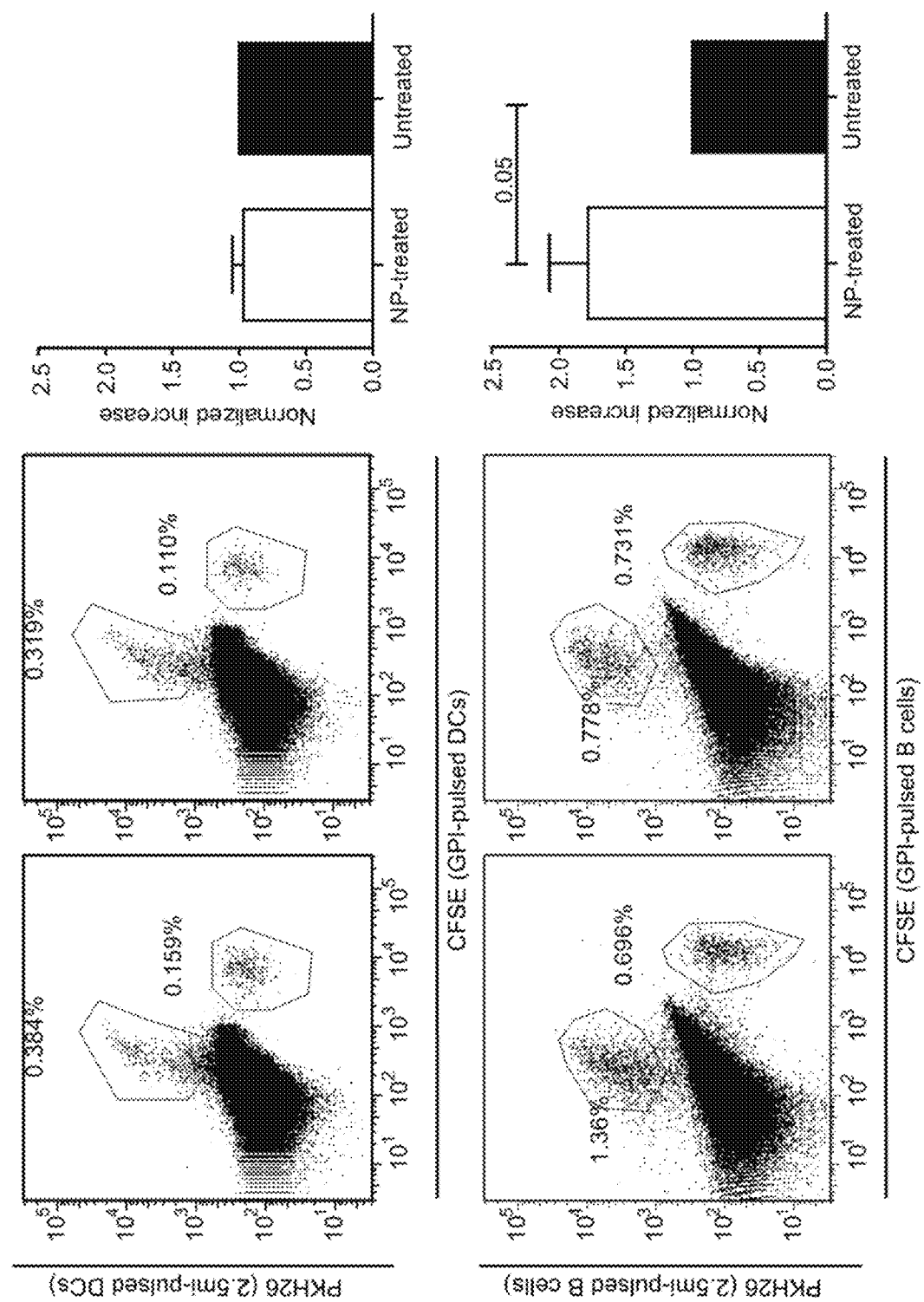
FIGS. 13A-13C show expansion and differentiation of cognate B-cells into Breg cells in pMHC class II-NP-treated mice.

Human TR1 CD4+ T-cell clones have been reported to kill certain subsets of professional APCs, such as dendritic cells (DCs) (Amrani, A. et al. (2000) Nature 406:739-742). Applicant therefore investigated whether the antigen-specific TR1 cells that expand in response top MHC class II-NP therapy suppressed autoimmunity by killing autoantigen-loaded APCs. This was done by transfusing 1:1 mixtures of DCs pulsed with 2.5mi or GPI peptides and labeled with PKH26 (2.5mi-pulsed DCs) or CFSE (GPI-pulsed DCs), into NOD mice that had received 10 doses of 2.5mi/IA$^{g7}$-NPs during the preceding 5 weeks, or NOD mice that had not received any treatment. The hosts were sacrificed 7 days later to compare the ratios of PKH26+ vs CFSE+ cells in the two different hosts. As shown in FIG. 13A (top panels), no differences were observed, suggesting that the TR1 CD4+ T-cells that expanded in response to pMHC-NP therapy do not kill antigen-expressing DCs.

To investigate whether this was a peculiarity of the type of APC used (a DC) or a general feature of other APC types, the above experiments were repeated but using splenic B-cells as opposed to DCs. Unexpectedly, it was found that the numbers of 2.5mi-pulsed B-cells expanded (rather than decreased) in hosts that had been treated with 2.5mi/IA$^{g7}$-NPs-coated NPs (FIG. 13A, bottom panels). This was unexpected because, based on the state-of-the-art, it was expected just the opposite outcome (a selective and specific decrease of 2.5mi-pulsed B-cells as compared to their GPI-pulsed counterparts).

Figure 13B:
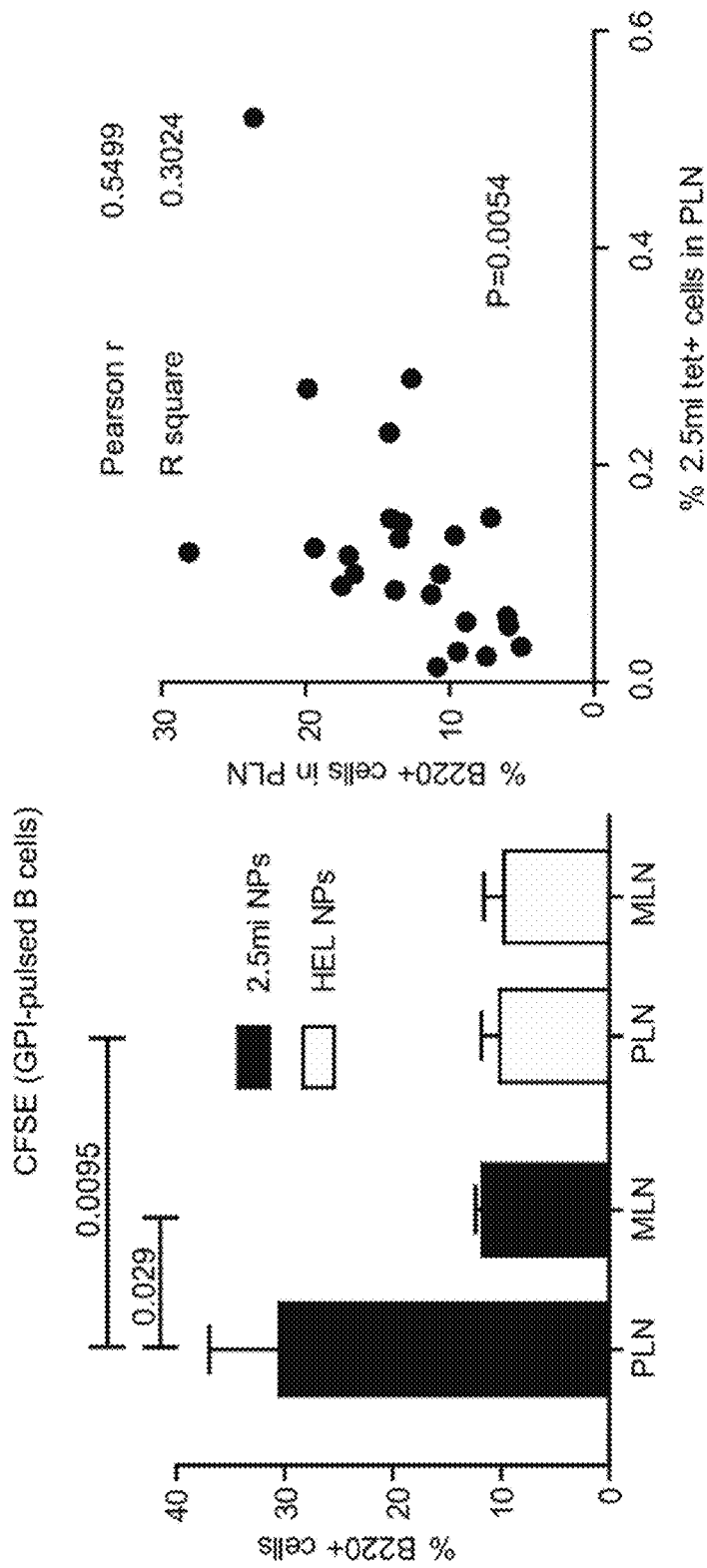

Applicant then ascertained whether such a B-cell-expanding effect of pMHC class II-NP treatment could be documented by comparing the absolute numbers and percentages of B-cells in the pancreas-draining (PLN) and non-draining (MLN) lymph nodes of mice treated with 2.5mi/IA$^{g7}$-NPs versus untreated controls. As shown in FIG. 13B, pMHC class II-NP-treated NOD mice had a marked increase in the percentage of B-cells in the PLN but not MLN. No such differences were seen in the PLN vs MLN of untreated NOD mice, indicating that these effects were a consequence of pMHC-NP therapy. Notably, there was a statistically significant correlation between the frequency of 2.5mi-specific TR1 CD4+ T-cells in the PLNs of individual mice and the frequency of PLN-associated B-cells, suggesting that such an increased recruitment of B-cells to the PLNs of the pMHC-NP-treated NOD mice was driven by the 2.5mi-specific TR1 CD4+ T-cells that expanded in response to MHC-NP therapy.

Collectively, these data raised the possibility that the B-cells that expanded in response to MHC-NP therapy might be B-regulatory cells, that is B-cells that acquire the capacity to produce IL-10 in response to cognate interactions with the pMHC-NP-expanded TR1 CD4+ T-cells. This case scenario posits that 2.5mi-specific TR1 CD4+ T-cells would induce the differentiation and expansion of undifferentiated chromogranin A-specific B-cells (chromogranin A is the natural antigenic source of the 2.5mi epitope) that have captured chromogranin A and therefore present the corresponding 2.5mi/IA$^{g7}$ pMHC complexes on their surface, to IL-10-producing Breg cells.

To test this hypothesis, Applicant transfused 2.5mi- or GPI-pulsed B-cells (labeled with PKH26) from a strain of NOD mice in which one of its two IL10 loci carries a targeted insertion of an IRES-eGFP cassette between the stop codon and polyadenylation signal of exon 5 (11), into 2.5mi/IA$^{g7}$-NP-treated or untreated NOD hosts.

Figure 13C:
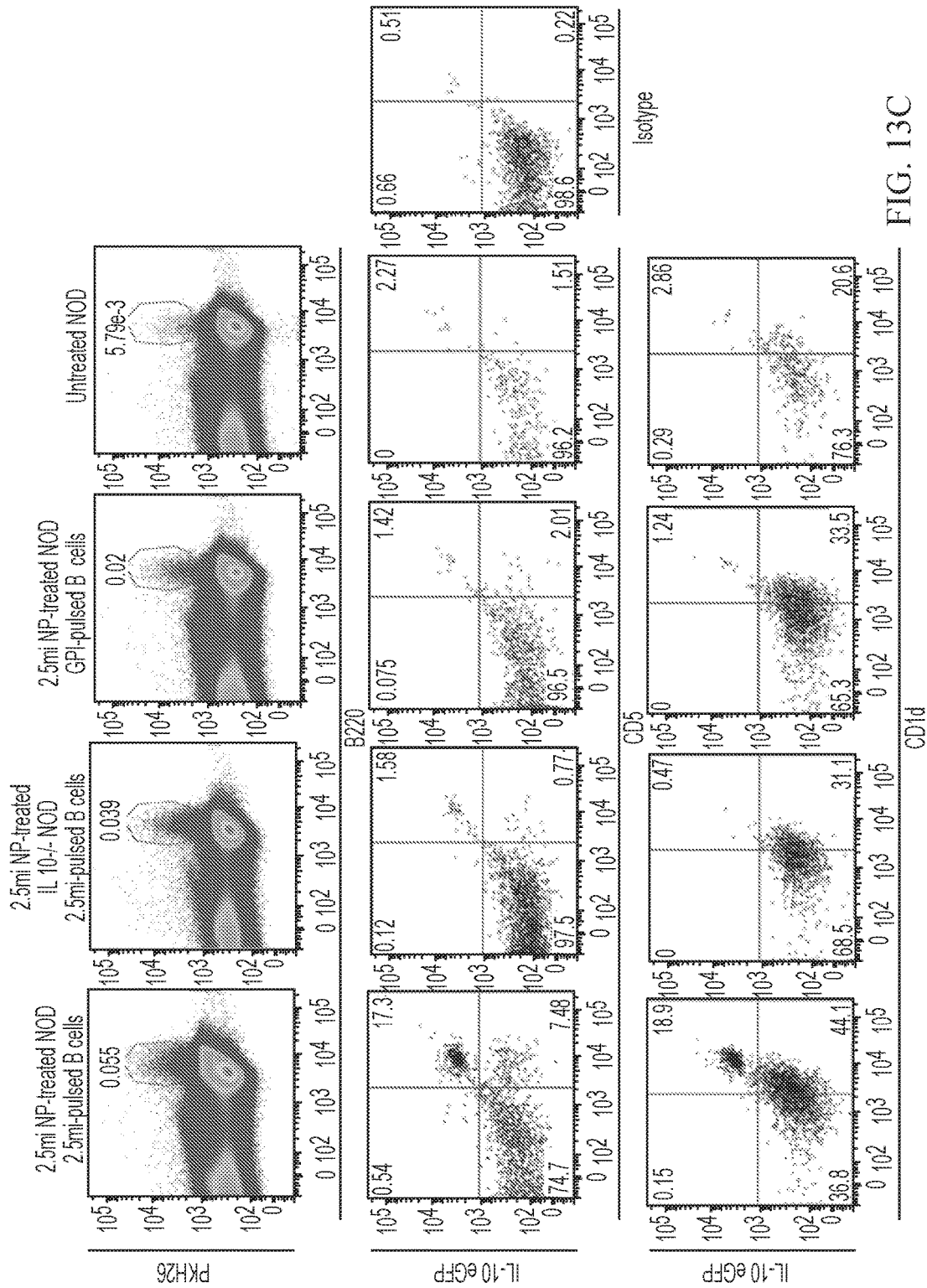
Figure 14:
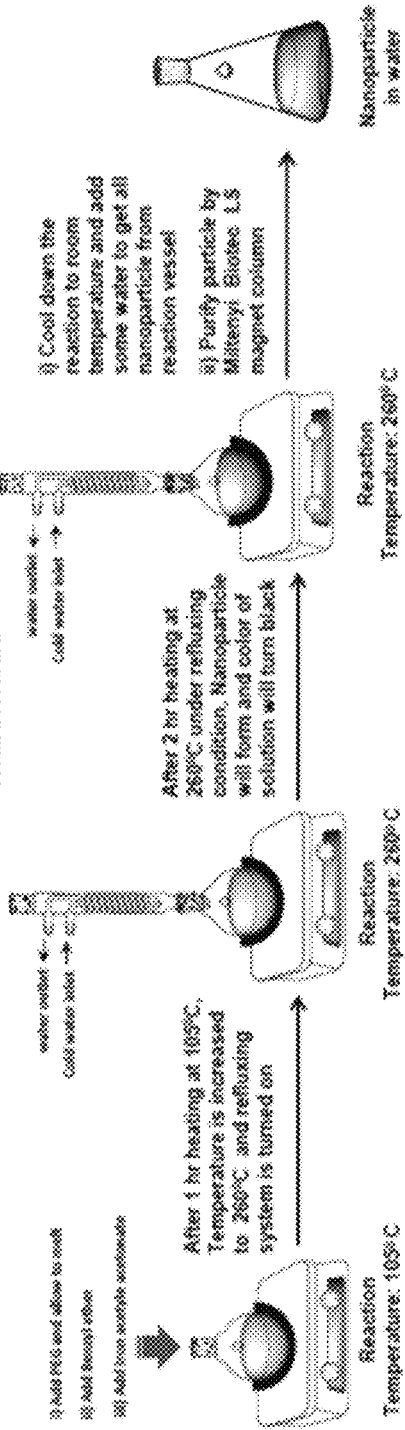
FIG. 14 shows synthesis of surface functionalized iron oxide nanoparticle by thermal decomposition of iron acetylacetonate and bioconjugation.
Figure 14:
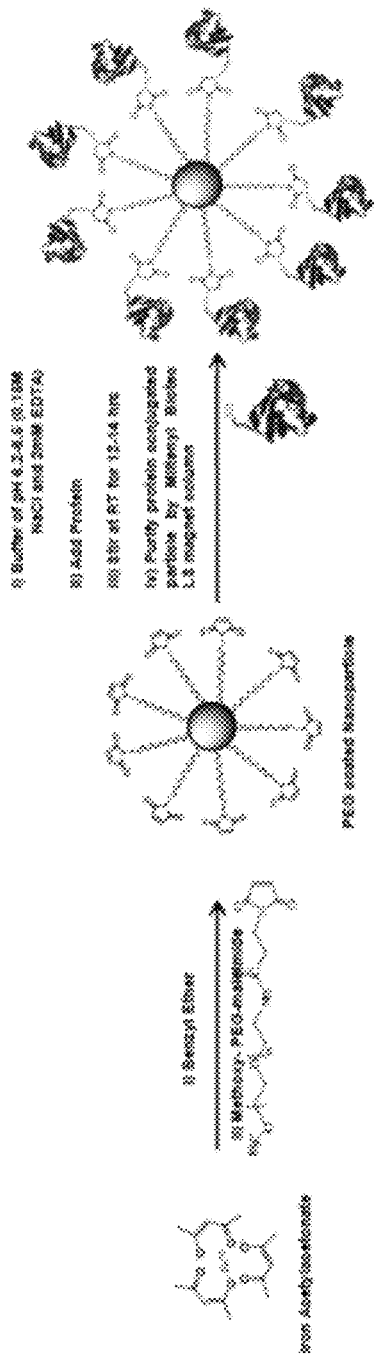

Seven days after transfer, the flow cytometric phenotype of the donor PKH26+ B-cells in the hosts (FIG. 13C, top panel) was determined. As shown in FIG. 13C (middle and bottom panels), a significant fraction of the donor B-cells expressed IL10-encoded eGFP and were both CD5+ and CD1dhigh. These are three key markers of Breg cells (Xie, J. et al. (2007) Adv Mater 19:3163; Xie, J. et al. (2006) Pure Appl. Chem. 78:1003-1014). This was only seen with B-cells pulsed with 2.5mi, but not with B-cells pulsed with a negative control peptide (GPI), and it only occurred in pMHC-NP-treated mice. Importantly, this effect was mediated, at least in part, by the IL-10 pMHC-NP-expanded TR1 CD4+ T-cells, because no such response was observed in IL-10-deficient NOD hosts.

Taken together, these data demonstrate that pMHC class II-NP therapy induces the differentiation and expansion of antigen-specific B-cells into B-regulatory cells.

The description of data suggesting the existence of B lymphocytes with regulatory properties can be found in literature dating back to 1974. Similarly to the TR1 CD4+ T-cells that expand in response to pMHC class II-NP therapy, Breg cells express immunosuppressive cytokines, including IL-10 and TGFb, as well as other molecules that can inhibit pathogenic autoreactive T- and B-cells in an antigen-dependent and highly specific manner, via cognate, pMHC class II-driven cell-to-cell interactions (Xu, C. et al. (2007) Polymer International 56:821-826). Although different stimuli have been shown to be able to induce Breg formation in vitro, and to a much lesser extent in vivo, to the best of Applicant's knowledge there is currently no therapeutic approach capable of inducing and expanding antigen-specific Breg cells in vivo. By eliciting highly disease-specific TR1 CD4+ T-cells, Applicant demonstrates that pMHC class II-based nanomedicines also elicit disease-specific Breg cells. Since Breg cells can also promote the differentiation of effector into TR1 CD4+ T-cells, pMHC class II-based nanomedicines unleash a profound and sustained immunosuppressive response that is highly antigen-specific and therefore capable of selectively suppressing autoimmune responses without compromising systemic immunity.

Example 6

Synthesis of Surface Functionalized Iron Oxide Nanoparticle by Thermal Decomposition of Iron Acetylacetonate, and Bioconjugation Thereof PEG is melted. Benzyl ether and iron acetyle acetonate is added. After 1 hr of heating at 105° C., the temperature is increased to 260° C. and refluxed. After about 2 hr, iron nanoparticles form and the color of the solution turns black. The reaction is cooled down to room temperature and some water added to extract nanoparticles from the reaction vessel. The nanoparticles are purified by MILTENYI Biotec LS magnet column. The making of iron oxide nanoparticle protein conjugates include adding protein and the iron nanoparticle at a buffered pH of 6.2-6.5 (0.15M NaCl and 2 mM EDTA), stirring at room temperature for 12-14 hours, and purifying protein conjugated particle by MILTENYI Biotec LS magnet column.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

TABLE 1

Functionalized PEG linkers

| Linker Code | Types of Nanoparticle | PEG linkers | M.W. (kDa) | Functional group | Structure |
|---|---|---|---|---|---|
| A1 | Gold nanoparticle (GNP-C) | Thiol-PEG-carboxyl | 3.5 | Amine (—NH$_2$) | HS-(CH$_2$CH$_2$O)$_n$-CH$_2$CH$_2$-NH$_2$ |
| A2 | Gold nanoparticle (GNP-N) | Thiol-PEG-amine | 3.5 | Carboxyl (—COOH) | HS-(CH$_2$CH$_2$O)$_n$-CH$_2$-COOH |
| S1 | Iron oxide Nanoparticle (SFP-C) | Dopamine-PEG-carboxyl | 3.5 | Carboxyl (—COOH) | Dopamine-NH-C(O)-CH$_2$-O-(CH$_2$CH$_2$O)$_n$-CH$_2$-COOH |
| S2 | Iron oxide Nanoparticle (SFP-N) | Dopamine-PEG-amine | 3.5 | Amine (—NH$_2$) | Dopamine-NH-C(O)-CH$_2$-O-(CH$_2$CH$_2$O)$_n$-CH$_2$CH$_2$-NH$_2$ |
| S3 | Iron oxide Nanoparticle (SFP-Z) | Dopamine-PEG-azide | 3.5 | Azide (—N$_3$) | Dopamine-NH-C(O)-CH$_2$-O-(CH$_2$CH$_2$O)$_n$-CH$_2$CH$_2$-N$_3$ |
| S4 | Iron oxide Nanoparticle (SFP-M) | Dopamine-PEG-maleimide | 3.5 | Maleimide | Dopamine-NH-C(O)-CH$_2$-O-(CH$_2$CH$_2$O)$_n$-CH$_2$CH$_2$-maleimide |

TABLE 1-continued

Functionalized PEG linkers

| Linker Code | Types of Nanoparticle | PEG linkers | M.W. (kDa) | Functional group | Structure |
|---|---|---|---|---|---|
| S5 | Iron oxide Nanoparticle (SFP-O) | Dopamine-PEG-Orthopyridyl disulfide | 3.5 | Orthopyridyl disulfide | 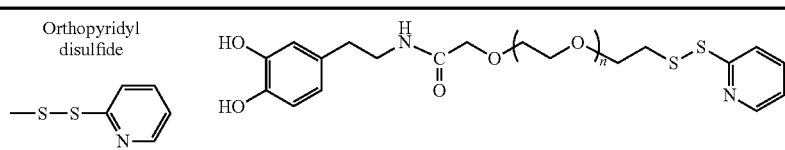 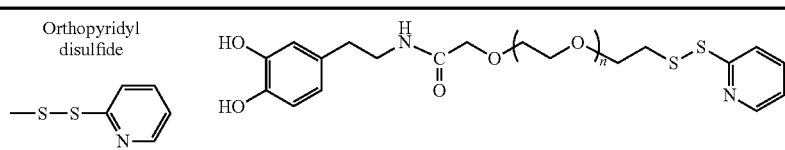 |
| P1 | Iron oxide Nanoparticle (PF-C) | carboxyl-PEG-carboxyl | 2.0 | Carboxyl (—COOH) | 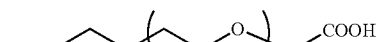 |
| P2 | Iron oxide Nanoparticle (PF-N) | Methoxy-PEG-amine | 2.0 | Amine (—NH$_2$) | 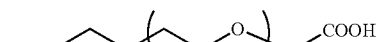 |
| P3 | Iron oxide Nanoparticle (PF-M) | Methoxy-PEG-maleimide | 2.0 | Maleimide | 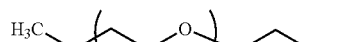 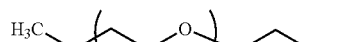 |
| P4 | Iron oxide Nanoparticle (PF-O) | Methoxy-PEG-Orthopyridyl disulfide | 2.0 | Orthopyridyl disulfide | 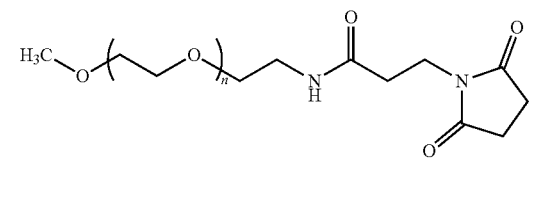 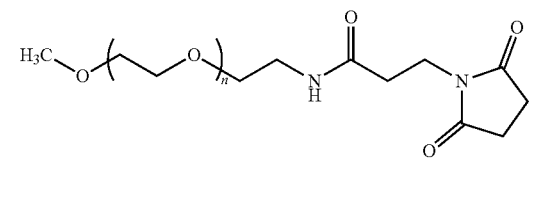 |
| P5 | Iron oxide Nanoparticle (PF) | PEG | 2.0 | Hydroxyl (—OH) | 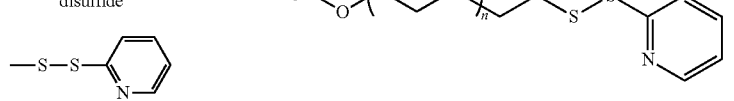 |

TABLE 2

Nanoparticle designs and pMHC-binding capacity.

| | Nanoparticle Synthesis | | | pMHC conjugation | | |
|---|---|---|---|---|---|---|
| Type | Size (nm) | Linker (Code) | Precipitation/ Aggregation | Bond | pMHC-binding capacity (pMHCs/NP) | Orientation | Magnetic purification |
| Gold GNP-C | 14 ± 2 | A1 | No | Amide | 200 | Random | No |
| Gold GNP-N | 14 ± 2 | A2 | No | Amide | 263 | Random | No |
| Gold GNP-C | 40 ± 6 | A1 | No | Amide | 5,250 | Random | No |
| Iron Oxide SFP-C | 7.4 ± 1.2 | S1 | No | Amide | 54 | Random | No |
| Iron Oxide SFP-N | 7.4 ± 1.2 | S2 | Yes | Amide | 31 | Random | No |
| Iron Oxide SFP-Z | 7.4 ± 1.2 | S3 | No | Triazole | 50 | Random | Slow |
| Iron Oxide SFP-M | 7.4 ± 1.2 | S4 | Yes | Carbon-Sulfide | <10 | Directional | No |
| Iron Oxide SFP-O | 7.4 ± 1.2 | S5 | No | Disulfide | <5 | Directional | No |
| Iron Oxide PF-C | 14.6 ± 3.8 | P1 | No | Amide | 56 | Random | No |
| Iron Oxide PF-N | 20.4 ± 4.2 | P2 | Yes | Amide | 210 | Random | No |

TABLE 2-continued

Nanoparticle designs and pMHC-binding capacity.

| | Nanoparticle Synthesis | | | pMHC conjugation | | | |
|---|---|---|---|---|---|---|---|
| | | | | | pMHC-binding | | |
| Type | Size (nm) | Linker (Code) | Precipitation/ Aggregation | Bond | capacity (pMHCs/NP) | Orientation | Magnetic purification |
| Iron Oxide PF-M | 23.5 ± 4.9 | P3 | No | Carbon-Sulfide | 64 | Directional | Efficient |
| Iron Oxide PF-O | Not formed | P4 | NA | Disulfide | NA | Directional | NA |
| Iron Oxide PF | 10.8 ± 2.7 | P5 | No | None | 0 | NA | No |

What is claimed is:

1. A method for making functionalized PEG iron oxide nanoparticles comprising thermally decomposing iron acetyl acetonate in the presence of functionalized PEG molecules and benzyl ether, wherein the thermal decomposition occurs at a temperature from about 80 to about 300° C.

2. The method of claim 1, wherein the iron oxide nanoparticle is water-soluble.

3. The method of claim 1, wherein the thermal decomposition comprises a single-step reaction.

4. The method of claim 1, wherein the temperature for the thermal decomposition is about 80 to about 200° C., or about 80 to about 150° C., or about 100 to about 250° C., or about 100 to about 200° C., or about 150 to about 250° C., or about 150 to about 250° C.

5. The method of claim 1, wherein the thermal decomposition is carried out for about 1 to about 2 hours.

6. The method of claim 1, wherein the nanoparticles are stable at about 4° C. in PBS without any detectable degradation or aggregation.

7. The method of claim 6, wherein the nanoparticles are stable for at least 6 months.

8. The method of claim 1, wherein the method further comprises purifying the nanoparticles with a magnetic column.

9. The method of claim 1, wherein the functionalized PEG molecules are maleimide functionalized.

10. The method of claim 1, wherein the functionalized PEG molecules are less than about 5 kilodaltons.

11. The method of claim 9, wherein the maleimide functionalized PEG molecules are methoxy-PEG molecules.

* * * * *

UNITED STATES PATENT AND TRADEMARK OFFICE
CERTIFICATE OF CORRECTION

PATENT NO. : 10,124,045 B2
APPLICATION NO. : 14/531707
DATED : November 13, 2018
INVENTOR(S) : Pedro Santamaria et al.

It is certified that error appears in the above-identified patent and that said Letters Patent is hereby corrected as shown below:

In the Specification

In Table 1, spanning Columns 45-46, at Lines 58-65, please delete the row labeled "S4":

"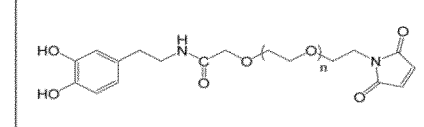"

And replace with:

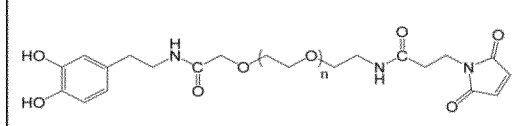

Signed and Sealed this
Twenty-sixth Day of May, 2020

Andrei Iancu
*Director of the United States Patent and Trademark Office*

SEQUENCE LISTING

```
<160> NUMBER OF SEQ ID NOS: 72

<210> SEQ ID NO 1
<211> LENGTH: 9
<212> TYPE: PRT
<213> ORGANISM: Homo sapiens

<400> SEQUENCE: 1

His Leu Val Glu Ala Leu Tyr Leu Val
1               5

<210> SEQ ID NO 2
<211> LENGTH: 9
<212> TYPE: PRT
<213> ORGANISM: Homo sapiens

<400> SEQUENCE: 2

Leu Asn Ile Asp Leu Leu Trp Ser Val
1               5

<210> SEQ ID NO 3
<211> LENGTH: 9
<212> TYPE: PRT
<213> ORGANISM: Homo sapiens

<400> SEQUENCE: 3

Val Leu Phe Gly Leu Gly Phe Ala Ile
1               5

<210> SEQ ID NO 4
<211> LENGTH: 9
<212> TYPE: PRT
<213> ORGANISM: Homo sapiens

<400> SEQUENCE: 4

Val Tyr Leu Lys Thr Asn Val Phe Leu
1               5

<210> SEQ ID NO 5
<211> LENGTH: 9
<212> TYPE: PRT
<213> ORGANISM: Homo sapiens

<400> SEQUENCE: 5

Lys Tyr Asn Lys Ala Asn Ala Phe Leu
1               5
```

```
<210> SEQ ID NO 6
<211> LENGTH: 9
<212> TYPE: PRT
<213> ORGANISM: Homo sapiens

<400> SEQUENCE: 6

Lys Tyr Asn Ile Ala Asn Val Phe Leu
1               5

<210> SEQ ID NO 7
<211> LENGTH: 9
<212> TYPE: PRT
<213> ORGANISM: Homo sapiens

<400> SEQUENCE: 7

Lys Tyr Asn Lys Ala Asn Val Phe Leu
1               5

<210> SEQ ID NO 8
<211> LENGTH: 9
<212> TYPE: PRT
<213> ORGANISM: Homo sapiens

<400> SEQUENCE: 8

Phe Gln Asp Glu Asn Tyr Leu Tyr Leu
1               5

<210> SEQ ID NO 9
<211> LENGTH: 9
<212> TYPE: PRT
<213> ORGANISM: Homo sapiens

<400> SEQUENCE: 9

Leu Tyr Leu Val Cys Gly Glu Arg Gly
1               5

<210> SEQ ID NO 10
<211> LENGTH: 10
<212> TYPE: PRT
<213> ORGANISM: Homo sapiens

<400> SEQUENCE: 10

Val Met Asn Ile Leu Leu Gln Tyr Val Val
1               5                   10

<210> SEQ ID NO 11
<211> LENGTH: 10
<212> TYPE: PRT
<213> ORGANISM: Homo sapiens

<400> SEQUENCE: 11

Arg Met Met Glu Tyr Gly Thr Thr Met Val
1               5                   10

<210> SEQ ID NO 12
<211> LENGTH: 10
<212> TYPE: PRT
<213> ORGANISM: Homo sapiens

<400> SEQUENCE: 12

Asn Leu Ala Gln Thr Asp Leu Ala Thr Val
1               5                   10

<210> SEQ ID NO 13
<211> LENGTH: 9
```

```
<212> TYPE: PRT
<213> ORGANISM: Homo sapiens

<400> SEQUENCE: 13

Gln Leu Ala Arg Gln Gln Val His Val
1               5

<210> SEQ ID NO 14
<211> LENGTH: 9
<212> TYPE: PRT
<213> ORGANISM: Homo sapiens

<400> SEQUENCE: 14

Ser Leu Ser Pro Leu Gln Ala Glu Leu
1               5

<210> SEQ ID NO 15
<211> LENGTH: 9
<212> TYPE: PRT
<213> ORGANISM: Homo sapiens

<400> SEQUENCE: 15

Ser Leu Ala Ala Gly Val Lys Leu Leu
1               5

<210> SEQ ID NO 16
<211> LENGTH: 9
<212> TYPE: PRT
<213> ORGANISM: Homo sapiens

<400> SEQUENCE: 16

Val Ile Val Met Leu Thr Pro Leu Val
1               5

<210> SEQ ID NO 17
<211> LENGTH: 9
<212> TYPE: PRT
<213> ORGANISM: Homo sapiens

<400> SEQUENCE: 17

Lys Leu Gln Val Phe Leu Ile Val Leu
1               5

<210> SEQ ID NO 18
<211> LENGTH: 9
<212> TYPE: PRT
<213> ORGANISM: Homo sapiens

<400> SEQUENCE: 18

Phe Leu Ile Val Leu Ser Val Ala Leu
1               5

<210> SEQ ID NO 19
<211> LENGTH: 9
<212> TYPE: PRT
<213> ORGANISM: Homo sapiens

<400> SEQUENCE: 19

Phe Leu Trp Ser Val Phe Met Leu Ile
1               5

<210> SEQ ID NO 20
<211> LENGTH: 9
<212> TYPE: PRT
<213> ORGANISM: Homo sapiens
```

<400> SEQUENCE: 20

Asn Leu Phe Leu Phe Leu Phe Ala Val
1               5

<210> SEQ ID NO 21
<211> LENGTH: 9
<212> TYPE: PRT
<213> ORGANISM: Homo sapiens

<400> SEQUENCE: 21

Phe Leu Phe Ala Val Gly Phe Tyr Leu
1               5

<210> SEQ ID NO 22
<211> LENGTH: 9
<212> TYPE: PRT
<213> ORGANISM: Homo sapiens

<400> SEQUENCE: 22

Tyr Leu Leu Leu Arg Val Leu Asn Ile
1               5

<210> SEQ ID NO 23
<211> LENGTH: 9
<212> TYPE: PRT
<213> ORGANISM: Homo sapiens

<400> SEQUENCE: 23

Leu Asn Ile Asp Leu Leu Trp Ser Val
1               5

<210> SEQ ID NO 24
<211> LENGTH: 9
<212> TYPE: PRT
<213> ORGANISM: Homo sapiens

<400> SEQUENCE: 24

Arg Leu Leu Cys Ala Leu Thr Ser Leu
1               5

<210> SEQ ID NO 25
<211> LENGTH: 9
<212> TYPE: PRT
<213> ORGANISM: Homo sapiens

<400> SEQUENCE: 25

Ala Leu Trp Met Arg Leu Leu Pro Leu
1               5

<210> SEQ ID NO 26
<211> LENGTH: 9
<212> TYPE: PRT
<213> ORGANISM: Homo sapiens

<400> SEQUENCE: 26

Leu Trp Met Arg Leu Leu Pro Leu Leu
1               5

<210> SEQ ID NO 27
<211> LENGTH: 9
<212> TYPE: PRT
<213> ORGANISM: Homo sapiens

<400> SEQUENCE: 27

Arg Leu Leu Pro Leu Leu Ala Leu Leu
1               5

<210> SEQ ID NO 28
<211> LENGTH: 10
<212> TYPE: PRT
<213> ORGANISM: Homo sapiens

<400> SEQUENCE: 28

His Leu Cys Gly Ser His Leu Val Glu Ala
1               5                   10

<210> SEQ ID NO 29
<211> LENGTH: 9
<212> TYPE: PRT
<213> ORGANISM: Homo sapiens

<400> SEQUENCE: 29

Ala Leu Tyr Leu Val Cys Gly Glu Arg
1               5

<210> SEQ ID NO 30
<211> LENGTH: 10
<212> TYPE: PRT
<213> ORGANISM: Homo sapiens

<400> SEQUENCE: 30

Leu Tyr Leu Val Cys Gly Glu Arg Gly Phe
1               5                   10

<210> SEQ ID NO 31
<211> LENGTH: 9
<212> TYPE: PRT
<213> ORGANISM: Homo sapiens

<400> SEQUENCE: 31

Leu Val Cys Gly Glu Arg Gly Phe Phe
1               5

<210> SEQ ID NO 32
<211> LENGTH: 10
<212> TYPE: PRT
<213> ORGANISM: Homo sapiens

<400> SEQUENCE: 32

Val Cys Gly Glu Arg Gly Phe Phe Tyr Thr
1               5                   10

<210> SEQ ID NO 33
<211> LENGTH: 8
<212> TYPE: PRT
<213> ORGANISM: Homo sapiens

<400> SEQUENCE: 33

Gly Glu Arg Gly Phe Phe Tyr Thr
1               5

<210> SEQ ID NO 34
<211> LENGTH: 9
<212> TYPE: PRT
<213> ORGANISM: Homo sapiens

<400> SEQUENCE: 34

Glu Arg Gly Phe Phe Tyr Thr Pro Lys

```
<210> SEQ ID NO 35
<211> LENGTH: 9
<212> TYPE: PRT
<213> ORGANISM: Homo sapiens

<400> SEQUENCE: 35

Phe Tyr Thr Pro Lys Thr Arg Arg Glu
1               5

<210> SEQ ID NO 36
<211> LENGTH: 11
<212> TYPE: PRT
<213> ORGANISM: Homo sapiens

<400> SEQUENCE: 36

Thr Pro Lys Thr Arg Arg Glu Ala Glu Asp Leu
1               5                   10

<210> SEQ ID NO 37
<211> LENGTH: 9
<212> TYPE: PRT
<213> ORGANISM: Homo sapiens

<400> SEQUENCE: 37

Ser Leu Gln Pro Leu Ala Leu Glu Gly
1               5

<210> SEQ ID NO 38
<211> LENGTH: 9
<212> TYPE: PRT
<213> ORGANISM: Homo sapiens

<400> SEQUENCE: 38

Ala Leu Glu Gly Ser Leu Gln Lys Arg
1               5

<210> SEQ ID NO 39
<211> LENGTH: 10
<212> TYPE: PRT
<213> ORGANISM: Homo sapiens

<400> SEQUENCE: 39

Ser Leu Gln Lys Arg Gly Ile Val Glu Gln
1               5                   10

<210> SEQ ID NO 40
<211> LENGTH: 10
<212> TYPE: PRT
<213> ORGANISM: Homo sapiens

<400> SEQUENCE: 40

Gly Ile Val Glu Gln Cys Cys Thr Ser Ile
1               5                   10

<210> SEQ ID NO 41
<211> LENGTH: 9
<212> TYPE: PRT
<213> ORGANISM: Homo sapiens

<400> SEQUENCE: 41

Ile Val Glu Gln Cys Cys Thr Ser Ile
1               5
```

```
<210> SEQ ID NO 42
<211> LENGTH: 9
<212> TYPE: PRT
<213> ORGANISM: Homo sapiens

<400> SEQUENCE: 42

Ser Leu Tyr Gln Leu Glu Asn Tyr Cys
1               5

<210> SEQ ID NO 43
<211> LENGTH: 15
<212> TYPE: PRT
<213> ORGANISM: Homo sapiens

<400> SEQUENCE: 43

Ser Leu Gln Pro Leu Ala Leu Glu Gly Ser Leu Gln Lys Arg Gly
1               5                   10                  15

<210> SEQ ID NO 44
<211> LENGTH: 11
<212> TYPE: PRT
<213> ORGANISM: Homo sapiens

<400> SEQUENCE: 44

Pro Leu Ala Leu Glu Gly Ser Leu Gln Lys Arg
1               5                   10

<210> SEQ ID NO 45
<211> LENGTH: 20
<212> TYPE: PRT
<213> ORGANISM: Homo sapiens

<400> SEQUENCE: 45

Gly Ile Val Glu Gln Cys Cys Thr Ser Ile Cys Ser Leu Tyr Gln Leu
1               5                   10                  15

Glu Asn Tyr Cys
            20

<210> SEQ ID NO 46
<211> LENGTH: 12
<212> TYPE: PRT
<213> ORGANISM: Homo sapiens

<400> SEQUENCE: 46

Gln Cys Cys Thr Ser Ile Cys Ser Leu Tyr Gln Leu
1               5                   10

<210> SEQ ID NO 47
<211> LENGTH: 20
<212> TYPE: PRT
<213> ORGANISM: Homo sapiens

<400> SEQUENCE: 47

Asn Met Tyr Ala Met Met Ile Ala Arg Phe Lys Met Phe Pro Glu Val
1               5                   10                  15

Lys Glu Lys Gly
            20

<210> SEQ ID NO 48
<211> LENGTH: 11
<212> TYPE: PRT
<213> ORGANISM: Homo sapiens

<400> SEQUENCE: 48
```

```
Arg Phe Lys Met Phe Pro Glu Val Lys Glu Lys
1               5                   10
```

<210> SEQ ID NO 49
<211> LENGTH: 13
<212> TYPE: PRT
<213> ORGANISM: Homo sapiens

<400> SEQUENCE: 49

```
Asn Phe Phe Arg Met Val Ile Ser Asn Pro Ala Ala Thr
1               5                   10
```

<210> SEQ ID NO 50
<211> LENGTH: 13
<212> TYPE: PRT
<213> ORGANISM: Homo sapiens

<400> SEQUENCE: 50

```
Gln His Leu Gln Lys Asp Tyr Arg Ala Tyr Tyr Thr Phe
1               5                   10
```

<210> SEQ ID NO 51
<211> LENGTH: 20
<212> TYPE: PRT
<213> ORGANISM: Homo sapiens

<400> SEQUENCE: 51

```
Gly Val Leu Ile Ile Gln His Leu Gln Lys Asp Tyr Arg Ala Tyr
1               5                   10                  15

Tyr Thr Phe Leu Asn
            20
```

<210> SEQ ID NO 52
<211> LENGTH: 13
<212> TYPE: PRT
<213> ORGANISM: Homo sapiens

<400> SEQUENCE: 52

```
Phe Phe Tyr Thr Pro Met Ser Arg Arg Glu Val Glu Asp
1               5                   10
```

<210> SEQ ID NO 53
<211> LENGTH: 9
<212> TYPE: PRT
<213> ORGANISM: Homo sapiens

<400> SEQUENCE: 53

```
Ser Leu Leu Leu Glu Leu Glu Glu Val
1               5
```

<210> SEQ ID NO 54
<211> LENGTH: 9
<212> TYPE: PRT
<213> ORGANISM: Homo sapiens

<400> SEQUENCE: 54

```
Leu Met Trp Ala Lys Ile Gly Pro Val
1               5
```

<210> SEQ ID NO 55
<211> LENGTH: 9
<212> TYPE: PRT
<213> ORGANISM: Homo sapiens

```
<400> SEQUENCE: 55

Val Leu Phe Ser Ser Asp Phe Arg Ile
1               5

<210> SEQ ID NO 56
<211> LENGTH: 9
<212> TYPE: PRT
<213> ORGANISM: Homo sapiens

<400> SEQUENCE: 56

Ser Leu Ser Arg Phe Ser Trp Gly Ala
1               5

<210> SEQ ID NO 57
<211> LENGTH: 9
<212> TYPE: PRT
<213> ORGANISM: Homo sapiens

<400> SEQUENCE: 57

Lys Val Glu Asp Pro Phe Tyr Trp Val
1               5

<210> SEQ ID NO 58
<211> LENGTH: 10
<212> TYPE: PRT
<213> ORGANISM: Homo sapiens

<400> SEQUENCE: 58

Arg Thr Phe Asp Pro His Phe Leu Arg Val
1               5                   10

<210> SEQ ID NO 59
<211> LENGTH: 9
<212> TYPE: PRT
<213> ORGANISM: Homo sapiens

<400> SEQUENCE: 59

Phe Leu Arg Val Pro Cys Trp Lys Ile
1               5

<210> SEQ ID NO 60
<211> LENGTH: 10
<212> TYPE: PRT
<213> ORGANISM: Homo sapiens

<400> SEQUENCE: 60

Lys Ile Thr Leu Phe Val Ile Val Pro Val
1               5                   10

<210> SEQ ID NO 61
<211> LENGTH: 9
<212> TYPE: PRT
<213> ORGANISM: Homo sapiens

<400> SEQUENCE: 61

Val Leu Gly Pro Leu Val Ala Leu Ile
1               5

<210> SEQ ID NO 62
<211> LENGTH: 9
<212> TYPE: PRT
<213> ORGANISM: Homo sapiens

<400> SEQUENCE: 62
```

```
Thr Leu Phe Val Ile Val Pro Val Leu
1               5

<210> SEQ ID NO 63
<211> LENGTH: 10
<212> TYPE: PRT
<213> ORGANISM: Homo sapiens

<400> SEQUENCE: 63

Arg Leu Ala Gly Gln Phe Leu Glu Glu Leu
1               5                   10

<210> SEQ ID NO 64
<211> LENGTH: 9
<212> TYPE: PRT
<213> ORGANISM: Homo sapiens

<400> SEQUENCE: 64

Phe Leu Tyr Gly Ala Leu Leu Leu Ala
1               5

<210> SEQ ID NO 65
<211> LENGTH: 21
<212> TYPE: PRT
<213> ORGANISM: Homo sapiens

<400> SEQUENCE: 65

Met Glu Val Gly Trp Tyr Arg Ser Pro Phe Ser Arg Val Val His Leu
1               5                   10                  15

Tyr Arg Asn Gly Lys
            20

<210> SEQ ID NO 66
<211> LENGTH: 20
<212> TYPE: PRT
<213> ORGANISM: Homo sapiens

<400> SEQUENCE: 66

Glu Val Gly Trp Tyr Arg Ser Pro Phe Ser Arg Val Val His Leu Tyr
1               5                   10                  15

Arg Asn Gly Lys
            20

<210> SEQ ID NO 67
<211> LENGTH: 12
<212> TYPE: PRT
<213> ORGANISM: Homo sapiens

<400> SEQUENCE: 67

Gly Trp Tyr Arg Ser Pro Phe Ser Arg Val Val His
1               5                   10

<210> SEQ ID NO 68
<211> LENGTH: 19
<212> TYPE: PRT
<213> ORGANISM: Homo sapiens

<400> SEQUENCE: 68

Leu His Arg Ser Gly Val Leu Ile Ile His His Leu Gln Glu Asp Tyr
1               5                   10                  15

Arg Thr Tyr

<210> SEQ ID NO 69
```

```
-continued

<211> LENGTH: 18
<212> TYPE: PRT
<213> ORGANISM: Homo sapiens

<400> SEQUENCE: 69

Thr Ala Ala Leu Ser Tyr Thr Ile Ser Arg Met Glu Glu Ser Ser Val
1               5                   10                  15

Thr Leu

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 70

His His His His His His
1               5

<210> SEQ ID NO 71
<211> LENGTH: 13
<212> TYPE: PRT
<213> ORGANISM: Homo sapiens

<400> SEQUENCE: 71

Thr Trp Thr Ala Ala Asp Thr Ala Ala Leu Ile Thr Arg
1               5                   10

<210> SEQ ID NO 72
<211> LENGTH: 14
<212> TYPE: PRT
<213> ORGANISM: Homo sapiens

<400> SEQUENCE: 72

Ala Gln Asn Ser Glu Leu Ala Ser Thr Ala Asn Met Leu Arg
1               5                   10
```